US006994957B2

(12) United States Patent
Korneluk et al.

(10) Patent No.: US 6,994,957 B2
(45) Date of Patent: Feb. 7, 2006

(54) USE OF NEURONAL APOPTOSIS INHIBITOR PROTEIN (NAIP)

(75) Inventors: Robert G. Korneluk, Ottawa (CA); Alexander E. MacKenzie, Ottawa (CA); Natalie Roy, LaJolla, CA (US); George Robertson, Ottawa (CA)

(73) Assignee: University of Ottawa, Ottawa (CA)

( * ) Notice: Subject to any disclaimer, the term of this patent is extended or adjusted under 35 U.S.C. 154(b) by 39 days.

(21) Appl. No.: 08/913,322

(22) PCT Filed: Jan. 17, 1997

(86) PCT No.: PCT/IB97/00142

§ 371 (c)(1),
(2), (4) Date: Dec. 8, 1997

(87) PCT Pub. No.: WO97/26331

PCT Pub. Date: Jul. 24, 1997

(65) Prior Publication Data

US 2002/0137028 A1 Sep. 26, 2002

(30) Foreign Application Priority Data

Jan. 19, 1996  (GB) ............................. 9601108

(51) Int. Cl.
C12P 21/06 (2006.01)
C12N 15/00 (2006.01)
C07H 21/04 (2006.01)
C07K 14/00 (2006.01)

(52) U.S. Cl. .................... 435/6; 435/69.1; 435/320; 435/366; 435/388; 530/350; 536/235

(58) Field of Classification Search ............... 435/6, 435/69.1, 320, 366, 388, 91.1, 368; 536/23.8, 536/235; 530/350
See application file for complete search history.

(56) References Cited

FOREIGN PATENT DOCUMENTS

WO   WO 94/06814   3/1994
WO   WO 95/19431   7/1995

OTHER PUBLICATIONS

Ngo et al, in The Protein Folding Problem and Tertiary Structure Prediction, 1994, Merz, et al., (ed.), Birkhauser, Boston, MA, pp. 433 and 492–495.*
Skolnick et al, From genes to protein structure and function: novel applications of computational approaches in the genomic era, Jan. 2000, Trends in Biotech. 18(1): 34–39.*
Wallace et al, Ologonucleotide Probes for the screening of recombinant DNA libraries, 1987, Methods Enzymol 152: 432–443.*
Sambrook et al, in Molecular Cloning A laboratory manual, 1989 second edition.*
Lewin, B, Genes for SMA: Multum in parvo. Cell, 80:1–5, Jan. 13, 1995.*

Bimbaum et al., "An apoptosis–inhibiting gene from a nuclear polyhedrosis virus encoding a polypeptide with Cys/His sequence motifs", J. of Virol. 68:2521 (1994).
Bimbaum et al., "An apoptosis–inhibiting gene from a nuclear polyhedrosis virus encoding a polypeptide with Cys/His sequence motifs", Abstract, J. Virol. 68:2521 (1994).
Campbell, Monoclonal Antibody Technology, Elsevier Science Publishers B.V. N.Y. NY. (1984).
Clem et al., "Induction and inhibition of apoptosis by insect viruses", Apoptosis II: The Molecular Basis of Apoptosis in Disease, Cold Spring Harbor Laboratory Press, p. 89, (1994).
Clem et al., "Anti–apoptotic genes of baculovirus", Cell Death and Differentiation, 3: 9–16, (1996).
Clem et al., "Prevention of apoptosis by a baculovirus gene during infection of insect cells", Science 254:1388, (1991).
Clem et al., "Control of programmed cell death by the baculovirus genes p35 and iap", Mol. and Cell. Biology 14:5212, (1994).
Crook et al., "An apoptosis–inhibiting baculovirus gene with a zinc finger–like motif", J. of Virol. 67:2168, (1993).
Dhein et al., "Autocrine T–cells suicide mediated by APO–1(Fas/CD95)", Abstract, Nature 373:438, (1995).
Duckett et al., "A conserved family of cellular genes related to the baculovirus iap gene and encoding apoptosis inhibitors", The EMBO Journal, 15: 2685–2694, (1996).
Fernandez et al., "Differential sensitivity of normal and Ha–ras–transformed C3H mouse embryo fibroblasts to tumor necrosis factor: . . . ", Abstract, Oncogene 9:2009, (1994).
Ferrari et al., "N–acetylcysteine (D– and L–stereoisomers) prevents apoptotic death of neuronal cells", Abstract, J. Neurosci. 1516:2857, (1995).
Fisher et al., "Dominant interfering Fas gene mutations impair apoptosis in a human autoimmune lymphoproliferative syndrome", Cell 81:935, (1995).
Gibellini et al., "Tat–expressioon Jurkat cells show an increased resistance to different apoptic stimuli . . . " Abstract, Br. J. Haematol 89:24, (1995).
Golstein et al., "Homology between reaper and the cell death domains of Fas and TNFR1", Cell 81:185, (1995).
Goruppi et al., "Dissection of c–myc domains involved in S phase induction of NIH3T3 fibroblasts", Abstract, Oncogene 9:1537, (1994).
Harrington et al., "c–Myc–induced apoptosis in fibroblasts is inherited by specific cytokines", Abstract, EMBO J. 13:3286, (1994).

(Continued)

*Primary Examiner*—Christina Chan
*Assistant Examiner*—Phuong Huynh
(74) *Attorney, Agent, or Firm*—Clark & Elbing LLP; Kristina Bieker-Brady

(57) ABSTRACT

The invention provides NAIP nucleic acid and sequences. Also provided are anti-NAIP antibodies and methods for modulating apoptosis and detecting compounds which modulate apoptosis.

8 Claims, 42 Drawing Sheets

OTHER PUBLICATIONS

Itoh et al., "A novel protein required for apoptosis . . . ", Abstract, J. Biol. Chem. 268:10932, (1993).

J. Kerr, "Neglected opportunities in apoptosis research", Trends in Cell Biology 5:55, (1995).

Katsikis et al., "Fas antigen stimulation induces marked apoptosis of T lymphocytes in human immunodeficiency virus–infected individuals", Abstract, J. Exp. Med. 1815:2029, (1995).

Korsmeyer, "Regulators of cell death", TIG 11:101, (1995).

Lerner, Nature, 299:592–596, (1982).

Li et al., "Induction of apoptosis in uninfected lymphocytes by HIV–1 Tat protein", Abstract, Science 268:429, (1995).

Liston et al., "Suppression of apoptosis in mammalian cells by NAIP and a related family of IAP genes", Nature, 379: 349–353, (1996).

Martin et al., "HIV–1 infection of human CD4+ T cells in vitro . . . ", Abstract, J. Immunol. 152:330, (1994).

Melino et al., "Tissue transglutaminase and apoptosis: sense and antisense transfection studies . . . "Abstract, Mol. Cell. Biol. 14:6584, (1994).

Muro–Cacho et al., "Anlaysis of apoptosis in lymph nodes of HIV–infected persons . . . ", Abstract, J. Immunol. 154:5555, (1995).

Nunez et al., "The Bcl–2 family of proteins: regulators of cell death and survival", Trends in Cell Biology 4:399, (1994).

Osborne et al., "Essential genes that regulate apoptosis", Trends in Cell Biology 4:394, (1994).

Rabizadeh et al., "Expression of the baculovirus p35 gene inhibits mammalian neural cell death", Abstract, J. Neurochem. 61:2318, (1993).

Rieux–Laucat et al., "Mutations in Fas associated with human lymphoproliferative syndrome and autoimmunity", Science 268:1347, (1995).

Rosenbaum et al., "Evidence for hypoxia–induced, programmed cell death of cultured neurons", Abstract, Ann. Neurol. 36:864, (1994).

Rothe et al., "The TNFR2–TRAF Signaling Complex Contains Two Novel Proteins Related to Baculoviral Inhibitor of Apoptosis Proteins", Cell, 83: 1243–1252, (1995).

Roy et al., "The gene for neuronal apoptosis inhibitory protein is partially deleted in individuals with spinal muscular atrophy", Cell 80:167, (1995).

Sato et al., "Neuronal differentiation of PC12 cells as a result of prevention of cell death by bcl–2", Abstract J. Neurobiol. 25:1227, (1994).

Steller, "Mechanisms and Genes of Cellular Suicide", Science 267:1445, (1995).

Talley et al., "Tumor necrosis facor alpha–induced apoptosis in human neuronal cells: . . . ", Abstract, Mol. Cell. Biol. 1585:2359, (1995).

Terai et al., "Apoptosis as a mechanism of cell death in cultured T lymphoblasts acutely infected with HIV–1" Abstract, J. Clin. Invest 87:1710, (1991).

Vossbeck et al., "Direct transforming activity of TGF–beta on rat fibroblasts", Abstract, Int. J. Cancer 61:92, (1995).

Westendorp et al., "Sensitization of T cells to CD95–mediated apoptosis by HIV–1 Tat and gp120", Nature 375:497, (1995).

Walkinshaw et al., "Induction of apoptosis in catecholaminergic PC12 cells by L–DOPA . . . ", Abstract, J. Clin. Invest. 95::2458, (1995).

White et al., "Genetic control of programmed cell death in drosophila", Science 264:677, (1994).

Williams et al., " Apoptosis: final control point in cell biology", Trends in Cell Biology 2:263, (1992).

Wyllie, "Death gets a brake", Nature 369:272, (1994).

* cited by examiner

```
>HSU19251, 5502 bases, 79F5B1F2 checksum.        5502 nt vs.
>naip.seq, 6133 bases, FD809D8 checksum.         6133 nt
77.8% identity; Optimized score: 13374

10        20        30        40        50        60
SEQ ID. NO:1 naip-o  TTCCGGCTGGACGTTGCCCTGTGTACCTCTTCGACTGCCTGTTCATCTACGACGAACCCC
                     :
SEQ ID. NO:2 naip.s  T-----------------------------------------------------------

70        80        90       100       110       120
            naip-o  GGGTATTGACCCCAGACAACAATGCCACTTCATATTGCATGAAGACAAAAGGTCCTGTGC
                                                         ::::::::::::::::::::
            naip.s  ----------------------------------GCATGAAGACAAAAGGTCCTGTGC
                                                              10        20

130       140       150       160       170       180
            naip-o  TCACCTGGGACCCTTCTGGACGTTGCCCTGTGTTCCTCTTCGCCTGCCTGTTCATCTACG
                    ::::::::::::::::::::::::::::::::    :::::::  :::::::::::::::
            naip.s  TCACCTGGGACCCTTCTGGACGTTGCCCTGTGTACCTCTTCGACTGCCTGTTCATCTACG
                          30        40        50        60        70        80

190       200       210       220       230       240
            naip-o  ACGAACCCCGGGTATTGACCCCAGACAACAATGCCACTTCATATTGGGGACTTCGTCTGG
                    ::::::::::::::::::::::::::::::::::::::::::::::::::::::::::::
            naip.s  ACGAACCCCGGGTATTGACCCCAGACAACAATGCCACTTCATATTGGGGACTTCGTCTGG
                          90       100       110       120       130       140

250       260       270       280       290       300
            naip-o  GATTCCAAGGTGCATTCATTGCAAAGTTCCTTAAATATTTTCTCACTGCTTCCTACTAAA
                    ::::::::::::::::::::::::::::::::::::::::::::::::::::::::::::
            naip.s  GATTCCAAGGTGCATTCATTGCAAAGTTCCTTAAATATTTTCTCACTGCTTCCTACTAAA
                         150       160       170       180       190       200

310       320       330       340       350       360
            naip-o  GGACGGACAGAGCATTTGTTCTTCAGCCACATACTTTCCTTCCACTGGCCAGCATTCTCC
                    ::::::::::::::::::::::::::::::::::::::::::::::::::::::::::::
            naip.s  GGACGGACAGAGCATTTGTTCTTCAGCCACATACTTTCCTTCCACTGGCCAGCATTCTCC
                         210       220       230       240       250       260

370       380       390       400       410       420
            naip-o  TCTATTAGACTAGAACTGTGGATAAACCTCAGAAAATGGCCACCCAGCAGAAAGCCTCTG
                    ::::::::::::::::::::::::::::::::::::::::::::::::::::::::::::
            naip.s  TCTATTAGACTAGAACTGTGGATAAACCTCAGAAAATGGCCACCCAGCAGAAAGCCTCTG
                         270       280       290       300       310       320

430       440       450       460       470       480
            naip-o  ACGAGAGGATCTCCCAGTTTGATCACAATTTGCTGCCAGAGCTGTCTGCTCTTCTGGGCC
                    ::::::::::::::::::::::::::::::::::::::::::::::::::::::::::::
            naip.s  ACGAGAGGATCTCCCAGTTTGATCACAATTTGCTGCCAGAGCTGTCTGCTCTTCTGGGCC
                         330       340       350       360       370       380
```

Fig. 5A

```
              490       500       510       520       530       540
naip-o TAGATGCAGTTCAGTTGGCAAAGGAACTAGAAGAAGAGGAGCAGAAGGAGCGAGCAAAAA
       ::::::::::::::::::::::::::::::::::::::::::::::::::::::::::::
naip.s TAGATGCAGTTCAGTTGGCAAAGGAACTAGAAGAAGAGGAGCAGAAGGAGCGAGCAAAAA
              390       400       410       420       430       440

550       560       570       580       590       600
naip-o TGCAGAAAGGCTACAACTCTCAAATGCGCAGTGAAGCAAAAAGGTTAAAGACTTTTGTGA
       ::::::::::::::::::::::::::::::::::::::::::::::::::::::::::::
naip.s TGCAGAAAGGCTACAACTCTCAAATGCGCAGTGAAGCAAAAAGGTTAAAGACTTTTGTGA
              450       460       470       480       490       500

610       620       630       640       650       660
naip-o CTTATGAGCCGTACAGCTCATGGATACCACAGGAGATGGCGGCCGCTGGGTTTTACTTCA
       ::::::::::::::::::::::::::::::::::::::::::::::::::::::::::::
naip.s CTTATGAGCCGTACAGCTCATGGATACCACAGGAGATGGCGGCCGCTGGGTTTTACTTCA
              510       520       530       540       550       560

670       680       690       700       710       720
naip-o CTGGGGTAAAATCTGGGATTCAGTGCTTCTGCTGTAGCCTAATCCTCTTTGGTGCCGGCC
       ::::::::::::::::::::::::::::::::::::::::::::::::::::::::::::
naip.s CTGGGGTAAAATCTGGGATTCAGTGCTTCTGCTGTAGCCTAATCCTCTTTGGTGCCGGCC
              570       580       590       600       610       620

730       740       750       760       770       780
naip-o TCACGAGACTCCCCATAGAAGACCACAAGAGGTTTCATCCAGATTGTGGGTTCCTTTTGA
       ::::::::::::::::::::::::::::::::::::::::::::::::::::::::::::
naip.s TCACGAGACTCCCCATAGAAGACCACAAGAGGTTTCATCCAGATTGTGGGTTCCTTTTGA
              630       640       650       660       670       680

790       800       810       820       830       840
naip-o ACAAGGATGTTGGTAACATTGCCAAGTACGACATAAGGGTGAAGAATCTGAAGAGCAGGC
       ::::::::::::::::::::::::::::::::::::::::::::::::::::::::::::
naip.s ACAAGGATGTTGGTAACATTGCCAAGTACGACATAAGGGTGAAGAATCTGAAGAGCAGGC
              690       700       710       720       730       740

850       860       870       880       890       900
naip-o TGAGAGGAGGTAAAAATGAGGTACCAAGAAGAGGAGGCTAGACTTGCATCCTTCAGGAACT
       :::::::::::::::::::::::::::::::::::::::::::::::::: :::::::::::
naip.s TGAGAGGAGGTAAAAATGAGGTACCAAGAAGAGGAGGCTAGACTTGCGTCCTTCAGGAACT
              750       760       770       780       790       800

910       920       930       940       950       960
naip-o GGCCATTTTATGTCCAAGGGATATCCCCTTGTGTGCTCTCAGAGGCTGGCTTTGTCTTTA
       ::::::::::::::::::::::::::::::::::::::::::::::::::::::::::::
naip.s GGCCATTTTATGTCCAAGGGATATCCCCTTGTGTGCTCTCAGAGGCTGGCTTTGTCTTTA
              810       820       830       840       850       860

970       980       990      1000      1010      1020
naip-o CAGGTAAACAGGACACGGTACAGTGTTTTTCCTGTGGTGGATGTTTAGGAAATTGGGAAG
       ::::::::::::::::::::::::::::::::::::::::::::::::::::::::::::
naip.s CAGGTAAACAGGACACGGTACAGTGTTTTTCCTGTGGTGGATGTTTAGGAAATTGGGAAG
              870       880       890       900       910       920
```

Fig. 5B

```
              1030       1040       1050       1060       1070       1080
naip-o  AAGGAGATGATCCTTGGAAGGAACATGCCAAATGGTTCCCCAAATGTGAATTTCTTCGGA
        ::::::::::::::::::::::::::::::::::::::::::::::::::::::::::::
naip.s  AAGGAGATGATCCTTGGAAGGAACATGCCAAATGGTTCCCCAAATGTGAATTTCTTCGGA
         930        940       950       960        970       980

1090       1100       1110       1120       1130       1140
naip-o  GTAAGAAATCCTCAGAGGAAATTACCCAGTATATTCAAAGCTACAAGGGATTTGTTGACA
        ::::::::::::::::::::::::::::::::::::::::::::::::::::::::::::
naip.s  GTAAGAAATCCTCAGAGGAAATTACCCAGTATATTCAAAGCTACAAGGGATTTGTTGACA
         990       1000       1010       1020       1030       1040

1150       1160       1170       1180       1190       1200
naip-o  TAACGGGAGAACATTTTGTGAATTCCTGGGTCCAGAGAGAATTACCTATGGCATCAGCTT
        ::::::::::::::::::::::::::::::::::::::::::::::::::::::::::::
naip.s  TAACGGGAGAACATTTTGTGAATTCCTGGGTCCAGAGAGAATTACCTATGGCATCAGCTT
        1050       1060       1070       1080       1090       1100

1210       1220       1230       1240       1250       1260
naip-o  ATTGCAATGACAGCATCTTTGCTTACGAAGAACTACGGCTGGACTCTTTTAAGGACTGGC
        ::::::::::::::::::::::::::::::::::::::::::::::::::::::::::::
naip.s  ATTGCAATGACAGCATCTTTGCTTACGAAGAACTACGGCTGGACTCTTTTAAGGACTGGC
        1110       1120       1130       1140       1150       1160

1270       1280       1290       1300       1310       1320
naip-o  CCCGGGAATCAGCTGTGGGAGTTGCAGCACTGGCCAAAGCAGGTCTTTTCTACACAGGTA
        ::::::::::::::::::::::::::::::::::::::::::::::::::::::::::::
naip.s  CCCGGGAATCAGCTGTGGGAGTTGCAGCACTGGCCAAAGCAGGTCTTTTCTACACAGGTA
        1170       1180       1190       1200       1210       1220

1330       1340       1350       1360       1370       1380
naip-o  TAAAGGACATCGTCCAGTGCTTTTCCTGTGGAGGGTGTTTAGAGAAATGGCAGGAAGGTG
        ::::::::::::::::::::::::::::::::::::::::::::::::::::::::::::
naip.s  TAAAGGACATCGTCCAGTGCTTTTCCTGTGGAGGGTGTTTAGAGAAATGGCAGGAAGGTG
        1230       1240       1250       1260       1270       1280

1390       1400       1410       1420       1430       1440
naip-o  ATGACCCATTAGACGATCACACCAGATGTTTTCCCAATTGTCCATTTCTCCAAAATATGA
        ::::::::::::::::::::::::::::::::::::::::::::::::::::::::::::
naip.s  ATGACCCATTAGACGATCACACCAGATGTTTTCCCAATTGTCCATTTCTCCAAAATATGA
        1290       1300       1310       1320       1330       1340

1450       1460       1470       1480       1490       1500
naip-o  AGTCCTCTGCGGAAGTGACTCCAGACCTTCAGAGCCGTGGTGAACTTTGTGAATTACTGG
        ::::::::::::::::::::::::::::::::::::::::::::::::::::::::::::
naip.s  AGTCCTCTGCGGAAGTGACTCCAGACCTTCAGAGCCGTGGTGAACTTTGTGAATTACTGG
        1350       1360       1370       1380       1390       1400

1510       1520       1530       1540       1550       1560
naip-o  AAACCACAAGTGAAAGCAATCTTGAAGATTCAATAGCAGTTGGTCCTATAGTGCCAGAAA
        ::::::::::::::::::::::::::::::::::::::::::::::::::::::::::::
naip.s  AAACCACAAGTGAAAGCAATCTTGAAGATTCAATAGCAGTTGGTCCTATAGTGCCAGAAA
        1410       1420       1430       1440       1450       1460
```

Fig. 5C

```
            1570       1580       1590       1600       1610       1620
naip-o  TGGCACAGGGTGAAGCCCAGTGGTTTCAAGAGGCAAAGAATCTGAATGAGCAGCTGAGAG
        ::::::::::::::::::::::::::::::::::::::::::::::::::::::::::::
naip.s  TGGCACAGGGTGAAGCCCAGTGGTTTCAAGAGGCAAAGAATCTGAATGAGCAGCTGAGAG
            1470       1480       1490       1500       1510       1520

1630       1640       1650       1660       1670       1680
naip-o  CAGCTTATACCAGCGCCAGTTTCCGCCACATGTCTTTGCTTGATATCTCTTCCGATCTGG
        ::::::::::::::::::::::::::::::::::::::::::::::::::::::::::::
naip.s  CAGCTTATACCAGCGCCAGTTTCCGCCACATGTCTTTGCTTGATATCTCTTCCGATCTGG
            1530       1540       1550       1560       1570       1580

1690       1700       1710       1720       1730       1740
naip-o  CCACGGACCACTTGCTGGGCTGTGATCTGTCTATTGCTTCAAAACACATCAGCAAACCTG
        ::::::::::::::::::::::::::::::::::::::::::::::::::::::::::::
naip.s  CCACGGACCACTTGCTGGGCTGTGATCTGTCTATTGCTTCAAAACACATCAGCAAACCTG
            1590       1600       1610       1620       1630       1640

1750       1760       1770       1780       1790       1800
naip-o  TGCAAGAACCTCTGGTGCTGCCTGAGGTCTTTGGCAACTTGAACTCTGTCATGTGTGTGG
        ::::::::::::::::::::::::::::::::::::::::::::::::::::::::::::
naip.s  TGCAAGAACCTCTGGTGCTGCCTGAGGTCTTTGGCAACTTGAACTCTGTCATGTGTGTGG
            1650       1660       1670       1680       1690       1700

1810       1820       1830       1840       1850       1860
naip-o  AGGGTGAAGCTGGAAGTGGAAAGACGGTCCTCCTGAAGAAAATAGCTTTTCTGTGGGCAT
        ::::::::::::::::::::::::::::::::::::::::::::::::::::::::::::
naip.s  AGGGTGAAGCTGGAAGTGGAAAGACGGTCCTCCTGAAGAAAATAGCTTTTCTGTGGGCAT
            1710       1720       1730       1740       1750       1760

1870       1880       1890       1900       1910       1920
naip-o  CTGGATGCTGTCCCCTGTTAAACAGGTTCCAGCTGGTTTTCTACCTCTCCCTTAGTTCCA
        ::::::::::::::::::::::::::::::::::::::::::::::::::::::::::::
naip.s  CTGGATGCTGTCCCCTGTTAAACAGGTTCCAGCTGGTTTTCTACCTCTCCCTTAGTTCCA
            1770       1780       1790       1800       1810       1820

1930       1940       1950       1960       1970       1980
naip-o  CCAGACCAGACGAGGGGCTGGCCAGTATCATCTGTGACCAGCTCCTAGAGAAAGAAGGAT
        ::::::::::::::::::::::::::::::::::::::::::::::::::::::::::::
naip.s  CCAGACCAGACGAGGGGCTGGCCAGTATCATCTGTGACCAGCTCCTAGAGAAAGAAGGAT
            1830       1840       1850       1860       1870       1880

1990       2000       2010       2020       2030       2040
naip-o  CTGTTACTGAAATGTGCATGAGGAACATTATCCAGCAGTTAAAGAATCAGGTCTTATTCC
        ::::::::::::::::::::::::::::::::::::::::::::::::::::::::::::
naip.s  CTGTTACTGAAATGTGCATGAGGAACATTATCCAGCAGTTAAAGAATCAGGTCTTATTCC
            1890       1900       1910       1920       1930       1940

2050       2060       2070       2080       2090       2100
naip-o  TTTTAGATGACTACAAAGAAATATGTTCAATCCCTCAAGTCATAGGAAAACTGATTCAAA
        ::::::::::::::::::::::::::::::::::::::::::::::::::::::::::::
naip.s  TTTTAGATGACTACAAAGAAATATGTTCAATCCCTCAAGTCATAGGAAAACTGATTCAAA
            1950       1960       1970       1980       1990       2000
```

Fig. 5D

```
            2110       2120       2130       2140       2150       2160
naip-o  AAAACCACTTATCCCGGACCTGCCTATTGATTGCTGTCCGTACAAACAGGGCCAGGGACA
        ::::::::::::::::::::::::::::::::::::::::::::::::::::::::::::
naip.s  AAAACCACTTATCCCGGACCTGCCTATTGATTGCTGTCCGTACAAACAGGGCCAGGGACA
        2010       2020       2030       2040       2050       2060

2170       2180       2190       2200       2210       2220
naip-o  TCCGCCGATACCTAGAGACCATTCTAGAGATCCAAGCATTTCCCTTTTATAATACTGTCT
        ::::::::::::::::::::::::::::::::: :::::::::::::::::::::::::
naip.s  TCCGCCGATACCTAGAGACCATTCTAGAGATCAAAGCATTTCCCTTTTATAATACTGTCT
        2070       2080       2090       2100       2110       2120

2230       2240       2250       2260       2270       2280
naip-o  GTATATTACGGAAGCTCTTTTCACATAATATGACTCGTCTGCGAAAGTTTATGGTTTACT
        ::::::::::::::::::::::::::::::::::::::::::::::::::::::::::::
naip.s  GTATATTACGGAAGCTCTTTTCACATAATATGACTCGTCTGCGAAAGTTTATGGTTTACT
        2130       2140       2150       2160       2170       2180

2290       2300       2310       2320       2330       2340
naip-o  TTGGAAAGAACCAAAGTTTGCAGAAGATACAGAAAACTCCTCTCTTTGTGGCGGCGATCT
        ::::::::::::::::::::::::::::::::::::::::::::::::::::::::::::
naip.s  TTGGAAAGAACCAAAGTTTGCAGAAGATACAGAAAACTCCTCTCTTTGTGGCGGCGATCT
        2190       2200       2210       2220       2230       2240

2350       2360       2370       2380       2390       2400
naip-o  GTGCTCATTGGTTTCAGTATCCTTTTGACCCATCCTTTGATGATGTGGCTGTTTTCAAGT
        ::::::::::::::::::::::::::::::::::::::::::::::::::::::::::::
naip.s  GTGCTCATTGGTTTCAGTATCCTTTTGACCCATCCTTTGATGATGTGGCTGTTTTCAAGT
        2250       2260       2270       2280       2290       2300

2410       2420       2430       2440       2450       2460
naip-o  CCTATATGGAACGCCTTTCCTTAAGGAACAAAGCGACAGCTGAAATTCTCAAAGCAACTG
        ::::::::::::::::::::::::::::::::::::::::::::::::::::::::::::
naip.s  CCTATATGGAACGCCTTTCCTTAAGGAACAAAGCGACAGCTGAAATTCTCAAAGCAACTG
        2310       2320       2330       2340       2350       2360

2470       2480       2490       2500       2510       2520
naip-o  TGTCCTCCTGTGGTGAGCTGGCCTTGAAAGGGTTTTTTTCATGTTGCTTTGAGTTTAATG
        ::::::::::::::::::::::::::::::::::::::::::::::::::::::::::::
naip.s  TGTCCTCCTGTGGTGAGCTGGCCTTGAAAGGGTTTTTTTCATGTTGCTTTGAGTTTAATG
        2370       2380       2390       2400       2410       2420

2530       2540       2550       2560       2570       2580
naip-o  ATGATGATCTCGCAGAAGCAGGGGTTGATGAAGATGAAGATCTAACCATGTGCTTGATGA
        ::::::::::::::::::::::::::::::::::::::::::::::::::::::::::::
naip.s  ATGATGATCTCGCAGAAGCAGGGGTTGATGAAGATGAAGATCTAACCATGTGCTTGATGA
        2430       2440       2450       2460       2470       2480

2590       2600       2610       2620       2630       2640
naip-o  GCAAATTTACAGCCCAGAGACTAAGACCATTCTACCGGTTTTTAAGTCCTGCCTTCCAAG
        ::::::::::::::::::::::::::::::::::::::::::::::::::::::::::::
naip.s  GCAAATTTACAGCCCAGAGACTAAGACCATTCTACCGGTTTTTAAGTCCTGCCTTCCAAG
        2490       2500       2510       2520       2530       2540
```

Fig. 5E

```
              2650       2660       2670       2680       2690       2700
naip-o AATTTCTTGCGGGGATGAGGCTGATTGAACTCCTGGATTCAGATAGGCAGGAACATCAAG
       ::::::::::::::::::::::::::::::::::::::::::::::::::::::::::::
naip.s AATTTCTTGCGGGGATGAGGCTGATTGAACTCCTGGATTCAGATAGGCAGGAACATCAAG
         2550       2560       2570       2580       2590       2600

2710       2720       2730       2740       2750       2760
naip-o ATTTGGGACTGTATCATTTGAAACAAATCAACTCACCCATGATGACTGTAAGCGCCTACA
       ::::::::::::::::::::::::::::::::::::::::::::::::::::::::::::
naip.s ATTTGGGACTGTATCATTTGAAACAAATCAACTCACCCATGATGACTGTAAGCGCCTACA
         2610       2620       2630       2640       2650       2660

2770       2780       2790       2800       2810       2820
naip-o ACAATTTTTTGAACTATGTCTCCAGCCTCCCTTCAACAAAAGCAGGGCCCAAAATTGTGT
       ::::::::::::::::::::::::::::::::::::::::::::::::::::::::::::
naip.s ACAATTTTTTGAACTATGTCTCCAGCCTCCCTTCAACAAAAGCAGGGCCCAAAATTGTGT
         2670       2680       2690       2700       2710       2720

2830       2840       2850       2860       2870       2880
naip-o CTCATTTGCTCCATTTAGTGGATAACAAAGAGTCATTGGAGAATATATCTGAAAATGATG
       ::::::::::::::::::::::::::::::::::::::::::::::::::::::::::::
naip.s CTCATTTGCTCCATTTAGTGGATAACAAAGAGTCATTGGAGAATATATCTGAAAATGATG
         2730       2740       2750       2760       2770       2780

2890       2900       2910       2920       2930       2940
naip-o ACTACTTAAAGCACCAGCCAGAAATTTCACTGCAGATGCAGTTACTTAGGGGATTGTGGC
       ::::::::::::::::::::::::::::::::::::::::::::::::::::::::::::
naip.s ACTACTTAAAGCACCAGCCAGAAATTTCACTGCAGATGCAGTTACTTAGGGGATTGTGGC
         2790       2800       2810       2820       2830       2840

2950       2960       2970       2980       2990       3000
naip-o AAATTTGTCCACAAGCTTACTTTTCAATGGTTTCAGAACATTTACTGGTTCTTGCCCTGA
       ::::::::::::::::::::::::::::::::::::::::::::::::::::::::::::
naip.s AAATTTGTCCACAAGCTTACTTTTCAATGGTTTCAGAACATTTACTGGTTCTTGCCCTGA
         2850       2860       2870       2880       2890       2900

3010       3020       3030       3040       3050       3060
naip-o AAACTGCTTATCAAAGCAACACTGTTGCTGCGTGTTCTCCATTTGTTTTGCAATTCCTTC
       ::::::::::::::::::::::::::::::::::::::::::::::::::::::::::::
naip.s AAACTGCTTATCAAAGCAACACTGTTGCTGCGTGTTCTCCATTTGTTTTGCAATTCCTTC
         2910       2920       2930       2940       2950       2960

3070       3080       3090       3100       3110       3120
naip-o AAGGGAGAACACTGACTTTGGGTGCGCTTAACTTACAGTACTTTTTCGACCACCCAGAAA
       ::::::::::::::::::::::::::::::::::::::::::::::::::::::::::::
naip.s AAGGGAGAACACTGACTTTGGGTGCGCTTAACTTACAGTACTTTTTCGACCACCCAGAAA
         2970       2980       2990       3000       3010       3020

3130       3140       3150       3160       3170       3180
naip-o GCTTGTCATTGTTGAGGAGCATCCACTTCTCAATACGAGGAAATAAGACATCACCCAGAG
       ::::::::::::::::::::::::: ::::::::::::::::::::::::::::::::::
naip.s GCTTGTCATTGTTGAGGAGCATCCACTTCCCAATACGAGGAAATAAGACATCACCCAGAG
         3030       3040       3050       3060       3070       3080
```

Fig. 5F

```
            3190      3200      3210      3220      3230      3240
naip-o  CACATTTTTCAGTTCTGGAAACATGTTTTGACAAATCACAGGTGCCAACTATAGATCAGG
        ::::::::::::::::::::::::::::::::::::::::::::::::::::::::::::
naip.s  CACATTTTTCAGTTCTGGAAACATGTTTTGACAAATCACAGGTGCCAACTATAGATCAGG
            3090      3100      3110      3120      3130      3140

3250      3260      3270      3280      3290      3300
naip-o  ACTATGCTTCTGCCTTTGAACCTATGAATGAATGGGAGCGAAATTTAGCTGAAAAAGAGG
        ::::::::::::::::::::::::::::::::::::::::::::::::::::::::::::
naip.s  ACTATGCTTCTGCCTTTGAACCTATGAATGAATGGGAGCGAAATTTAGCTGAAAAAGAGG
            3150      3160      3170      3180      3190      3200

3310      3320      3330      3340      3350      3360
naip-o  ATAATGTAAAGAGCTATATGGATATGCAGCGCAGGGCATCACCAGACCTTAGTACTGGCT
        ::::::::::::::::::::::::::::::::::::::::::::::::::::::::::::
naip.s  ATAATGTAAAGAGCTATATGGATATGCAGCGCAGGGCATCACCAGACCTTAGTACTGGCT
            3210      3220      3230      3240      3250      3260

3370      3380      3390      3400      3410      3420
naip-o  ATTGGAAACTTTCTCCAAAGCAGTACAAGATTCCCTGTCTAGAAGTCGATGTGAATGATA
        ::::::::::::::::::::::::::::::::::::::::::::::::::::::::::::
naip.s  ATTGGAAACTTTCTCCAAAGCAGTACAAGATTCCCTGTCTAGAAGTCGATGTGAATGATA
            3270      3280      3290      3300      3310      3320

3430      3440      3450      3460      3470      3480
naip-o  TTGATGTTGTAGGCCAGGATATGCTTGAGATTCTAATGACAGTTTTCTCAGCTTCACAGC
        ::::::::::::::::::::::::::::::::::::::::::::::::::::::::::::
naip.s  TTGATGTTGTAGGCCAGGATATGCTTGAGATTCTAATGACAGTTTTCTCAGCTTCACAGC
            3330      3340      3350      3360      3370      3380

3490      3500      3510      3520      3530      3540
naip-o  GCATCGAACTCCATTTAAACCACAGCAGAGGCTTTATAGAAAGCATCCGCCCAGCTCTTG
        ::::::::::::::::::::::::::::::::::::::::::::::::::::::::::::
naip.s  GCATCGAACTCCATTTAAACCACAGCAGAGGCTTTATAGAAAGCATCCGCCCAGCTCTTG
            3390      3400      3410      3420      3430      3440

3550      3560      3570      3580      3590      3600
naip-o  AGCTGTCTAAGGCCTCTGTCACCAAGTGCTCCATAAGCAAGTTGGAACTCAGCGCAGCCG
        ::::::::::::::::::::::::::::::::::::::::::::::::::::::::::::
naip.s  AGCTGTCTAAGGCCTCTGTCACCAAGTGCTCCATAAGCAAGTTGGAACTCAGCGCAGCCG
            3450      3460      3470      3480      3490      3500

3610      3620      3630      3640      3650      3660
naip-o  AACAGGAACTGCTTCTCACCCTGCCTTCCCTGGAATCTCTTGAAGTCTCAGGGACAATCC
        ::::::::::::::::::::::::::::::::::::::::::::::::::::::::::::
naip.s  AACAGGAACTGCTTCTCACCCTGCCTTCCCTGGAATCTCTTGAAGTCTCAGGGACAATCC
            3510      3520      3530      3540      3550      3560

3670      3680      3690      3700      3710      3720
naip-o  AGTCACAAGACCAAATCTTTCCTAATCTGGATAAGTTCCTGTGCCTGAAAGAACTGTCTG
        ::::::::::::::::::::::::::::::::::::::::::::::::::::::::::::
naip.s  AGTCACAAGACCAAATCTTTCCTAATCTGGATAAGTTCCTGTGCCTGAAAGAACTGTCTG
            3570      3580      3590      3600      3610      3620
```

Fig. 5G

```
                3730       3740       3750       3760       3770       3780
naip-o  TGGATCTGGAGGGCAATATAAATGTTTTTTCAGTCATTCCTGAAGAATTTCCAAACTTCC
        ::::::::::::::::::::::::::::::::::::::::::::::::::::::::::::
naip.s  TGGATCTGGAGGGCAATATAAATGTTTTTTCAGTCATTCCTGAAGAATTTCCAAACTTCC
          3630       3640       3650       3660       3670       3680

3790       3800       3810       3820       3830       3840
naip-o  ACCATATGGAGAAATTATTGATCCAAATTTCAGCTGAGTATGATCCTTCCAAACTAGTAA
        ::::::::::::::::::::::::::::::::::::::::::::::::::::::::::::
naip.s  ACCATATGGAGAAATTATTGATCCAAATTTCAGCTGAGTATGATCCTTCCAAACTAGTAA
          3690       3700       3710       3720       3730       3740 naip-o  ------------------------------------------------------------ naip.s  AATTAATTCAAAATTCTCCAAACCTTCATGTTTTCCATCTGAAGTGTAACTTCTTTTCGG
          3750       3760       3770       3780       3790       3800 naip-o  ------------------------------------------------------------ naip.s  ATTTTGGGTCTCTCATGACTATGCTTGTTTCCTGTAAGAAACTCACAGAAATTAAGTTTT
          3810       3820       3830       3840       3850       3860

3840       3850       3860
naip-o  -----------------------------------TGCCAGTTTGCCAAATTTTATTTCTCTGA
                                           ::::::::::::::::::::::::::
naip.s  CGGATTCATTTTTTTCAAGCCGTCCCATTTGTTGCCAGTTTGCCAAATTTTATTTCTCTGA
          3870       3880       3890       3900       3910       3920

3870       3880       3890       3900       3910       3920
naip-o  AGATATTAAATCTTGAAGGCCAGCAATTTCCTGATGAGGAAACATCAGAAAAATTTGCCT
        ::::::::::::::::::::::::::::::::::::::::::::::::::::::::::::
naip.s  AGATATTAAATCTTGAAGGCCAGCAATTTCCTGATGAGGAAACATCAGAAAAATTTGCCT
          3930       3940       3950       3960       3970       3980

3930       3940       3950       3960       3970       3980
naip-o  ACATTTTAGGTTCTCTTAGTAACCTGGAAGAATTGATCCTTCCTACTGGGGATGGAATTT
        ::::::::::::::::::::::::::::::::::::::::::::::::::::::::::::
naip.s  ACATTTTAGGTTCTCTTAGTAACCTGGAAGAATTGATCCTTCCTACTGGGGATGGAATTT
          3990       4000       4010       4020       4030       4040

3990       4000       4010       4020       4030       4040
naip-o  ATCGAGTGGCCAAACTGATCATCCAGCAGTGTCAGCAGCTTCATTGTCTCCGAGTCCTCT
        ::::::::::::::::::::::::::::::::::::::::::::::::::::::::::::
naip.s  ATCGAGTGGCCAAACTGATCATCCAGCAGTGTCAGCAGCTTCATTGTCTCCGAGTCCTCT
          4050       4060       4070       4080       4090       4100

4050       4060       4070       4080       4090       4100
naip-o  CATTTTTCAAGACTTTGAATGATGACAGCGTGGTGGAAATTGGTTAAA----AAT--GTG
        ::::::::::::::::::::::::::::::::::::::::::::::::    :::  :::
naip.s  CATTTTTCAAGACTTTGAATGATGACAGCGTGGTGGAAATTGCCAAAGTAGCAATCAGTG
          4110       4120       4130       4140       4150       4160
```

Fig. 5H

```
           4110      4120      4130      4140      4150
naip-o ----TCTGCAGGCACAC-AGGACGT---GCCTTCACCCC--CATCTGACTAT-GTGGAAA
       : : :::  ::   :: :: :   :: ::::  :   ::    :: ::   : ::::
naip.s GAGGTTTCCAGAAACTTGAGAACCTAAAGCTTTCAATCAATCACAAGATTACAGAGGAAG
       4170      4180      4190     4200      4210      4220

4160      4170      4180      4190              4200
naip-o GAGTT-GACAGTCCCATGGCATACTCTTCCA-ATGGCAAAGT-----GAAT--GACAAGC
       ::    ::  : :  :     :::   : : ::: ::::  :      :: :  ::::
naip.s GATACAGAAATTTCTTTCAAGCACTGGACAACATGCCAAACTTGCAGGAGTTGGACATCT
       4230      4240      4250      4260      4270      4280

4210      4220      4230      4240
naip-o ---GGTTTTATCCAGAGTCTTCCTA---TAAATCCACGCCGGT----TCCTGAAGT----
       ::    ::    :::::: : :      : :   :::: : ::    :: :  :::
naip.s CCAGGCATTTCACAGAGTGTATCAAAGCTCAGGCCACAACAGTCAAGTCTTTGAGTCAAT
       4290      4300      4310      4320      4330      4340

4250      4260      4270      4280      4290
naip-o --GGTTCAGGAGCTTCCA-------TTA-ACTTCGCCTGTGGA--TGACTTCAGGCAGCC
       :  :  : ::  ::  :::       :::  :::   : ::   :  :: ::   ::  ::
naip.s GTGTGTTACGA-CTACCAAGGCTCATTAGACTGAACATGTTAAGTTGGCTCTTGGATGCA
       4350      4360      4370      4380      4390      4400

4300      4310      4320      4330      4340
naip-o TC-GTTACAGCAGCG------GTGGTAACTTTGAGACACCTTCAAAAAGAGCAC------
       :  ::   :::  :         ::   : :     :::: : ::::  ::  ::
naip.s GATGATATTGCATTGCTTAATGTCATGAAAGAAAGACATCCTCAATCTAAGTACTTAACT
       4410      4420      4430      4440      4450      4460

4350      4360      4370      4380      4390
naip-o ---CTGCA--AAGGGA-AGAGCAGGAAGGTCAAAGAGAACAGAGC---AAGAT-CA-CTA
       ::   ::   :: :::  :  ::  :  ::   :: ::   ::::   :::::  :: :::
naip.s ATTCTCCAGAAATGGATACTGCCGTTCTCTCCAATCATTCAGAAATAAAAGATTCAGCTA
       4470      4480      4490      4500      4510      4520

4400      4410      4420      4430      4440
naip-o TGAGA--CAGACTACACAACTGGCGGCGAGTCCTGT-GATGAGCTGGAGGAGGAC-TGGA
       :      : :: :  : : ::  :     :    :  ::   :: ::  :   :   : ::
naip.s AAAACTGCTGAATCAATAATTTGTCTTGGGGCATATTGAGGATGTAAAAAAGTTGTTGA
       4530      4540      4550      4560      4570      4580

4450      4460      4470      4480
naip-o TCAGGG----------AATATCCACC--TATCACTTCAGAT----CA-ACAAAGACAAC
       :  :     : ::::::   :::   : :: :   :: :::::   ::
naip.s TTAATGCTAAAAACCAAATTATCCAAAATTATTTTATTAAATATTGCATACAAAAGAAAA
       4590      4600      4610      4620      4630      4640

4490              4500      4510      4520      4530
naip-o TGT---------------ACAAGAGGAATTTTGACACTGGCCTACAGGAATACAAG--
       :::              :::: :  ::    ::::  :  ::  ::    ::   :
naip.s TGTGTAAGGCTTGCTAAAAAACAAAACAAAACAAAACACAGTCCTGCATACTCACCACCA
       4650      4660      4670      4680      4690      4700
```

Fig. 5I

```
            4540              4550                        4560
naip-o AGCTTAC------AATCAGAAC--------TTGA------TGAG--ATCAA-------TA
       ::::  :      ::::: ::          ::::      ::::  :::  :          ::
naip.s AGCTCAAGAAATAAATCATCACCAATACCTTTGAGGTCCCTGAGTAATCCACCCCAGCTA
            4710      4720      4730     .4740      4750      4760

4570      4580      4590      4600
naip-o AAG---AACTCTCCCGTTTGG---ATAAAGAA-----TTGGATGACTATAGAGAA----G
       :::    ::: :: :   :      ::: :: :       :   ::  : ::  :  ::        :
naip.s AAGGCAAACCCTTCAATCAAGTTTATACAGCAAACCCTCCATTGTCCATGGTCAACAGGG
            4770      4780      4790      4800      4810      4820

4610      4620      4630      4640      4650      4660
naip-o AAAGTGAAGAGTACATGGCTGCTGCTG-ATGAATA---CAATAGACTGAAGCA--AGTGA
       :: :  :: :  ::: :::  ::::      :   ::   : ::    ::    : :  ::::  :    : : :
naip.s AAGGGGTTGGGGACAGGTCTGCCAATCTATCTAAAAGCCACAATATGGAAGAAGTATTCA
            4830      4840      4850      4860      4870      4880

4670      4680      4690      4700
naip-o AGGGATCTGC-AGATTACAAAAGTAA--GAAGAATCA-TTGCAAGCA----------G
       :::::::::::::::::::::::::::::::::::::::::::::::::::::::::
naip.s ATTTATATAATAAATGGCTAACTTAACGGTTGAATCACTTTCATACATGGATGAAACGGG
            4890      4900      4910      4920      4930      4940

4710      4720          4730            4740
naip-o TTAAACAGCAAATTGTCACACATC----------AAGAAGATGGT-----------TGGA
       ::  ::::  ::   ::      :::        :::: ::::  :              ::  :
naip.s TTTAACACAGGATCCACATGAATCTTCTGTGGGCCAAGA-GATGTTCCTTAATCCTTGTA
            4950      4960      4970      4980      4990      5000

4750      4760      4770
naip-o GA---------CTAT---GA--TAG-------ACAGAA-----AACATAGAAGGC--TGA
       ::           :::: ::   :::          ::::  :        :::  ::         :    : :
naip.s GAACCTGTTTTCTATATTGAACTAGCTTTGGTACAGTAGAGTTAACTTACTTTCCATTTA
            5010      5020      5030      5040      5050      5060

4780      4790      4800      4810      4820
naip.o T-----GCCAAGTTGTTTGAGAAA------TTAAGTATC--TGACATCTCTGCAAT--CT
        :     :::::  :           ::::      ::: : :        :::: :: : ::         ::
naip.s TCCACTGCCAATATAAAGAGGAAACAGGGGTTAGGGAAAAATGACTTCATTCCAGAGGCT
            5070      5080      5090      5100      5110      5120

4830      4840      4850      4860      4870
naip-o TCTCAGAAGGCAA---ATG----ACTTTGGACCATAACCCCGGAAGCCAAACCTCTGTGA
       :::::::       :::     ::::     : ::: ::    :   :     :::  :::     :   :: ::
naip.s TCTCAGAGTTCAACATATGCTATAATTTAGAATTTT-CTTATGAATCCACTCTACT-TGG
            5130      5140      5150      5160      5170      5180

4880      4890      4900      4910      4920
naip-o GCATCACAGTTTTGGT------TGCTTTAATATCAT--CAGTATTGAAGCATTTTATAA-
       :  :  :  :     :           ::  ::  ::::  ::   :     ::   :: ::::  :::
naip.s GTAGAAAATATTTTATCTCTAGTGATTGCATATTATTTCCATATCATAGTATTTCATAGT
            5190      5200      5210      5220      5230      5240
```

Fig. 5J

```
           4930           4940          4950           4960
naip-o ATCGCTTTTGATA-----------ATCAAC-----TGGGCTGAA--------CACTCCAAT
       ::   :::::::            :::::     ::  : :::         :  ::: :
naip.s ATTATATTTGATATGAGTGTCTATATCAATGTCAGTGTCCAGAATTTCGTTCCTACCAGT
           5250      5260      5270      5280      5290      5300

4970          4980          4990           5000
naip-o TAAGGA-TTTTATG-----CTTTAAA--CATTGG---TTCTTG-TATTA--AGAA-----
       :::: : :::: ::     :   ::  :::: :   ::: :: :: ::   : ::
naip.s TAAGTAGTTTTCTGAACGGCCAGAAGACCATTCGAAATTCATGATACTACTATAAGTTGG
           5310      5320      5330      5340      5350      5360

5010         5020
naip-o TGAA------ATACTGTT----TGAGGTTTTT-------AAG-------------------
       : ::      :::::  ::    : :  :::  :          :::
naip.s TAAACAACCATACTTTTATCCTCATTTTTATTCTCACTAAGAAAAAAGTCAACTCCCCTC
           5370      5380      5390      5400      5410      5420

5030                       5040     5050           5060
naip-o -CCTT-----------AAA-----GGAAGGT---TCTGGTGTGAACTAAACTTTC----A
       ::::::::::::::::::::::::::::::::::::::::::::::::::::::::::
naip.s CCCTTGCCCAAGTATGAAATATAGGGACAGTATGTATGGTGTGGTCTCATTTGTTTAGAA
           5430      5440      5450      5460      5470      5480

5070        5080         5090         5100
naip-o CACCCCAGACGA-TGTCTTCA-TACCT---ACATGTA-----------TTTGTTTGCATA
       :::  :  :: ::   :  :  ::   ::  ::::            :: : :: :
naip.s AACCACTTATGACTGGGTGCGGTGGCTCACACCTGTAATCCCAGCACTTTGGGAGGCTGA
           5490      5500      5510      5520      5530      5540

5110     5120                                     5130
naip-o GGTGATC---TCATTT---------AAT----------CCTCTC-----------AACCA
       ::  :    :::::::         :::           :::              ::::
naip.s GGCGGGCGAATCATTTGAGGTGAGGAATTCGAGACCAGCCTGGCCAGCATGGTGAAACCC
           5550      5560      5570      5580      5590      5600

5140                              5150     5160    5170
naip-o CCTTTCAGATAAC------------------------TGTTATTTATAATCACTTTTTTCCA---
       :  ::   :::                          :::  :    ::  :: :   :::
naip.s CATCTCTACTAAAAATACAAAAATTAGCCAGGTGTGGTGGCACATGCCTGTAGTCCCAGC
           5610      5620      5630      5640      5650      5660

5180      5190       5200      5210
naip-o CATAAGG-------------AAACTGGGTT---CCTGCAATGAAGTCTCTGAAGTGAA-
       ::  :::             :  ::: ::    ::  :    :   ::    :: :::::
naip.s CACTAGGGCGGCTGAGACGCAAGACTTGCTTGAACCCGGGAGGCAGAGGTTGCAGTGAGC
           5670      5680      5690      5700      5710      5720

5220         5230          5240
naip-o -----------ACTGC-TTGTTTCCT---------AGCAC-ACACTTTTTGGTT------
                  ::::: ::   :::           ::::  ::  :: :  ::
naip.s CAAGATGGCGCCACTGCATTCCAGCCTGGGCAACAGAGCAAGACCCTGTCTGTCTCAAAA
           5730      5740      5750      5760      5770      5780
```

Fig. 5K

```
            5250      5260      5270      5280      5290
naip-o ---------AAGTCTGTTTTATGACTTCATTAATAATAAATTCCGGCATCA--TAC--AG
          ::   :  ::  :::   ::    :   ::  :    ::::  :  ::    :::  ::
naip.s CAAAAAACAAAACCACTTATATTGCTAGCTACATTAAGAATTTCTGAATATGTTACTGAG
          5790      5800      5810      5820      5830      5840

5300                     5310      5320      5330
naip-o CTA-CTCCTC----CC--------TACCGCCACCTCCACAGACACCACTCTCCTGGT---
        ::  ::        ::              ::  :   :    ::::::       :  :
naip.s CTTGCTTGTGGTAACCATTTATAATATCAGAAAGTATATGTACACCAAAA-CATGTTGAA
          5850      5860      5870      5880      5890      5900

5340      5350                              5360
naip-o --TCCATCTCCT-CTGCTGC-------------------TTCTAGCTCC------CTGC
         :::::  :   :  :::                              ::  ::  ::    :::
naip.s CATCCATGTTGTACAACTGAAATATAAATAATTTTGTCAATTATACCTAAATAAAACTGG
          5910      5920      5930      5940      5950      5960

5370               5380      5390      5400
naip-o ---------TCTGGC---TTCA---------AGGTGCGCAGGACCTGCTTCCTTG--GTGA
                :::::    ::  :              : ::    ::   :  :  ::         :
naip.s AAAAAAATTTCTGGAAGTTTATATCTAAAAATGTTAATAGTGCGTACCTCTAGGAAGTGG
          5970      5980      5990      6000      6010      6020

5410      5420      5430      5440      5450      5460
naip-o TCCTCTGTAGTCTCCCACACCCCACATTATCTACAAA-CTGA--TGACTCCTAATTTACA
        :::   :  ::  :     :   ::      ::  :  :::  :  :    :::      ::   :    :   ::::
naip.s GCCTG-GAAGCCATTCTTACTTTTCAGTCTCTCCCATTCTGTACTGTTTTTTGTTTTACT
          6030      6040      6050      6060      6070

5470      5480      5490            5500
naip-o TCT---CCAGC-TCAGACCTCTCCATCAATCCCAACGCA---TA------CAC-
        :     ::  ::  :   :       :::        :  ::  :    ::        ::       :::
naip.s TTCGTGCCTGCATTATTTTTCTATTTAAAACAAAAATAAATCTAGTTTAGCACT
          6080      6090      6100      6110      6120      6130
```

Fig. 5L

```
     ACAAAAGGTCCTGTGCTCACCTGGGACCCTTCTGGACGTTGCCCTGTGTACCTCTTCGAC
1    ------------+---------+---------+---------+---------+---------+  60
     TGTTTTCCAGGACACGAGTGGACCCTGGGAAGACCTGCAACGGGACACATGGAGAAGCTG

TGCCTGTTCATCTACGACGAACCCCGGGTATTGACCCCAGACAACAATGCCACTTCATAT
61   ------------+---------+---------+---------+---------+---------+  120
     ACGGACAAGTAGATGCTGCTTGGGGCCCATAACTGGGGTCTGTTGTTACGGTGAAGTATA

TGGGGACTTCGTCTGGGATTCCAAGGTGCATTCATTGCAAAGTTCCTTAAATATTTTCTC
121  ------------+---------+---------+---------+---------+---------+  180
     ACCCCTGAAGCAGACCCTAAGGTTCCACGTAAGTAACGTTTCAAGGAATTTATAAAAGAG

ACTGCTTCCTACTAAAGGACGGACAGAGCATTTGTTCTTCAGCCACATACTTTCCTTCCA
181  ------------+---------+---------+---------+---------+---------+  240
     TGACGAAGGATGATTTCCTGCCTGTCTCGTAAACAAGAAGTCGGTGTATGAAAGGAAGGT

CTGGCCAGCATTCTCCTCTATTAGACTAGAACTGTGGATAAACCTCAGAAAATGGCCACC
241  ------------+---------+---------+---------+---------+---------+  300
     GACCGGTCGTAAGAGGAGATAATCTGATCTTGACACCTATTTGGAGTCTTTTACCGGTGG
                                                       M  A  T     3

CAGCAGAAAGCCTCTGACGAGAGGATCTCCCAGTTTGATCACAATTTGCTGCCAGAGCTG
301  ------------+---------+---------+---------+---------+---------+  360
     GTCGTCTTTCGGAGACTGCTCTCCTAGAGGGTCAAACTAGTGTTAAACGACGGTCTCGAC
  4  Q  Q  K  A  S  D  E  R  I  S  Q  F  D  H  N  L  L  P  E  L     23

TCTGCTCTTCTGGGCCTAGATGCAGTTCAGTTGGCAAAGGAACTAGAAGAAGAGGAGCAG
361  ------------+---------+---------+---------+---------+---------+  420
     AGACGAGAAGACCCGGATCTACGTCAAGTCAACCGTTTCCTTGATCTTCTTCTCCTCGTC
 24  S  A  L  L  G  L  D  A  V  Q  L  A  K  E  L  E  E  E  E  Q     43

AAGGAGCGAGCAAAAATGCAGAAAGGCTACAACTCTCAAATGCGCAGTGAAGCAAAAAGG
421  ------------+---------+---------+---------+---------+---------+  480
     TTCCTCGCTCGTTTTTACGTCTTTCCGATGTTGAGAGTTTACGCGTCACTTCGTTTTTCC
 44  K  E  R  A  K  M  Q  K  G  Y  N  S  Q  M  R  S  E  A  K  R     63

TTAAAGACTTTTGTGACTTATGAGCCGTACAGCTCATGGATACCACAGGAGATGGCGGCC
481  ------------+---------+---------+---------+---------+---------+  540
     AATTTCTGAAAACACTGAATACTCGGCATGTCGAGTACCTATGGTGTCCTCTACCGCCGG
 64  L  K  T  F  V  T  Y  E  P  Y  S  S  W  I  P  Q  E  M  A  A     83

GCTGGGTTTTACTTCACTGGGGTAAAATCTGGGATTCAGTGCTTCTGCTGTAGCCTAATC
541  ------------+---------+---------+---------+---------+---------+  600
     CGACCCAAAATGAAGTGACCCCATTTTAGACCCTAAGTCACGAAGACGACATCGGATTAG
 84  A  G  F  Y  F  T  G  V  K  S  G  I  Q  C  F  C  C  S  L  I     103

CTCTTTGGTGCCGGCCTCACGAGACTCCCCATAGAAGACCACAAGAGGTTTCATCCAGAT
601  ------------+---------+---------+---------+---------+---------+  660
     GAGAAACCACGGCCGGAGTGCTCTGAGGGGTATCTTCTGGTGTTCTCCAAAGTAGGTCTA
104  L  F  G  A  G  L  T  R  L  P  I  E  D  H  K  R  F  H  P  D     123
```

Fig. 6A

```
                TGTGGGTTCCTTTTGAACAAGGATGTTGGTAACATTGCCAAGTACGACATAAGGGTGAAG
661             ------------+---------+---------+---------+---------+---------+ 720
                ACACCCAAGGAAAACTTGTTCCTACAACCATTGTAACGGTTCATGCTGTATTCCCACTTC
124             C  G  F  L  L  N  K  D  V  G  N  I  A  K  Y  D  I  R  V  K   143

AATCTGAAGAGCAGGCTGAGAGGAGGTAAAATGAGGTACCAAGAAGAGGAGGCTAGACTT
721             ------------+---------+---------+---------+---------+---------+ 780
                TTAGACTTCTCGTCCGACTCTCCTCCATTTTACTCCATGGTTCTTCTCCTCCGATCTGAA
144             N  L  K  S  R  L  R  G  G  K  M  R  Y  Q  E  E  A  R  L   163

GCGTCCTTCAGGAACTGGCCATTTTATGTCCAAGGGATATCCCCTTGTGTGCTCTCAGAG
781             ------------+---------+---------+---------+---------+---------+ 840
                CGCAGGAAGTCCTTGACCGGTAAAATACAGGTTCCCTATAGGGGAACACACGAGAGTCTC
164             A  S  F  R  N  W  P  F  Y  V  Q  G  I  S  P  C  V  L  S  E   183

GCTGGCTTTGTCTTTACAGGTAAACAGGACACGGTACAGTGTTTTTCCTGTGGTGGATGT
841             ------------+-------⋈-+---------+---------+---------+---------+ 900
                CGACCGAAACAGAAATGTCCATTTGTCCTGTGCCATGTCACAAAAAGGACACCACCTACA
184             A  G  F  V  F  T  G  K  Q  D  T  V  Q  C  F  S  -C- G  G  C  203

TTAGGAAATTGGGAAGAAGGAGATGATCCTTGGAAGGAACATGCCAAATGGTTCCCCAAA
901             ------------+---------+---------+---------+---------+------⋈--+ 960
                AATCCTTTAACCCTTCTTCCTCTACTAGGAACCTTCCTTGTACGGTTTACCAAGGGGTTT
204             L  G  N  W  E  E  G  D  D  P  W  K  E  H  A  K  W  F  P  K  223

TGTGAATTTCTTCGGAGTAAGAAAATCCTCAGAGGAAATTACCCAGTATATTCAAAGCTAC
961             ------------+---------+---------+---------+---------+---------+ 1020
                ACACTTAAAGAAGCCTCATTCTTTAGGAGTCTCCTTTAATGGGTCATATAAGTTTCGATG
224             C  E  F  L  R  S  K  K  S  E  E  I  T  Q  Y  I  Q  S  Y   243
                      6 7
                AAGGGATTTGTTGACATAACGGGAGAACATTTTGTGAATTCCTGGGTCCAGAGAGAATTA
1021            ------------+-------⋈-+---------+---------+---------+---------+ 1080
                TTCCCTAAACAACTGTATTGCCCTCTTGTAAAACACTTAAGGACCCAGGTCTCTCTTAAT
244             K  G  F  V  D  I  T  G  E  H  F  V  N  S  W  V  Q  R  E  L  263
                      7 8
                CCTATGGCATCAGCTTATTGCAATGACAGCATCTTTGCTTACGAAGAACTACGGCTGGAC
1081            ------------+---------+---------+---------+---------+---------+ 1140
                GGATACCGTAGTCGAATAACGTTACTGTCGTAGAAACGAATGCTTCTTGATGCCGACCTG
264             P  M  A  S  A  Y  C  N  D  S  I  F  A  Y  E  E  L  R  L  D  283

TCTTTTAAGGACTGGCCCCGGGAATCAGCTGTGGGAGTTGCAGCACTGGCCAAAGCAGGT
1141            ------------+---------+---------+---------+---------+---------+ 1200
                AGAAAATTCCTGACCGGGGCCCTTAGTCGACACCCTCAACGTCGTGACCGGTTTCGTCCA
284             S  F  K  D  W  P  R  E  S  A  V  G  V  A  A  L  A  K  A  G   303

CTTTTCTACACAGGTATAAAGGACATCGTCCAGTGCTTTTCCTGTGGAGGGTGTTTAGAG
1201            ------------+-------⋈-+---------+---------+---------+---------+ 1260
                GAAAAGATGTGTCCATATTTCCTGTAGCAGGTCACGAAAAGGACACCTCCCACAAATCTC
304             L  F  Y  T  G  I  K  D  I  V  Q  C  F  S  C  G  G  C  L  E   323
                      910
                AAATGGCAGGAAGGTGATGACCCATTAGACGATCACACCAGATGTTTTCCCAATTGTCCA
1261            ------------+---------+---------+---------+---------+---------+ 1320
                TTTACCGTCCTTCCACTACTGGGTAATCTGCTAGTGTGGTCTACAAAAGGGTTAACAGGT
324             K  W  Q  E  G  D  D  P  L  D  D  H  T  R  C  F  P  N  C  P   343
```

Fig. 6B

```
            TTTCTCCAAAATATGAAGTCCTCTGCGGAAGTGACTCCAGACCTTCAGAGCCGTGGTGAA
1321   ---------+---------+---------+---------+---------+---------+ 1380
            AAAGAGGTTTTATACTTCAGGAGACGCCTTCACTGAGGTCTGGAAGTCTCGGCACCACTT
344    F   L   Q   N   M   K   S   S   A   E   V   T   P   D   L   Q   S   R   G   E   363

CTTTGTGAATTACTGGAAACCACAAGTGAAAGCAATCTTGAAGATTCAATAGCAGTTGGT
1381   ---------+---------+---------+---------+---------+---------+ 1440
            GAAACACTTAATGACCTTTGGTGTTCACTTTCGTTAGAACTTCTAAGTTATCGTCAACCA
364    L   C   E   L   L   E   T   T   S   E   S   N   L   E   D   S   I   A   V   G   383

CCTATAGTGCCAGAAATGGCACAGGGTGAAGCCCAGTGGTTTCAAGAGGCAAAGAATCTG
1441   ---------+---------+---------+---------+---------+---------+ 1500
            GGATATCACGGTCTTTACCGTGTCCCACTTCGGGTCACCAAAGTTCTCCGTTTCTTAGAC
384    P   I   V   P   E   M   A   Q   G   E   A   Q   W   F   Q   E   A   K   N   L   403

AATGAGCAGCTGAGAGCAGCTTATACCAGCGCCAGTTTCCGCCACATGTCTTTGCTTGAT
1501   ---------+---------+---------+---------+---------+---------+ 1560
            TTACTCGTCGACTCTCGTCGAATATGGTCGCGGTCAAAGGCGGTGTACAGAAACGAACTA
404    N   E   Q   L   R   A   A   Y   T   S   A   S   F   R   H   M   S   L   L   D   423

ATCTCTTCCGATCTGGCCACGGACCACTTGCTGGGCTGTGATCTGTCTATTGCTTCAAAA
1561   ---------+---------+---------+---------+---------+---------+ 1620
            TAGAGAAGGCTAGACCGGTGCCTGGTGAACGACCCGACACTAGACAGATAACGAAGTTTT
424    I   S   S   D   L   A   T   D   H   L   L   G   C   D   L   S   I   A   S   K   443

CACATCAGCAAACCTGTGCAAGAACCTCTGGTGCTGCCTGAGGTCTTTGGCAACTTGAAC
1621   ---------+---------+---------+---------+---------+---------+ 1680
            GTGTAGTCGTTTGGACACGTTCTTGGAGACCACGACGGACTCCAGAAACCGTTGAACTTG
444    H   I   S   K   P   V   Q   E   P   L   V   L   P   E   V   F   G   N   L   N   463

TCTGTCATGTGTGTGGAGGGTGAAGCTGGAAGTGGAAAGACGGTCCTCCTGAAGAAAATA
1681   ---------+---------+---------+---------+---------+---------+ 1740
            AGACAGTACACACACCTCCCACTTCGACCTTCACCTTTCTGCCAGGAGGACTTCTTTTAT
464    S   V   M   C   V   E   G   E   A   G   S   G   K   T   V   L   L   K   K   I   483

GCTTTTCTGTGGGCATCTGGATGCTGTCCCCTGTTAAACAGGTTCCAGCTGGTTTTCTAC
1741   ---------+---------+---------+---------+---------+---------+ 1800
            CGAAAAGACACCCGTAGACCTACGACAGGGGACAATTTGTCCAAGGTCGACCAAAAGATG
484    A   F   L   W   A   S   G   C   C   P   L   L   N   R   F   Q   L   V   F   Y   503

CTCTCCCTTAGTTCCACCAGACCAGACGAGGGGCTGGCCAGTATCATCTGTGACCAGCTC
1801   ---------+---------+---------+---------+---------+---------+ 1860
            GAGAGGGAATCAAGGTGGTCTGGTCTGCTCCCCGACCGGTCATAGTAGACACTGGTCGAG
504    L   S   L   S   S   T   R   P   D   E   G   L   A   S   I   I   C   D   Q   L   523

CTAGAGAAAGAAGGATCTGTTACTGAAATGTGCATGAGGAACATTATCCAGCAGTTAAAG
1861   ---------+---------+---------+---------+---------+---------+ 1920
            GATCTCTTTCTTCCTAGACAATGACTTTACACGTACTCCTTGTAATAGGTCGTCAATTTC
524    L   E   K   E   G   S   V   T   E   M   C   M   R   N   I   I   Q   Q   L   K   543

AATCAGGTCTTATTCCTTTTAGATGACTACAAAGAAATATGTTCAATCCCTCAAGTCATA
1921   ---------+---------+---------+---------+---------+---------+ 1980
            TTAGTCCAGAATAAGGAAAATCTACTGATGTTTCTTTATACAAGTTAGGGAGTTCAGTAT
544    N   Q   V   L   F   L   L   D   D   Y   K   E   I   C   S   I   P   Q   V   I   563
```

Fig. 6C

```
              GGAAAACTGATTCAAAAAAACCACTTATCCCGGACCTGCCTATTGATTGCTGTCCGTACA
1981     ---------+---------+---------+---------+---------+---------+   2040
              CCTTTTGACTAAGTTTTTTTGGTGAATAGGGCCTGGACGGATAACTAACGAC AGGCATGT
564      G  K  L  I  Q  K  N  H  L  S  R  T  C  L  L  I  A  V  R  T      583

AACAGGGCCAGGGACATCCGCCGATACCTAGAGACCATTCTAGAGATCAAAGCATTTCCC
2041     ---------+---------+---------+---------+---------+---------+   2100
              TTGTCCCGGTCCCTGTAGGCGGCTATGGATCTCTGGTAAGATCTCTAGTTTCGTAAAGGG
584      N  R  A  R  D  I  R  R  Y  L  E  T  I  L  E  I  K  A  F  P      603

TTTTATAATACTGTCTGTATATTACGGAAGCTCTTTTCACATAATATGACTCGTCTGCGA
2101     ---------+---------+---------+---------+---------+---------+   2160
              AAAATATTATGACAGACATATAATGCCTTCGAGAAAAGTGTATTATACTGAGCAGACGCT
604      F  Y  N  T  V  C  I  L  R  K  L  F  S  H  M  T  R  L  R        623

AAGTTTATGGTTTACTTTGGAAAGAACCAAAGTTTGCAGAAGATACAGAAAACTCCTCTC
2161     ---------+---------+---------+---------+---------+---------+   2220
              TTCAAATACCAAATGAAACCTTTCTTGGTTTCAAACGTCTTCTATGTCTTTTGAGGAGAG
624      K  F  M  V  Y  F  G  K  N  Q  S  L  Q  K  I  Q  K  T  P  L      643

TTTGTGGCGGCGATCTGTGCTCATTGGTTTCAGTATCCTTTTGACCCATCCTTTGATGAT
2221     ---------+---------+---------+---------+---------+---------+   2280
              AAACACCGCCGCTAGACACGAGTAACCAAAGTCATAGGAAAACTGGGTAGGAAACTACTA
644      F  V  A  A  I  C  A  H  W  F  Q  Y  P  F  D  P  S  F  D  D      663

GTGGCTGTTTTCAAGTCCTATATGGAACGCCTTTCCTTAAGGAACAAAGCGACAGCTGAA
2281     ---------+---------+---------+---------+---------+---------+   2340
              CACCGACAAAAGTTCAGGATATACCTTGCGGAAAGGAATTCCTTGTTTCGCTGTCGACTT
664      V  A  V  F  K  S  Y  M  E  R  L  S  L  R  N  K  A  T  A  E      683

ATTCTCAAAGCAACTGTGTCCTCCTGTGGTGAGCTGGCCTTGAAAGGGTTTTTTTCATGT
2341     ---------+---------+---------+---------+---------+---------+   2400
              TAAGAGTTTCGTTGACACAGGAGGACACCACTCGACCGGAACTTTCCCAAAAAAAGTACA
684      I  L  K  A  T  V  S  S  C  G  E  L  A  L  K  G  F  F  S  C      703

TGCTTTGAGTTTAATGATGATGATCTCGCAGAAGCAGGGGTTGATGAAGATGAAGATCTA
2401     ---------+---------+---------+---------+---------+---------+   2460
              ACGAAACTCAAATTACTACTACTAGAGCGTCTTCGTCCCCAACTACTTCTACTTCTAGAT
704      C  F  E  F  N  D  D  D  L  A  E  A  G  V  D  E  D  E  D  L      723

ACCATGTGCTTGATGAGCAAATTTACAGCCCAGAGACTAAGACCATTCTACCGGTTTTTA
2461     ---------+---------+---------+---------+---------+---------+   2520
              TGGTACACGAACTACTCGTTTAAATGTCGGGTCTCTGATTCTGGTAAGATGGCCAAAAAT
724      T  M  C  L  M  S  K  F  T  A  Q  R  L  R  P  F  Y  R  F  L      743

AGTCCTGCCTTCCAAGAATTTCTTGCGGGGATGAGGCTGATTGAACTCCTGGATTCAGAT
2521     ---------+---------+---------+---------+---------+---------+   2580
              TCAGGACGGAAGGTTCTTAAAGAACGCCCCTACTCCGACTAACTTGAGGACCTAAGTCTA
744      S  P  A  F  Q  E  F  L  A  G  M  R  L  I  E  L  L  D  S  D      763

AGGCAGGAACATCAAGATTTGGGACTGTATCATTTGAAACAAATCAACTCACCCATGATG
2581     ---------+---------+---------+---------+---------+---------+   2640
              TCCGTCCTTGTAGTTCTAAACCCTGACATAGTAAACTTTGTTTAGTTGAGTGGGTACTAC
764      R  Q  E  H  Q  D  L  G  L  Y  H  L  K  Q  I  N  S  P  M  M      783
```

Fig. 6D

```
         ACTGTAAGCGCCTACAACAATTTTTTGAACTATGTCTCCAGCCTCCCTTCAACAAAAGCA
2641   ---------+---------+---------+---------+---------+---------+   2700
         TGACATTCGCGGATGTTGTTAAAAAACTTGATACAGAGGTCGGAGGGAAGTTGTTTTCGT
 784   T  V  S  A  Y  N  N  F  L  N  Y  V  S  S  L  P  S  T  K  A      803

GGGCCCAAAATTGTGTCTCATTTGCTCCATTTAGTGGATAACAAAGAGTCATTGGAGAAT
2701   ---------+---------+---------+---------+---------+---------+   2760
         CCCGGGTTTTAACACAGAGTAAACGAGGTAAATCACCTATTGTTTCTCAGTAACCTCTTA
 804   G  P  K  I  V  S  H  L  L  H  L  V  D  N  K  E  S  L  E  N      823

ATATCTGAAAATGATGACTACTTAAAGCACCAGCCAGAAATTTCACTGCAGATGCAGTTA
2761   ---------+---------+---------+---------+---------+---------+   2820
         TATAGACTTTTACTACTGATGAATTTCGTGGTCGGTCTTTAAAGTGACGTCTACGTCAAT
 824   I  S  E  N  D  D  Y  L  K  H  Q  P  E  I  S  L  Q  M  Q  L      843

CTTAGGGGATTGTGGCAAATTTGTCCACAAGCTTACTTTTCAATGGTTTCAGAACATTTA
2821   ---------+---------+---------+---------+---------+---------+   2880
         GAATCCCCTAACACCGTTTAAACAGGTGTTCGAATGAAAAGTTACCAAAGTCTTGTAAAT
 844   L  R  G  L  W  Q  I  C  P  Q  A  Y  F  S  M  V  -S  E  H  L      863

CTGGTTCTTGCCCTGAAAACTGCTTATCAAAGCAACACTGTTGCTGCGTGTTCTCCATTT
2881   ---------+---------+---------+---------+---------+---------+   2940
         GACCAAGAACGGGACTTTTGACGAATAGTTTCGTTGTGACAACGACGCACAAGAGGTAAA
 864   L  V  L  A  L  K  T  A  Y  Q  S  N  T  V  A  A  C  S  P  F      883

GTTTTGCAATTCCTTCAAGGGAGAACACTGACTTTGGGTGCGCTTAACTTACAGTACTTT
2941   ---------+---------+---------+---------+---------+---------+   3000
         CAAAACGTTAAGGAAGTTCCCTCTTGTGACTGAAACCCACGCGAATTGAATGTCATGAAA
 884   V  L  Q  F  L  Q  G  R  T  L  T  L  G  A  L  N  L  Q  Y  F      903

TTCGACCACCCAGAAAGCTTGTCATTGTTGAGGAGCATCCACTTCCCAATACGAGGAAAT
3001   ---------+---------+---------+---------+---------+---------+   3060
         AAGCTGGTGGGTCTTTCGAACAGTAACAACTCCTCGTAGGTGAAGGGTTATGCTCCTTTA
 904   F  D  H  P  E  S  L  S  L  L  R  S  I  H  F  P  I  R  G  N      923

AAGACATCACCCAGAGCACATTTTTCAGTTCTGGAAACATGTTTTGACAAATCACAGGTG
3061   ---------+---------+---------+---------+---------+---------+   3120
         TTCTGTAGTGGGTCTCGTGTAAAAAGTCAAGACCTTTGTACAAAACTGTTTAGTGTCCAC
 924   K  T  S  P  R  A  H  F  S  V  L  E  T  C  F  D  K  S  Q  V      943

CCAACTATAGATCAGGACTATGCTTCTGCCTTTGAACCTATGAATGAATGGGAGCGAAAT
3121   ---------+---------+---------+---------+---------+---------+   3180
         GGTTGATATCTAGTCCTGATACGAAGACGGAAACTTGGATACTTACTTACCCTCGCTTTA
 944   P  T  I  D  Q  D  Y  A  S  A  F  E  P  M  N  E  W  E  R  H      963

TTAGCTGAAAAAGAGGATAATGTAAAGAGCTATATGGATATGCAGCGCAGGGCATCACCA
3181   ---------+---------+---------+---------+---------+---------+   3240
         AATCGACTTTTTCTCCTATTACATTTCTCGATATACCTATACGTCGCGTCCCGTAGTGGT
 964   L  A  E  K  E  D  N  V  K  S  Y  M  D  M  Q  R  R  A  S  P      983

GACCTTAGTACTGGCTATTGGAAACTTTCTCCAAAGCAGTACAAGATTCCCTGTCTAGAA
3241   ---------+---------+---------+---------+---------+---------+   3300
         CTGGAATCATGACCGATAACCTTTGAAAGAGGTTTCGTCATGTTCTAAGGGACAGATCTT
 984   D  L  S  T  G  Y  W  K  L  S  P  K  Q  Y  K  I  P  C  L  E     1003
```

Fig. 6E

```
      GTCGATGTGAATGATATTGATGTTGTAGGCCAGGATATGCTTGAGATTCTAATGACAGTT
3301  ------------+---------+---------+---------+---------+---------+  3360
      CAGCTACACTTACTATAACTACAACATCCGGTCCTATACGAACTCTAAGATTACTGTCAA
1004  V  D  V  N  D  I  D  V  V  G  Q  D  M  L  E  I  L  M  T  V   1023

TTCTCAGCTTCACAGCGCATCGAACTCCATTTAAACCACAGCAGAGGCTTTATAGAAAGC
3361  ------------+---------+---------+---------+---------+---------+  3420
      AAGAGTCGAAGTGTCGCGTAGCTTGAGGTAAATTTGGTGTCGTCTCCGAAATATCTTTCG
1024  F  S  A  S  Q  R  I  E  L  H  L  N  H  S  R  G  F  I  E  S   1043

ATCCGCCCAGCTCTTGAGCTGTCTAAGGCCTCTGTCACCAAGTGCTCCATAAGCAAGTTG
3421  ------------+---------+---------+---------+---------+---------+  3480
      TAGGCGGGTCGAGAACTCGACAGATTCCGGAGACAGTGGTTCACGAGGTATTCGTTCAAC
1044  I  R  P  A  L  E  L  S  K  A  S  V  T  K  C  S  I  S  K  L   1063

GAACTCAGCGCAGCCGAACAGGAACTGCTTCTCACCCTGCCTTCCCTGGAATCTCTTGAA
3481  ------------+---------+---------+---------+---------+---------+  3540
      CTTGAGTCGCGTCGGCTTGTCCTTGACGAAGAGTGGGACGGAAGGGACCTTAGAGAACTT
1064  E  L  S  A  A  E  Q  E  L  L  L  T  P  S  L  E  S  L  E   1083
                                                12    13

GTCTCAGGGACAATCCAGTCACAAGACCAAATCTTTCCTAATCTGGATAAGTTCCTGTGC
3541  ------------+---------+---------+---------+---------+---------+  3600
      CAGAGTCCCTGTTAGGTCAGTGTTCTGGTTTAGAAAGGATTAGACCTATTCAAGGACACG
1084  V  S  G  T  I  Q  S  Q  D  Q  I  F  P  N  L  D  K  F  L  C   1103

CTGAAAGAACTGTCTGTGGATCTGGAGGGCAATATAAATGTTTTTTCAGTCATTCCTGAA
3601  ------------+---------+---------+---------+---------+---------+  3660
      GACTTTCTTGACAGACACCTAGACCTCCCGTTATATTTACAAAAAAGTCAGTAAGGACTT
1104  L  K  E  L  S  V  D  L  E  G  N  I  N  V  F  S  V  I  P  E   1123

GAATTTCCAAACTTCCACCATATGGAGAAATTATTGATCCAAATTTCAGCTGAGTATGAT
3661  ------------+---------+---------+---------+---------+---------+  3720
      CTTAAAGGTTTGAAGGTGGTATACCTCTTTAATAACTAGGTTTAAAGTCGACTCATACTA
1124  E  F  P  N  F  H  H  M  E  K  L  L  I  Q  I  S  A  E  Y  D   1143

CCTTCCAAACTAGTAAAATTAATTCAAAATTCTCCAAACCTTCATGTTTTCCATCTGAAG
3721  ------------+---------+---------+---------+---------+---------+  3780
      GGAAGGTTTGATCATTTTAATTAAGTTTTAAGAGGTTTGGAAGTACAAAAGGTAGACTTC
1144  P  S  K  L  V  K  L  I  Q  N  S  P  N  L  H  V  F  H  L  K   1163

TGTAACTTCTTTTCGGATTTTGGGTCTCTCATGACTATGCTTGTTTCCTGTAAGAAACTC
3781  ------------+---------+---------+---------+---------+---------+  3840
      ACATTGAAGAAAAGCCTAAAACCCAGAGAGTACTGATACGAACAAAGGACATTCTTTGAG
1164  C  N  F  F  S  D  F  G  S  L  M  T  M  L  V  S  C  K  K  L   1183

ACAGAAATTAAGTTTTCGGATTCATTTTTTCAAGCCGTCCCATTTGTTGCCAGTTTGCCA
3841  ------------+---------+---------+---------+---------+---------+  3900
      TGTCTTTAATTCAAAAGCCTAAGTAAAAAAGTTCGGCAGGGTAAACAACGGTCAAACGGT
1184  T  E  I  K  F  S  D  S  F  F  Q  A  V  P  F  V  A  S  L  P   1203

AATTTTATTTCTCTGAAGATATTAAATCTTGAAGGCCAGCAATTTCCTGATGAGGAAACA
3901  ------------+---------+---------+---------+---------+---------+  3960
      TTAAAATAAAGAGACTTCTATAATTTAGAACTTCCGGTCGTTAAAGGACTACTCCTTTGT
1204  N  F  I  S  L  K  I  L  N  L  E  G  Q  Q  F  P  D  E  E  T   1223
```

Fig. 6F

```
      TCAGAAAAATTTGCCTACATTTTAGGTTCTCTTAGTAACCTGGAAGAATTGATCCTTCCT
3961  ------------+----------+----------+----------+----------+----------+  4020
      AGTCTTTTTAAACGGATGTAAAATCCAAGAGAATCATTGGACCTTCTTAACTAGGAAGGA
1224  S  E  K  F  A  Y  I  L  G  S  L  S  N  L  E  E  L  I  L  P   1243

ACTGGGGATGGAATTTATCGAGTGGCCAAACTGATCATCCAGCAGTGTCAGCAGCTTCAT
4021  ------------+----------+----------+----------+----------+----------+  4080
      TGACCCCTACCTTAAATAGCTCACCGGTTTGACTAGTAGGTCGTCACAGTCGTCGAAGTA
1244  T  G  D  G  I  Y  R  V  A  K  L  I  I  Q  Q  C  Q  Q  L  H   1263
             16 17
      TGTCTCCGAGTCCTCTCATTTTTCAAGACTTTGAATGATGACAGCGTGGTGGAAATTGCC
4081  ------------+----------+----------+----------+----------+----------+  4140
      ACAGAGGCTCAGGAGAGTAAAAAGTTCTGAAACTTACTACTGTCGCACCACCTTTAACGG
1264  C  L  R  V  L  S  F  F  K  T  L  N  D  D  S  V  V  E  I  A   1283

AAAGTAGCAATCAGTGGAGGTTTCCAGAAACTTGAGAACCTAAAGCTTTCAATCAATCAC
4141  ------------+----------+----------+----------+----------+----------+  4200
      TTTCATCGTTAGTCACCTCCAAAGGTCTTTGAACTCTTGGATTTCGAAAGTTAGTTAGTG
1284  K  V  A  I  S  G  G  F  Q  K  L  E  N  L  K  L  S  I  N  H   1303

AAGATTACAGAGGAAGGATACAGAAATTTCTTTCAAGCACTGGACAACATGCCAAACTTG
4201  ------------+----------+----------+----------+----------+----------+  4260
      TTCTAATGTCTCCTTCCTATGTCTTTAAAGAAAGTTCGTGACCTGTTGTACGGTTTGAAC
1304  K  I  T  E  E  G  Y  R  N  F  F  Q  A  L  D  N  M  P  N  L   1323

CAGGAGTTGGACATCTCCAGGCATTTCACAGAGTGTATCAAAGCTCAGGCCACAACAGTC
4261  ------------+----------+----------+----------+----------+----------+  4320
      GTCCTCAACCTGTAGAGGTCCGTAAAGTGTCTCACATAGTTTCGAGTCCGGTGTTGTCAG
1324  Q  E  L  D  I  S  R  H  F  T  E  C  I  K  A  Q  A  T  T  V   1343

AAGTCTTTGAGTCAATGTGTGTTACGACTACCAAGGCTCATTAGACTGAACATGTTAAGT
4321  ------------+----------+----------+----------+----------+----------+  4380
      TTCAGAAACTCAGTTACACACAATGCTGATGGTTCCGAGTAATCTGACTTGTACAATTCA
1344  K  S  L  S  Q  C  V  L  R  L  P  R  L  I  R  L  N  M  L  S   1363

TGGCTCTTGGATGCAGATGATATTGCATTGCTTAATGTCATGAAAGAAAGACATCCTCAA
4381  ------------+----------+----------+----------+----------+----------+  4440
      ACCGAGAACCTACGTCTACTATAACGTAACGAATTACAGTACTTTCTTTCTGTAGGAGTT
1364  W  L  L  D  A  D  D  I  A  L  L  N  V  M  K  E  R  H  P  Q   1383

TCTAAGTACTTAACTATTCTCCAGAAATGGATACTGCCGTTCTCTCCAATCATTCAGAAA
4441  ------------+----------+----------+----------+----------+----------+  4500
      AGATTCATGAATTGATAAGAGGTCTTTACCTATGACGGCAAGAGAGGTTAGTAAGTCTTT
1384  S  K  Y  L  T  I  L  Q  K  W  I  L  P  F  S  P  I  I  Q  K   1403

TAAAAGATTCAGCTAAAAACTGCTGAATCAATAATTTGTCTTGGGGCATATTGAGGATGT
4501  ------------+----------+----------+----------+----------+----------+  4560
      ATTTTCTAAGTCGATTTTTGACGACTTAGTTATTAAACAGAACCCCGTATAACTCCTACA
1404  *                                                              1423

AAAAAAAGTTGTTGATTAATGCTAAAAACCAAATTATCCAAAATTATTTTATTAAATATT
4561  ------------+----------+----------+----------+----------+----------+  4620
      TTTTTTTCAACAACTAATTACGATTTTTGGTTTAATAGGTTTTAATAAAATAATTTATAA
```

Fig. 6G

```
       GCATACAAAAGAAAATGTGTAAGGCTTGCTAAAAAACAAAACAAAACAAAACACAGTCCT
4621   ------------+---------+---------+---------+---------+---------+  4680
       CGTATGTTTTCTTTTACACATTCCGAACGATTTTTTGTTTTGTTTTGTTTGTGTCAGGA

GCATACTCACCACCAAGCTCAAGAAATAAATCATCACCAATACCTTTGAGGTCCCTGAGT
4681   ------------+---------+---------+---------+---------+---------+  4740
       CGTATGAGTGGTGGTTCGAGTTCTTTATTTAGTAGTGGTTATGGAAACTCCAGGGACTCA

AATCCACCCCAGCTAAAGGCAAACCCTTCAATCAAGTTTATACAGCAAACCCTCCATTGT
4741   ------------+---------+---------+---------+---------+---------+  4800
       TTAGGTGGGGTCGATTTCCGTTTGGGAAGTTAGTTCAAATATGTCGTTTGGGAGGTAACA

CCATGGTCAACAGGGAAGGGGTTGGGGACAGGTCTGCCAATCTATCTAAAAGCCACAATA
4801   ------------+---------+---------+---------+---------+---------+  4860
       GGTACCAGTTGTCCCTTCCCCAACCCCTGTCCAGACGGTTAGATAGATTTTCGGTGTTAT

TGGAAGAAGTATTCAATTTATATAATAAATGGCTAACTTAACGGTTGAATCACTTTCATA
4861   ------------+---------+---------+---------+---------+---------+  4920
       ACCTTCTTCATAAGTTAAATATATTATTTACCGATTGAATTGCCAACTTAGTGAAAGTAT

CATGGATGAAACGGGTTTAACACAGGATCCACATGAATCTTCTGTGGGCCAAGAGATGTT
4921   ------------+---------+---------+---------+---------+---------+  4980
       GTACCTACTTTGCCCAAATTGTGTCCTAGGTGTACTTAGAAGACACCCGGTTCTCTACAA

CCTTAATCCTTGTAGAACCTGTTTTCTATATTGAACTAGCTTTGGTACAGTAGAGTTAAC
4981   ------------+---------+---------+---------+---------+---------+  5040
       GGAATTAGGAACATCTTGGACAAAAGATATAACTTGATCGAAACCATGTCATCTCAATTG

TTACTTTCCATTTATCCACTGCCAATATAAAGAGGAAACAGGGGTTAGGGAAAAATGACT
5041   ------------+---------+---------+---------+---------+---------+  5100
       AATGAAAGGTAAATAGGTGACGGTTATATTTCTCCTTTGTCCCCAATCCCTTTTTACTGA

TCATTCCAGAGGCTTCTCAGAGTTCAACATATGCTATAATTTAGAATTTTCTTATGAATC
5101   ------------+---------+---------+---------+---------+---------+  5160
       AGTAAGGTCTCCGAAGAGTCTCAAGTTGTATACGATATTAAATCTTAAAAGAATACTTAG

CACTCTACTTGGGTAGAAAATATTTTATCTCTAGTGATTGCATATTATTTCCATATCATA
5161   ------------+---------+---------+---------+---------+---------+  5220
       GTGAGATGAACCCATCTTTTATAAAATAGAGATCACTAACGTATAATAAAGGTATAGTAT

GTATTTCATAGTATTATATTTGATATGAGTGTCTATATCAATGTCAGTGTCCAGAATTTC
5221   ------------+---------+---------+---------+---------+---------+  5280
       CATAAAGTATCATAATATAAACTATACTCACAGATATAGTTACAGTCACAGGTCTTAAAG

GTTCCTACCAGTTAAGTAGTTTTCTGAACGGCCAGAAGACCATTCGAAATTCATGATACT
5281   ------------+---------+---------+---------+---------+---------+  5340
       CAAGGATGGTCAATTCATCAAAAGACTTGCCGGTCTTCTGGTAAGCTTTAAGTACTATGA

ACTATAAGTTGGTAAACAACCATACTTTTATCCTCATTTTTATTCTCACTAAGAAAAAAG
5341   ------------+---------+---------+---------+---------+---------+  5400
       TGATATTCAACCATTTGTTGGTATGAAAATAGGAGTAAAAATAAGAGTGATTCTTTTTTC
```

Fig. 6H

```
      TCAACTCCCCTCCCCTTGCCCAAGTATGAAATATAGGGACAGTATGTATGGTGTGGTCTC
5401  ------------+---------+---------+---------+---------+---------+  5460
      AGTTGAGGGGAGGGGAACGGGTTCATACTTTATATCCCTGTCATACATACCACACCAGAG

ATTTGTTTAGAAAACCACTTATGACTGGGTGCGGTGGCTCACACCTGTAATCCCAGCACT
5461  ------------+---------+---------+---------+---------+---------+  5520
      TAAACAAATCTTTTGGTGAATACTGACCCACGCCACCGAGTGTGGACATTAGGGTCGTGA

TTGGGAGGCTGAGGCGGGCGAATCATTTGAGGTGAGGAATTCGAGACCAGCCTGGCCAGC
5521  ------------+---------+---------+---------+---------+---------+  5580
      AACCCTCCGACTCCGCCCGCTTAGTAAACTCCACTCCTTAAGCTCTGGTCGGACCGGTCG

ATGGTGAAACCCCATCTCTACTAAAAATACAAAAATTAGCCAGGTGTGGTGGCACATGCC
5581  ------------+---------+---------+---------+---------+---------+  5640
      TACCACTTTGGGGTAGAGATGATTTTTATGTTTTTAATCGGTCCACACCACCGTGTACGG

TGTAGTCCCAGCCACTAGGGCGGCTGAGACGCAAGACTTGCTTGAACCCGGGAGGCAGAG
5641  ------------+---------+---------+---------+---------+---------+  5700
      ACATCAGGGTCGGTGATCCCGCCGACTCTGCGTTCTGAACGAACTTGGGCCCTCCGTCTC

GTTGCAGTGAGCCAAGATGGCGCCACTGCATTCCAGCCTGGGCAACAGAGCAAGACCCTG
5701  ------------+---------+---------+---------+---------+---------+  5760
      CAACGTCACTCGGTTCTACCGCGGTGACGTAAGGTCGGACCCGTTGTCTCGTTCTGGGAC

TCTGTCTCAAAACAAAAAACAAAACCACTTATATTGCTAGCTACATTAAGAATTTCTGAA
5761  ------------+---------+---------+---------+---------+---------+  5820
      AGACAGAGTTTTGTTTTTTGTTTTGGTGAATATAACGATCGATGTAATTCTTAAAGACTT

TATGTTACTGAGCTTGCTTGTGGTAACCATTTATAATATCAGAAAGTATATGTACACCAA
5821  ------------+---------+---------+---------+---------+---------+  5880
      ATACAATGACTCGAACGAACACCATTGGTAAATATTATAGTCTTTCATATACATGTGGTT

AACATGTTGAACATCCATGTTGTACAACTGAAATATAAATAATTTTGTCAATTATACCTA
5881  ------------+---------+---------+---------+---------+---------+  5940
      TTGTACAACTTGTAGGTACAACATGTTGACTTTATATTTATTAAAACAGTTAATATGGAT

AATAAAACTGGAAAAAAATTTCTGGAAGTTTATATCTAAAAATGTTAATAGTGCGTACCT
5941  ------------+---------+---------+---------+---------+---------+  6000
      TTATTTTGACCTTTTTTTAAAGACCTTCAAATATAGATTTTTACAATTATCACGCATGGA

CTAGGAAGTGGGCCTGGAAGCCATTCTTACTTTTCAGTCTCTCCCATTCTGTACTGTTTT
6001  ------------+---------+---------+---------+---------+---------+  6060
      GATCCTTCACCCGGACCTTCGGTAAGAATGAAAAGTCAGAGAGGGTAAGACATGACAAAA

TTGTTTTACTTTCGTGCCTGCATTATTTTTCTATTTAAAACAAAAATAAATCTAGTTTAG
6061  ------------+---------+---------+---------+---------+---------+  6120
      AACAAAATGAAAGCACGGACGTAATAAAAAGATAAATTTTGTTTTTATTTAGATCAAATC

CACT
6121  ----  6124
      GTGA
```

Fig. 6I

```
      TTCCGGCTGGACGTTGCCCTGTGTACCTCTTCGACTGCCTGTTCATCTACGACGAACCCC
1     ------------+---------+---------+---------+---------+---------+ 60
      AAGGCCGACCTGCAACGGGACACATGGAGAAGCTGACGGACAAGTAGATGCTGCTTGGGG c
                                                    1  2
      GGGTATTGACCCCAGACAACAATGCCACTTCATATTGCATGAAGACAAAAGGTCCTGTGC
61    ------------+---------+---------+---------+--+------+---------+ 120
      CCCATAACTGGGGTCTGTTGTTACGGTGAAGTATAACGTACTTCTGTTTTCCAGGACACG c
                                     ↓              ↓           2  3
      TCACCTGGGACCCTTCTGGACGTTGCCCTGTGTACCTCTTCGACTGCCTGTTCATCTACG
121   ------------+---------+---------+---------+---------+------+ 180
      AGTGGACCCTGGAAGACCTGCAACGGGACACATGGAGAAGCTGACGGACAAGTAGATGC c
      ACGAACCCCGGGTATTGACCCCAGACAACAATGCCACTTCATATTGGGGACTTCGTCTGG
181   ------------+---------+---------+---------+---------+---------+ 240
      TGCTTGGGGCCCATAACTGGGGTCTGTTGTTACGGTGAAGTATAACCCCTGAAGCAGACC c
                          3  4
      GATTCCAAGGTGCATTCATTGCAAAGTTCCTTAAATATTTTCTCACTGCTTCCTACTAAA
241   ------------+---------+--+------+---------+---------+---------+ 300
      CTAAGGTTCCACGTAAGTAACGTTTCAAGGAATTTATAAAAGAGTGACGAAGGATGATTT c
      GGACGGACAGAGCATTTGTTCTTCAGCCACATACTTTCCTTCCACTGGCCAGCATTCTCC
301   ------------+---------+---------+---------+---------+---------+ 360
      CCTGCCTGTCTCGTAAACAAGAAGTCGGTGTATGAAAGGAAGGTGACCGGTCGTAAGAGG c
                                      4  5
      TCTATTAGACTAGAACTGTGGATAAACCTCAGAAAATGGCCACCCAGCAGAAAGCCTCTG
361   ------------+---------+---------+--+------+---------+---------+ 420
      AGATAATCTGATCTTGACACCTATTTGGAGTCTTTTACCGGTGGGTCGTCTTTCGGAGAC
                                        M  A  T  Q  Q  K  A  S  D - c
      ACGAGAGGATCTCCCAGTTTGATCACAATTTGCTGCCAGAGCTGTCTGCTCTTCTGGGCC
421   ------------+---------+---------+---------+---------+---------+ 480
      TGCTCTCCTAGAGGGTCAAACTAGTGTTAAACGACGGTCTCGACAGACGAGAAGACCCGG
       E  R  I  S  Q  F  D  H  N  L  L  P  E  L  S  A  L  L  G  L - c
      TAGATGCAGTTCAGTTGGCAAAGGAACTAGAAGAAGAGGAGCAGAAGGAGCGAGCAAAAA
481   ------------+---------+---------+---------+---------+---------+ 540
      ATCTACGTCAAGTCAACCGTTTCCTTGATCTTCTTCTCCTCGTCTTCCTCGCTCGTTTTT c      D  A  V  Q  L  A  K  E  L  E  E  E  E  Q  K  E  R  A  K  M -
```

Fig. 7A

```
                TGCAGAAAGGCTACAACTCTCAAATGCGCAGTGAAGCAAAAAGGTTAAAGACTTTTGTGA
      541       ------------+----------+----------+----------+----------+----------+  600
                ACGTCTTTCCGATGTTGAGAGTTTACGCGTCACTTCGTTTTTCCAATTTCTGAAAACACT c             Q  K  G  Y  N  S  Q  M  R  S  E  A  K  R  L  K  T  F  V  T -
                                                      NOT I
                CTTATGAGCCGTACAGCTCATGGATACCACAGGAGATG[GCGGCCGC]TGGGTTTTACTTCA
      601       ------------+----------+----------+----------+----------+----------+  660
                GAATACTCGGCATGTCGAGTACCTATGGTGTCCTCTAC[CGCCGGCG]ACCCAAAATGAAGT c             Y  E  P  Y  S  S  W  I  P  Q  E  M  A  A  A  G  F  Y  F  T -
                CTGGGGTAAAATCTGGGATTCAGTGCTTCTGCTGTAGCCTAATCCTCTTTGGTGCCGGCC
      661       ------------+----------+----------+----------+----------+----------+  720
                GACCCCATTTTAGACCCTAAGTCACGAAGACGACATCGGATTAGGAGAAACCACGGCCGG c             G  V  K  S  G  I  Q  C  F  C  C  S  L  I  L  F  G  A  G  L -
                TCACGAGACTCCCCATAGAAGACCACAAGAGGTTTCATCCAGATTGTGGGTTCCTTTTGA
      721       ------------+----------+----------+----------+----------+----------+  780
                AGTGCTCTGAGGGGTATCTTCTGGTGTTCTCCAAAGTAGGTCTAACACCCAAGGAAAACT c             T  R  L  P  I  E  D  H  K  R  F  H  P  D  C  G  F  L  L  N -
                ACAAGGATGTTGGTAACATTGCCAAGTACGACATAAGGGTGAAGAATCTGAAGAGCAGGC
      781       ------------+----------+----------+----------+----------+----------+  840
                TGTTCCTACAACCATTGTAACGGTTCATGCTGTATTCCCACTTCTTAGACTTCTCGTCCG c             K  D  V  G  N  I  A  K  Y  D  I  R  V  K  N  L  K  S  R  L -
                TGAGAGGAGGTAAAATGAGGTACCAAGAAGAGGAGGCTAGACTTGC[G]TCCTTCAGGAACT
      841       ------------+----------+----------+----------+----------+----------+  900
                ACTCTCCTCCATTTTACTCCATGGTTCTTCTCCTCCGATCTGAACG[C]AGGAAGTCCTTGA c             R  G  G  K  M  R  Y  Q  E  E  E  A  R  L  A  S  F  R  N  W -
                                          EcoRI
                GGCCATTTTATGTCCAAGG[GATATC]CCCTTGTGTGCTCTCAGAGGCTGGCTTTGTCTTTA
      901       ------------+----------+----------+----------+----------+----------+  960
                CCGGTAAAATACAGGTTCC[CTATAG]GGGAACACACGAGAGTCTCCGACCGAAACAGAAAT c             P  F  Y  V  Q  G  I  S  P  C  V  L  S  E  A  G  F  V  F  T -
                   5 6
                CA[G]GTAAACAGGACACGGTACAGTGTTTTTCCTGTGGTGGATGTTTAGGAAATTGGGAAG
      961       ---+-------+----------+----------+----------+----------+----------+  1020
                GT[C]CATTTGTCCTGTGCCATGTCACAAAAGGACACCACCTACAAATCCTTTAACCCTTC c             G  K  Q  D  T  V  Q  C  F  S  C  G  G  C  L  G  N  W  E  E -
                                                         6 7
                AAGGAGATGATCCTTGGAAGGAACATGCCAAATGGTTCCCCA[A]ATGTGAATTTCTTCGGA
     1021       ------------+----------+----------+-------+--+----------+--------+  1080
                TTCCTCTACTAGGAACCTTCCTTGTACGGTTTACCAAGGGGT[T]TACACTTAAAGAAGCCT c             G  D  D  P  W  K  E  H  K  W  F  P  K  C  E  F  L  R  S -
                GTAAGAAATCCTCAGAGGAAATTACCCAGTATATTCAAAGCTACAAGGGATTTGTTGACA
     1081       ------------+----------+----------+----------+----------+----------+  1140
                CATTCTTTAGGAGTCTCCTTTAATGGGTCATATAAGTTTCGATGTTCCCTAAACAACTGT
```

```
                CCACGGACCACTTGCTGGGCTGTGATCTGTCTATTGCTTCAAAACACATCAGCAAACCTG
        1681    ------------+---------+---------+---------+---------+---------+    1740
                GGTGCCTGGTGAACGACCCGACACTAGACAGATAACGAAGTTTTGTGTAGTCGTTTGGAC c            T  D  H  L  L  G  C  D  L  S  I  A  S  K  H  I  S  K  P  V -
                                        BSu36I
                TGCAAGAACCTCTGGTGCTG|CCTGAGG|TCTTTGGCAACTTGAACTCTGTCATGTGTGTGG
        1741    ------------+---------+---------+---------+---------+---------+    1800
                ACGTTCTTGGAGACCACGAC|GGACTCC|AGAAACCGTTGAACTTGAGACAGTACACACACC c            Q  E  P  L  V  L  P  E  V  F  G  N  L  N  S  V  M  C  V  E -

AGGGTGAAGCTGGAAGTGGAAAGACGGTCCTCCTGAAGAAAATAGCTTTTCTGTGGGCAT
        1801    ------------+---------+---------+---------+---------+---------+    1860
                TCCCACTTCGACCTTCACCTTTCTGCCAGGAGGACTTCTTTTATCGAAAAGACACCCGTA c             G  E  A  G  S  G  K  T  V  L  L  K  K  I  A  F  L  W  A  S -

CTGGATGCTGTCCCCTGTTAAACAGGTTCCAGCTGGTTTTCTACCTCTCCCTTAGTTCCA
        1861    ------------+---------+---------+---------+---------+---------+    1920
                GACCTACGACAGGGGACAATTTGTCCAAGGTCGACCAAAAGATGGAGAGGGAATCAAGGT c             G  C  C  P  L  L  N  R  F  Q  L  V  F  Y  L  S  L  S  S  T -

CCAGACCAGACGAGGGGCTGGCCAGTATCATCTGTGACCAGCTCCTAGAGAAAGAAGGAT
        1921    ------------+---------+---------+---------+---------+---------+    1980
                GGTCTGGTCTGCTCCCCGACCGGTCATAGTAGACACTGGTCGAGGATCTCTTTCTTCCTA c             R  P  D  E  G  L  A  S  I  I  C  D  Q  L  L  E  K  E  G  S -

CTGTTACTGAAATGTGCATGAGGAACATTATCCAGCAGTTAAAGAATCAGGTCTTATTCC
        1981    ------------+---------+---------+---------+---------+---------+    2040
                GACAATGACTTTACACGTACTCCTTGTAATAGGTCGTCAATTTCTTAGTCCAGAATAAGG c             V  T  E  M  C  M  R  N  I  I  Q  Q  L  K  N  Q  V  L  F  L -

TTTTAGATGACTACAAAGAAATATGTTCAATCCCTCAAGTCATAGGAAAACTGATTCAAA
        2041    ------------+---------+---------+---------+---------+---------+    2100
                AAAATCTACTGATGTTTCTTTATACAAGTTAGGGAGTTCAGTATCCTTTTGACTAAGTTT c             L  D  D  Y  K  E  I  C  S  I  P  Q  V  I  G  K  L  I  Q  K -

AAAACCACTTATCCCGGACCTGCCTATTGATTGCTGTCCGTACAAACAGGGCCAGGGACA
        2101    ------------+---------+---------+---------+---------+---------+    2160
                TTTTGGTGAATAGGGCCTGGACGGATAACTAACGACAGGCATGTTTGTCCCGGTCCCTGT c             N  H  L  S  R  T  C  L  L  I  A  V  R  T  N  R  A  R  D  I -
                                                         ↓
                TCCGCCGATACCTAGAGACCATTCTAGAGATC|A|AGCATTTCCCTTTTATAATACTGTCT
        2161    ------------+---------+---------+---------+---------+---------+    2220
                AGGCGGCTATGGATCTCTGGTAAGATCTCTAG|T|TCGTAAAGGGAAAATATTATGACAGA c             R  R  Y  L  E  T  I  L  E  I  Q  A  F  P  F  Y  N  T  V  C -

GTATATTACGGAAGCTCTTTTCACATAATATGACTCGTCTGCGAAAGTTTATGGTTTACT
```

Fig. 7D

```
2221 ----------+----------+----------+----------+----------+---------+ 2280
     CATATAATGCCTTCGAGAAAAGTGTATTATACTGAGCAGACGCTTTCAAATACCAAATGA c       I  L  R  K  L  F  S  H  N  M  T  R  L  R  K  F  M  V  Y  F -

TTGGAAAGAACCAAAGTTTGCAGAAGATACAGAAAACTCCTCTCTTTGTGGCGGCGATCT
2281 ----------+----------+----------+----------+----------+---------+ 2340
     AACCTTTCTTGGTTTCAAACGTCTTCTATGTCTTTTGAGGAGAGAAACACCGCCGCTAGA c       G  K  N  Q  S  L  Q  K  I  Q  K  T  P  L  F  V  A  A  I  C -

GTGCTCATTGGTTTCAGTATCCTTTTGACCCATCCTTTGATGATGTGGCTGTTTTCAAGT
2341 ----------+----------+----------+----------+----------+---------+ 2400
     CACGAGTAACCAAAGTCATAGGAAAACTGGGTAGGAAACTACTACACCGACAAAAGTTCA c       A  H  W  F  Q  Y  P  F  D  P  S  F  D  D  V  A  V  F  K  S -

CCTATATGGAACGCCTTTCCTTAAGGAACAAAGCGACAGCTGAAATTCTCAAAGCAACTG
2401 ----------+----------+----------+----------+----------+---------+ 2460
     GGATATACCTTGCGGAAAGGAATTCCTTGTTTCGCTGTCGACTTTAAGAGTTTCGTTGAC c       Y  M  E  R  L  S  L  R  N  K  A  T  A  E  I  L  K  A  T  V -

TGTCCTCCTGTGGTGAGCTGGCCTTGAAAGGGTTTTTTTTCATGTTGCTTTGAGTTTAATG
2461 ----------+----------+----------+----------+----------+---------+ 2520
     ACAGGAGGACACCACTCGACCGGAACTTTCCCAAAAAAAGTACAACGAAACTCAAATTAC c       S  S  C  G  E  L  A  L  K  G  F  F  S  C  C  F  E  F  N  D -

ATGATGATCTCGCAGAAGCAGGGGTTGATGAAGATGAAGATCTAACCATGTGCTTGATGA
2521 ----------+----------+----------+----------+----------+---------+ 2580
     TACTACTAGAGCGTCTTCGTCCCCAACTACTTCTACTTCTAGATTGGTACACGAACTACT c       D  D  L  A  E  A  G  V  D  E  D  E  D  L  T  M  C  L  M  S -

GCAAATTTACAGCCCAGAGACTAAGACCATTCTACCGGTTTTTAAGTCCTGCCTTCCAAG
2581 ----------+----------+----------+----------+----------+---------+ 2640
     CGTTTAAATGTCGGGTCTCTGATTCTGGTAAGATGGCCAAAAATTCAGGACGGAAGGTTC c       K  F  T  A  Q  R  L  R  P  F  Y  R  F  L  S  P  A  F  Q  E

AATTTCTTGCGGGGATGAGGCTGATTGAACTCCTGGATTCAGATAGGCAGGAACATCAAG
2641 ----------+----------+----------+----------+----------+---------+ 2700
     TTAAAGAACGCCCCTACTCCGACTAACTTGAGGACCTAAGTCTATCCGTCCTTGTAGTTC c       F  L  A  G  M  R  L  I  E  L  L  D  S  D  R  Q  E  H  Q  D -

ATTTGGGACTGTATCATTTGAAACAAATCAACTCACCCATGATGACTGTAAGCGCCTACA
2701 ----------+----------+----------+----------+----------+---------+ 2760
     TAAACCCTGACATAGTAAACTTTGTTTAGTTGAGTGGGTACTACTGACATTCGCGGATGT c       L  G  L  Y  H  L  K  Q  I  N  S  P  M  M  T  V  S  A  Y  N -

ACAATTTTTTGAACTATGTCTCCAGCCTCCCTTCAACAAAAGCAGGGCCCAAAATTGTGT
2761 ----------+----------+----------+----------+----------+---------+ 2820
```

Fig. 7E

```
                TGTTAAAAAACTTGATACAGAGGTCGGAGGGAAGTTGTTTTCGTCCCGGGTTTTAACACA c          N  F  L  N  Y  V  S  S  L  P  S  T  K  A  G  P  K  I  V  S -
                CTCATTTGCTCCATTTAGTGGATAACAAAGAGTCATTGGAGAATATATCTGAAAATGATG
      2821    ----------+----------+----------+----------+----------+----------+   2880
                GAGTAAACGAGGTAAATCACCTATTGTTTCTCAGTAACCTCTTATATAGACTTTTACTAC c          H  L  L  H  L  V  D  N  K  S  S  L  E  N  I  S  E  N  D  D -
                                                PstI
                ACTACTTAAAGCACCAGCCAGAAATTTCACTGCAGATGCAGTTACTTAGGGGATTGTGGC
      2881    ----------+----------+----------+----------+----------+----------+   2940
                TGATGAATTTCGTGGTCGGTCTTTAAAGTGACGTCTACGTCAATGAATCCCCTAACACCG c          Y  L  K  H  Q  P  E  I  S  L  Q  M  Q  L  L  R  G  L  W  Q -
                              HindIII
                AAATTTGTCCACAAGCTTACTTTTCAATGGTTTCAGAACATTTACTGGTTCTTGCCCTGA
      2941    ----------+----------+----------+----------+----------+----------+   3000
                TTTAAACAGGTGTTCGAATGAAAAGTTACCAAAGTCTTGTAAATGACCAAGAACGGGACT c          I  C  P  Q  A  Y  F  S  M  V  S  E  H  L  L  V  L  A  L  K -
                AAACTGCTTATCAAAGCAACACTGTTGCTGCGTGTTCTCCATTTGTTTTGCAATTCCTTC
      3001    ----------+----------+----------+----------+----------+----------+   3060
                TTTGACGAATAGTTTCGTTGTGACAACGACGCACAAGAGGTAAACAAAACGTTAAGGAAG c          T  A  Y  Q  S  N  T  V  A  A  C  S  P  F  V  L  Q  F  L  Q -
                AAGGGAGAACACTGACTTTGGGTGCGCTTAACTTACAGTACTTTTTCGACCACCCAGAAA
      3061    ----------+----------+----------+----------+----------+----------+   3120
                TTCCCTCTTGTGACTGAAACCCACGCGAATTGAATGTCATGAAAAAGCTGGTGGGTCTTT c          G  R  T  L  T  L  G  A  L  N  L  Q  Y  F  F  D  H  P  E  S -
                HindIII                          ↓
                GCTTGTCATTGTTGAGGAGCATCCACTTCCAATACGAGGAAATAAGACATCACCCAGAG
      3121    ----------+----------+----------+----------+----------+----------+   3180
                CGAACAGTAACAACTCCTCGTAGGTGAAGGTTATGCTCCTTTATTCTGTAGTGGGTCTC c          L  S  L  L  R  S  I  H  F  S  I  R  G  N  K  T  S  P  R  A -
                CACATTTTTCAGTTCTGGAAACATGTTTTGACAAATCACAGGTGCCAACTATAGATCAGG
      3181    ----------+----------+----------+----------+----------+----------+   3240
                GTGTAAAAAGTCAAGACCTTTGTACAAAACTGTTTAGTGTCCACGGTTGATATCTAGTCC c          H  F  S  V  L  E  T  C  F  D  K  S  Q  V  P  T  I  D  Q  D -
                ACTATGCTTCTGCCTTTGAACCTATGAATGAATGGGAGCGAAATTTAGCTGAAAAAGAGG
      3241    ----------+----------+----------+----------+----------+----------+   3300
                TGATACGAAGACGGAAACTTGGATACTTACTTACCCTCGCTTTAAATCGACTTTTTCTCC c          Y  A  S  A  F  E  P  M  N  E  W  E  R  N  L  A  E  K  E  D -
                ATAATGTAAAGAGCTATATGGATATGCAGCGCAGGGCATCACCAGACCTTAGTACTGGCT
      3301    ----------+----------+----------+----------+----------+----------+   3360
                TATTACATTTCTCGATATACCTATACGTCGCGTCCCGTAGTGGTCTGGAATCATGACCGA
```

Fig. 7F

```
c        N  V  K  S  Y  M  D  M  Q  R  R  A  S  P  D  L  S  T  G  Y -
                                                 XGaI
         ATTGGAAACTTTCTCCAAAGCAGTACAAGATTCCCTGTCTAGAAGTCGATGTGAATGATA
    3361 ---------+---------+---------+---------+---------+---------+ 3420
         TAACCTTTGAAAGAGGTTTCGTCATGTTCTAAGGGACAGATCTTCAGCTACACTTACTAT c        W  K  L  S  P  K  Q  Y  K  I  P  C  L  E  V  D  V  N  D  I -

TTGATGTTGTAGGCCAGGATATGCTTGAGATTCTAATGACAGTTTTCTCAGCTTCACAGC
    3421 ---------+---------+---------+---------+---------+---------+ 3480
         AACTACAACATCCGGTCCTATACGAACTCTAAGATTACTGTCAAAAGAGTCGAAGTGTCG c        D  V  V  G  Q  D  M  L  E  I  L  M  T  V  F  S  A  S  Q  R -

GCATCGAACTCCATTTAAACCACAGCAGAGGCTTTATAGAAAGCATCCGCC CAGCTCTTG
    3481 ---------+---------+---------+---------+---------+---------+ 3540
         CGTAGCTTGAGGTAAATTTGGTGTCGTCTCCGAAATATCTTTCGTAGGCGGGTCGAGAAC c        I  E  L  H  L  N  H  S  R  G  F  I  E  S  I  R  P  A  L  E -

AGCTGTCTAAGGCCTCTGTCACCAAGTGCTCCATAAGCAAGTTGGAACTCAGCGCAGCCG
    3541 ---------+---------+---------+---------+---------+---------+ 3600
         TCGACAGATTCCGGAGACAGTGGTTCACGAGGTATTCGTTCAACCTTGAGTCGCGTCGGC c        L  S  K  A  S  V  T  K  C  S  I  S  K  L  E  L  S  A  A  E -

AACAGGAACTGCTTCTCACCCTGCCTTCCCTGGAATCTCTTGAAGTCTCAGGGACAATCC
    3601 ---------+---------+---------+---------+---------+---------+ 3660
         TTGTCCTTGACGAAGAGTGGGACGGAAGGGACCTTAGAGAACTTCAGAGTCCCTGTTAGG c        Q  E  L  L  L  T  L  P  S  L  E  S  L  E  V  S  G  T  I  Q -
               13 14
         AGTCACAAGACCAAATCTTTCCTAATCTGGATAAGTTCCTGTGCCTGAAAGAACTGTCTG
    3661 ---------+---------+---------+---------+---------+---------+ 3720
         TCAGTGTTCTGGTTTAGAAAGGATTAGACCTATTCAAGGACACGGACTTTCTTGACAGAC c        S  Q  D  Q  I  F  P  N  L  D  K  F  L  C  L  K  E  L  S  V -
         BstYI
         TGGATCTGGAGGGCAATATAAATGTTTTTTCAGTCATTCCTGAAGAATTTCCAAACTTCC
    3721 ---------+---------+---------+---------+---------+---------+ 3780
         ACCTAGACCTCCCGTTATATTTACAAAAAAGTCAGTAAGGACTTCTTAAAGGTTTGAAGG c        D  L  E  G  N  I  N  V  F  S  V  I  P  E  E  F  P  N  F  H -
                                                              14  14A
         ACCATATGGAGAAATTATTGATCCAAATTTCAGCTGAGTATGATCCTTCCAAACTAGTAA
    3781 ---------+---------+---------+---------+---------+---------+ 3840
         TGGTATACCTCTTTAATAACTAGGTTTAAAGTCGACTCATACTAGGAAGGTTTGATCATT c        H  M  E  K  L  L  I  Q  I  S  A  E  Y  D  P  S  K  L  V  K -

AATTAATTCAAAATTCTCCAAACCTTCATGTTTTCCATCTGAAGTGTAACTTCTTTTCGG
    3841 ---------+---------+---------+---------+---------+---------+ 3900
         TTAATTAAGTTTTAAGAGGTTTGGAAGTACAAAAGGTAGACTTCACATTGAAGAAAAGCC c        L  I  Q  N  S  P  N  L  H  V  F  H  L  K  C  N  F  F  S  D -
```

Fig. 7G

```
                ATTTTGGGTCTCTCATGACTATGCTTGTTTCCTGTAAGAAACTCACAGAAATTAAGTTTT
         3901   ---------+---------+---------+---------+---------+---------+   3960
                TAAAACCCAGAGAGTACTGATACGAACAAAGGACATTCTTTGAGTGTCTTTAATTCAAAA c          L  G  S  L  M  T  H  L  V  S  C  K  K  L  T  E  I  K  F  S -
                                            14A 15
                CGGATTCATTTTTTCAAGCCGTCCCATTTGTTGCCAGTTTGCCAAATTTTATTTCTCTGA
         3961   ---------+---------+---------+---------+---------+---------+   4020
                GCCTAAGTAAAAAAGTTCGGCAGGGTAAACAACGGTCAAACGGTTTAAAATAAAGAGACT c          D  S  F  F  Q  A  V  P  F  V  A  S  L  P  N  F  I  S  L  K -
                                                                    15 16
                AGATATTAAATCTTGAAGGCCAGCAATTTCCTGATGAGGAAACATCAGAAAAATTTGCCT
         4021   ---------+---------+---------+---------+---------+---------+   4080
                TCTATAATTTAGAACTTCCGGTCGTTAAAGGACTACTCCTTTGTAGTCTTTTTAAACGGA c          I  L  N  L  E  G  Q  Q  F  P  D  E  E  T  S  E  K  F  A  Y -
                ACATTTTAGGTTCTCTTAGTAACCTGGAAGAATTGATCCTTCCTACTGGGGATGGAATTT
         4081   ---------+---------+---------+---------+---------+---------+   4140
                TGTAAAATCCAAGAGAATCATTGGACCTTCTTAACTAGGAAGGATGACCCCTACCTTAAA c          I  L  G  S  L  S  N  L  E  E  L  I  L  P  T  G  D  G  I  Y -
                ATCGAGTGGCCAAACTGATCATCCAGCAGTGTCAGCAGCTTCATTGTCTCCGAGTCCTCT
         4141   ---------+---------+---------+---------+---------+---------+   4200
                TAGCTCACCGGTTTGACTAGTAGGTCGTCACAGTCGTCGAAGTAACAGAGGCTCAGGAGA c          R  V  A  K  L  I  I  Q  Q  C  Q  Q  L  H  C  L  R  V  L  S -
                                                    16 17
                CATTTTTCAAGACTTTGAATGATGACAGCGTGGTGGAAATTGCCAAAGTAGCAATCAGTG
         4201   ---------+---------+---------+---------+---------+---------+   4260
                GTAAAAAGTTCTGAAACTTACTACTGTCGCACCACCTTTAACGGTTTCATCGTTAGTCAC c          F  F  K  T  L  N  D  D  S  V  V  E  I  A  K  V  A  I  S  G -
                GAGGTTTCCAGAAACTTGAGAACCTAAAGCTTTCAATCAATCACAAGATTACAGAGGAAG
         4261   ---------+---------+---------+---------+---------+---------+   4320
                CTCCAAAGGTCTTTGAACTCTTGGATTTCGAAAGTTAGTTAGTGTTCTAATGTCTCCTTC c          G  F  Q  K  L  E  N  L  K  L  S  I  N  H  K  I  T  E  E  G -
                GATACAGAAATTTCTTTCAAGCACTGGACAACATGCCAAACTTGCAGGAGTTGGACATCT
         4321   ---------+---------+---------+---------+---------+---------+   4380
                CTATGTCTTTAAAGAAAGTTCGTGACCTGTTGTACGGTTTGAACGTCCTCAACCTGTAGA c          Y  R  N  F  F  Q  A  L  D  N  M  P  N  L  Q  E  L  D  I  S -
                CCAGGCATTTCACAGAGTGTATCAAAGCTCAGGCCACAACAGTCAAGTCTTTGAGTCAAT
         4381   ---------+---------+---------+---------+---------+---------+   4440
                GGTCCGTAAAGTGTCTCACATAGTTTCGAGTCCGGTGTTGTCAGTTCAGAAACTCAGTTA c          R  H  F  T  E  C  I  K  A  Q  A  T  T  V  K  S  L  S  Q  C -
                GTGTGTTACGACTACCAAGGCTCATTAGACTGAACATGTTAAGTTGGCTCTTGGATGCAG
```

Fig. 7H

```
                  CACACAATGCTGATGGTTCCGAGTAATCTGACTTGTACAATTCAACCGAGAACCTACGTC
4441 ---------+---------+---------+---------+---------+---------+ 4500 c       V  L  R  L  P  R  L  I  R  L  N  M  L  S  W  L  L  D  A  D -

ATGATATTGCATTGCTTAATGTCATGAAAGAAAGACATCCTCAATCTAAGTACTTAACTA
4501 ---------+---------+---------+---------+---------+---------+ 4560
     TACTATAACGTAACGAATTACAGTACTTTCTTTCTGTAGGAGTTAGATTCATGAATTGAT c       D  I  A  L  L  N  V  M  K  E  R  H  P  Q  S  K  Y  L  T  I -

TTCTCCAGAAATGGATACTGCCGTTCTCTCCAATCATTCAGAAATAAAAGATTCAGCTAA
4561 ---------+---------+---------+---------+---------+---------+ 4620
     AAGAGGTCTTTACCTATGACGGCAAGAGAGGTTAGTAAGTCTTTATTTTCTAAGTCGATT c       L  Q  K  W  I  L  P  P  S  P  I  I  Q  K  *               -

AAACTGCTGAATCAATAATTTGTCTTGGGGCATATTGAGGATGTAAAAAAAGTTGTTGAT
4621 ---------+---------+---------+---------+---------+---------+ 4680
     TTTGACGACTTAGTTATTAAACAGAACCCCGTATAACTCCTACATTTTTTTCAACAACTA c                                                                 -

TAATGCTAAAAACAAATTATCCAAAATTATTTTATTAAATATTGCATACAAAAGAAAATG
4681 ---------+---------+---------+---------+---------+---------+ 4740
     ATTACGATTTTTGTTTAATAGGTTTTAATAAAATAATTTATAACGTATGTTTTCTTTTAC c                                                                 -

TGTAAGGCTTGCTAAAAAACAAAACAAAACAAAACACAGTCCTGCATACTCACCACCAAG
4741 ---------+---------+---------+---------+---------+---------+ 4800
     ACATTCCGAACGATTTTTTGTTTTGTTTTGTTTTGTGTCAGGACGTATGAGTGGTGGTTC c                                                                 -

GCTCAAGAAATAAATCATCACCAATACCTTTGAGGTCCCTGAGTAATCCACCCCAGCTAA
4801 ---------+---------+---------+---------+---------+---------+ 4860
     CGAGTTCTTTATTTAGTAGTGGTTATGGAAACTCCAGGGACTCATTAGGTGGGGTCGATT c                                                                 -

GGCAAACCCTTCAATCAAGTTTATACAGCAAACCCTCCATTGTCCATGGTCAACAGGGAA
4861 ---------+---------+---------+---------+---------+---------+ 4920
     CCGTTTGGGAAGTTAGTTCAAATATGTCGTTTGGGAGGTAACAGGTACCAGTTGTCCCTT c                                                                 -

GGGGTTGGGGACAGGTCTGCCAATCTATCTAAAAGCCACAATATGGAAGAATATTCAATT
4921 ---------+---------+---------+---------+---------+---------+ 4980
     CCCCAACCCCTGTCCAGACGGTTAGATAGATTTTCGGTGTTATACCTTCTTATAAGTTAA c                                                                 -

TATATAATAAATGGCTAACTTAACGGTTGAATCACTTTCATACATGGATGAAACGGGTTT
4981 ---------+---------+---------+---------+---------+---------+ 5040
     ATATATTATTTACCGATTGAATTGCCAACTTAGTGAAAGTATGTACCTACTTTGCCCAAA
```

Fig. 7I

```
                    BamHI
         AACACAGGATCCACATGAATCTTCTGTGGGCCAAGAGATGTTCCTTAATCCTTGTAGAAC
    5041 ---------+---------+---------+---------+---------+---------+ 5100
         TTGTGTCCTAGGTGTACTTAGAAGACACCCGGTTCTCTACAAGGAATTAGGAACATCTTG

CTGTTTTCTATATTGAACTAGCTTTGGTACAGTAGAGTTAACTTACTTTCCATTTATCCA
    5101 ---------+---------+---------+---------+---------+---------+ 5160
         GACAAAAGATATAACTTGATCGAAACCATGTCATCTCAATTGAATGAAAGGTAAATAGGT

CTGCCAATATAAAGAGGAAACAGGGGTTAGGGAAAAATGACTTCATTCCAGAGGCTTCTC
    5161 ---------+---------+---------+---------+---------+---------+ 5220
         GACGGTTATATTTCTCCTTTGTCCCCAATCCCTTTTTACTGAAGTAAGGTCTCCGAAGAG

AGAGTTCAACATATGCTATAATTTAGAATTTTCTTATGAATCCACTCTACTTGGGTAGAA
    5221 ---------+---------+---------+---------+---------+---------+ 5280
         TCTCAAGTTGTATACGATATTAAATCTTAAAAGAATACTTAGGTGAGATGAACCCATCTT

AATATTTTATCTCTAGTGATTGCATATTATTTCCATATCATAGTATTTCATAGTATTATA
    5281 ---------+---------+---------+---------+---------+---------+ 5340
         TTATAAAATAGAGATCACTAACGTATAATAAAGGTATAGTATCATAAAGTATCATAATAT

TTTGATATGAGTGTCTATATCAATGTCAGTGTCCAGAATTTCGTTCCTACCAGTTAAGTA
    5341 ---------+---------+---------+---------+---------+---------+ 5400
         AAACTATACTCACAGATATAGTTACAGTCACAGGTCTTAAAGCAAGGATGGTCAATTCAT

GTTTTCTGAACGGCCAGAAGACCATTCGAAATTCATGATACTACTATAAGTTGGTAAACA
    5401 ---------+---------+---------+---------+---------+---------+ 5460
         CAAAAGACTTGCCGGTCTTCTGGTAAGCTTTAAGTACTATGATGATATTCAACCATTTGT

ACCATACTTTTATCCTCATTTTTATTCTCACTAAGAAAAAAGTCAACTCCCCTCCCCTTG
    5461 ---------+---------+---------+---------+---------+---------+ 5520
         TGGTATGAAAATAGGAGTAAAAATAAGAGTGATTCTTTTTTCAGTTGAGGGGAGGGGAAC

CCCAAGTATGAAATATAGGGACAGTATGTATGGTGTGGTCTCATTTGTTTAAAAAACCAC
    5521 ---------+---------+---------+---------+---------+---------+ 5580
         GGGTTAATACTTTATATCCCTGTCATACATACCACACCAGAGTAAACAAATTTTTTGGTG
```

Fig. 7J

```
                TTATGACTGGGTGCGGTGGCTCACACCTGTAATCCCACCACTTTGGGAGGCTGAGGCGGG
c       5581    ------------+---------+---------+---------+---------+---------+ 5640
                AATACTGACCCACGCCACCGAGTGTGGACATTAGGGTGGTGAAACCCTCCGACTCCGCCC c                               EcoRI
                CGAATCATTTGAGGTGAGGAATTCGAGACCAGCCTGGCCAGCATGGTGAAACCCCATCTC
        5641    ------------+---------+---------+---------+---------+---------+ 5700
                GCTTAGTAAACTCCACTCCTTAAGCTCTGGTCGGACCGGTCGTACCACTTTGGGGTAGAG
c

TACTAAAAATACAAAAATTAGCCAGGTGTGGTGGCACATGCCTGTAAGTCCCAGCCACTA
        5701    ------------+---------+---------+---------+---------+---------+ 5760
                ATGATTTTTATGTTTTTAATCGGTCCACACCACCGTGTACGGACATTCAGGGTCGGTGAT c
                GGGCGGCTGAGACGCAAGACTTGCTTGAACCCGGGAGGCAGAGGTTGCAGTGAGCCAAGA
        5761    ------------+---------+---------+SmaI----+---------+---------+ 5820
                CCCGCCGACTCTGCGTTCTGAACGAACTTGGGCCCTCCGTCTCCAACGTCACTCGGTTCT c
                TGGCGCCACTGCATTCCAGCCTGGGCAACAGAGCAAGACCCTGTCTGTCTCAAAACAAAA
        5821    ------------+---------+---------+---------+---------+---------+ 5880
                ACCGCGGTGACGTAAGGTCGGACCCGTTGTCTCGTTCTGGGACAGACAGAGTTTTGTTTT c
                AACAAAACCACTTATATTGCTAGCTACATTAAGAATTTCTGAATATGTTACTGAGCTTGC
        5881    ------------+---------+---------+---------+---------+---------+ 5940
                TTGTTTTGGTGAATATAACGATCGATGTAATTCTTAAAGACTTATACAATGACTCGAACG c
                TTGTGGTAACCATTTATAATATCAGAAAGTATATGTACACCAAAACATGTTGAACATCCA
        5941    ------------+---------+---------+---------+---------+---------+ 6000
                AACACCATTGGTAAATATTATAGTCTTTCATATACATGTGGTTTTGTACAACTTGTAGGT c
                TGTTGTACAACTTGAAATATAAATAATTTTGTCAATTATACCTAAATAAAACTGGAAAAA
        6001    ------------+---------+---------+---------+---------+---------+ 6060
                ACAACATGTTGAACTTTATATTTATTAAAACAGTTAATATGGATTTATTTTGACCTTTTT c
                AATTTCTGGAAGTTTATATCTAAAAATGTTAATAGTGCGTACCTCTAGGAAGTGGGCCTG
        6061    ------------+---------+---------+---------+---------+---------+ 6120
                TTAAAGACCTTCAAATATAGATTTTTACAATTATCACGCATGGAGATCCTTCACCCGGAC
```

Fig. 7K c

```
       GAAGCCATTCTTACTTTTCAGTCTCTCCCATTCTGTACTGTTTTTTGTTTTACTTTCGTG
6121   ------------+---------+---------+---------+---------+---------+ 6180
       CTTCGGTAAGAATGAAAAGTCAGAGAGGGTAAGACATGACAAAAAACAAAATGAAAGCAC
``` c

```
       CCTGCATTATTTTTCTATTTAAAACAAAAATAAATCTAGTTTAGCACT  poly A tail
6181   ---------+---------+---------+---------+--------  6228
```

Fig. 7L

USE OF NEURONAL APOPTOSIS INHIBITOR PROTEIN (NAIP)

FIELD OF THE INVENTION

This invention relates in general to the function of the NAIP inhibitor protein in apoptosis and more particularly to the use of NAIP antibodies, proteins, and nucleic acids to characterize NAIP, identify compounds which modulate NAIP, and diagnose and treat conditions affected by changes in NAIP levels.

BACKGROUND OF THE INVENTION

Apoptosis is a morphologically distinct form of programmed cell death that is important in the normal development and maintenance of multicellular organisms. Dysregulation of apoptosis can take the form of inappropriate suppression of cell death, as occurs in the development of some cancers, or in a failure to control the extent of cell death, as is believed to occur in acquired immunodeficiency and certain neurodegenerative disorders, such as spinal muscular atrophy (SMA).

Childhood spinal muscular atrophies are neurodegenerative disorders characterized by progressive spinal cord motor neuron depletion and are among the most common autosomal recessive disorders (Dubowitz, V. 1978, Brooke, M. A. 1986). Type I SMA is the most frequent inherited cause of death in infancy. The loss of motor neurons in SMA, has led to suggestions that an inappropriate continuation or reactivation of normally occurring motor neuron apoptosis may underlie the disorder (Sarnat, H. B. 1992). NAIP, a gene associated with SMA, has been mapped to human chromosome 5q13.1

Some baculoviruses encode proteins that are termed inhibitors of apoptosis proteins (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which may be involved in DNA binding, and two N-terminal domains that consist of a 70 amino acid repeat motif termed a BIR domain (Baculovirus IAP Repeat).

SUMMARY OF THE INVENTION

We have discovered uses for NAIP proteins, nucleic acids, and antibodies for the detection and treatment of conditions involving apoptosis. Furthermore, we have discovered a novel NAIP sequence and a NAIP fragment with enhanced anti-apoptotic activities.

In general, the invention features a substantially pure nucleic acid molecule, such as a genomic, cDNA, antisense DNA, RNA, or a synthetic nucleic acid molecule, that encodes or corresponds to a mammalian NAIP polypeptide. This nucleic acid may be incorporated into a vector. Such a vector may be in a cell, such as a mammalian, yeast, nematode, or bacterial cell. The nucleic acid may also be incorporated into a transgenic animal or embryo thereof. In preferred embodiments, the nucleic acid molecule is a human NAIP nucleic acid. In most preferred embodiments the NAIP gene is a human NAIP gene. In other various preferred embodiments, the cell is a transformed cell.

According to one preferred embodiment, the nucleic acid sequence includes the cDNA sequences encoding exons 14a and 17. In a more preferred embodiment the sequence includes exons 1–14, 14a, and 15–17. In the most preferred embodiments the sequence also includes the complete 5' and 3' untranslated regions of the NAIP gene and is represented as Seq. ID No. 2, 21, or 23, most preferably, as in Seq. ID No. 21. In other preferred embodiments, the nucleic acid is a purified nucleotide sequence comprising genomic DNA, cDNA, mRNA, anti-sense DNA or other DNA substantially identical to the cDNA sequences of Seq. ID No. 2, 21, or 23 corresponding to the cDNA sequences of the invention. Most preferably exons 1 to 14 and 14a to 17 are as described in Seq. ID No. 21.

In one preferred embodiment, the nucleic acid sequence includes the cDNA sequences (shown in FIG. 6) of SEQ ID NO:21, encoding exon 14a, which corresponds to nucleic acids 3734–3886, and exon 17, which corresponds to nucleic acids 4139–4503. In another preferred embodiment, the nucleic acid sequence includes the sequence of SEQ ID NO:23, encoding exon 14a, which corresponds to nucleic acids 3838–3990, and exon 17, which corresponds to nucleic acids 4243–4605.

In specific embodiments, the invention features nucleic acid sequences substantially identical to the sequences shown in FIG. 2I, or fragments thereof. In another aspect, the invention also features RNA which is encoded by the DNA described herein. Preferably, the RNA is mRNA. In another embodiment the RNA is antisense RNA that is complementing to the coding strand of NAIP.

In a second aspect of the invention, the NAIP encoding nucleic acid comprises at least the 3 BIR domains of a NAIP sequence provided herein (e.g., nucleotides 1–1360 of the NAIP sequence provided in FIG. 6), but lacks at least some of the sequences encoding the carboxy terminus of the NAIP polypeptide. Preferably, at least 30 nucleic acids are deleted from the region of the NAIP gene between nucleic acids 1360 (i.e., the end of the BIR domains) 4607 (i.e., the end of the coding sequence) of the NAIP sequence shown in FIG. 6, Seq. ID No. 21. More preferably, at least 100 nucleotides are deleted, and even more preferably at least 1000 nucleotides are deleted. In the most preferred embodiment, up to 3247 nucleotides are deleted. Preferably, the deletion results in a statistically significant increase in the anti-apoptotic activity of the encoded protein on one of the assays provided herein.

In a third aspect, the invention features a substantially pure DNA which includes a promoter capable of expressing or activating the expression of the NAIP gene or fragments thereof in a cell susceptible to apoptosis. In preferred embodiments of this aspect, the NAIP gene is human NAIP or fragments thereof, as described above. In further preferred embodiments of this aspect of the invention, the promoter is the promoter native to the NAIP gene. Additionally, transcriptional and translational regulatory regions are, preferably, those native to a NAIP gene.

In another aspect, the invention provides transgenic cell lines, including the NAIP nucleic acids of the invention. The transgenic cells of the invention are preferably cells that are altered in their apoptotic response. In preferred embodiments, the transgenic mammalian cell is a fibroblast, neuronal cell, a pulmonary cell, a renal cell, a lymphocyte cell, a glial cell, a myocardial cell, an embryonic stem cell, or an insect cell. Most preferably, the neuron is a motor neuron and the lymphocyte is a $CD4^+$ T cell.

In another related aspect, the invention features a method of altering the level of apoptosis that involves producing a transgenic cell having a transgene encoding a NAIP polypeptide or antisense nucleic acid. The transgene is integrated into the genome of the cell in a way that allows for expression. Furthermore, the level of expression in the cell is sufficient to alter the level of apoptosis. In preferred embodiments the transgene is in a motor neuron or a myocardial cell.

In yet another related aspect, the invention features a transgenic animal, preferably a mammal, more preferably a rodent, and most preferably a mouse, having a NAIP gene as described above inserted into the genome (mutant or wild-type), or a knockout of a NAIP gene in the genome, or both. A transgenic animal expressing NAIP antisense nucleic acid is also included. The transgenic animals may express either an increased or a decreased amount of NAIP polypeptide, depending on the construct used and the nature of the genomic alteration. For example, utilizing a nucleic acid molecule that encodes all or part of a NAIP to engineer a knockout mutation in a NAIP gene would generate an animal with decreased expression of either all or part of the corresponding NAIP polypeptide. In contrast, inserting exogenous copies of all or part of a NAIP gene into the genome, preferably under the control of active regulatory and promoter elements, would lead to increased expression or the corresponding NAIP polypeptide.

In another aspect, the invention features a method of detecting a NAIP gene in a cell by detecting the NAIP gene, or a portion thereof (which is greater than 9 nucleotides, and preferably greater than 18 nucleotides in length), with a preparation of genomic DNA from the cell. The NAIP gene and the genomic DNA are brought into contact under conditions that allow for hybridization (and therefore, detection) of nucleic acid sequences in the cell that are at least 50% identical to the DNA encoding the NAIP polypeptides. Preferably, the nucleic acid used comprised at least a part of exon 14a or exon 17, as provided in FIGS. 6 and 7.

In another aspect, the invention features a method of producing a NAIP polypeptide in vivo or in vitro. In one embodiment, this method involves providing a cell with nucleic acid encoding all or part of a NAIP polypeptide (which is positioned for expression in the cell), culturing the cell under conditions that allow for expression of the nucleic acid, and isolating the NAIP polypeptide. In preferred embodiments, the NAIP polypeptide is expressed by DNA that is under the control of a constitutive or inducible promoter. As described herein, the promoter may be a native or heterologous promotor. In preferred embodiments the nucleic acid comprises exon 14a or exon 17. Most preferably the nucleic acid is the nucleic acid shown in either FIG. 6 or FIG. 7. Most preferably, it is the sequence of FIG. 6.

In another aspect, the invention features substantially pure mammalian NAIP polypeptide. Preferably, the polypeptide includes an amino acid sequence that is substantially identical to one of the amino acid sequences shown in any one of FIG. 6 or 7. Most preferably, the polypeptide is the human NAIP polypeptide of FIG. 6. Fragments including at least two BIR domains, as provided herein, are also a part of the invention. Preferably, the fragment has at least three BIR domains. For example, polypeptides encoded by the nucleic acids described above having deletions between nucleic acids 1360 and the end of the gene are a part of the invention. In one embodiment, the NAIP fragments included those NAIP fragments comprising at least 15 sequential amino acids of Seq. ID No. 22 or 24. Most preferably the fragment includes at least a portion of exon 14a or exon 17.

In another aspect, the invention features a recombinant mammalian polypeptide derived from NAIP that is capable of modulating apoptosis. The polypeptide may include at least two BIR domains as defined herein, preferably three BIR domains. In preferred embodiments, the NAIP amino acid sequence differs from the NAIP sequences of FIG. 6 or 7 by only conservative substitutions or differs from the sequences encoded by the nucleic acids of Seq. ID Nos. 1, 2, 21 or 23 by deletions of amino acids carboxy terminal to the BIR domains. In other preferred embodiments the recombinant protein decreases apoptosis relative to a control by at least 5%, more preferably by 25%.

In another aspect, the invention features a method of inhibiting apoptosis in a mammal wherein the method includes: providing nucleic acid encoding a NAIP polypeptide to a cell that is susceptible to apoptosis; wherein the nucleic acid is positioned for expression in the cell; NAIP gene is under the control of regulatory sequences suitable for controlled expression of the gene(s); and the NAIP transgene is expressed at a level sufficient to inhibit apoptosis relative to a cell lacking the NAIP transgene. The nucleic acid may encode all or part of a NAIP polypeptide. It may, for example, encode two or three BIR domains, but have a deletion of the carboxy-terminal amino acids. Preferably, the nucleic acid comprises sequences encoding exon 14a, exon 17, or both.

In a related aspect, the invention features a method of inhibiting apoptosis by producing a cell that has integrated, into its genome, a transgene that includes the NAIP gene, or a fragment thereof. The NAIP gene may be placed under the control of a promoter providing constitutive expression of the NAIP gene. Alternatively, the NAIP transgene may be placed under the control of a promoter that allows expression of the gene to be regulated by environmental stimuli. For example, the NAIP gene may be expressed using a tissue-specific or cell type-specific promoter, or by a promoter that is activated by the introduction of an external signal or agent, such as a chemical signal or agent. In preferred embodiments the mammalian cell is a lymphocyte, a neuronal cell, a glial cell, or a fibroblast. In other embodiments, the cell in an HIV-infected human, or in a mammal suffering from a neurodegenerative disease, an ischemic injury, a toxin-induced liver disease, or a myelodysplastic syndrome.

In a related aspect, the invention provides a method of inhibiting apoptosis in a mammal by providing an apoptosis-inhibiting amount of NAIP polypeptide. The NAIP polypeptide may be a full-length polypeptide, or it may be one of the fragments described herein.

In another aspect, the invention features a purified antibody that binds specifically to a NAIP protein. Such an antibody may be used in any standard immunodetection method for the detection, quantification, and purification of a NAIP polypeptide. Preferably, the antibody binds specifically to NAIP. The antibody may be a monoclonal or a polyclonal antibody and may be modified for diagnostic or for therapeutic purposes. The most preferable antibody binds the NAIP polypeptide sequences of Seq. ID Nos. 22 and/or 24, but not the NAIP polypeptide sequence disclosed in PCT/CA95/00581.

The antibodies of the invention may be prepared by a variety of methods. For example, the NAIP polypeptide, or antigenic fragments thereof, can be administered to an animal in order to induce the production of polyclonal antibodies. Alternatively, antibodies used as described herein may be monoclonal antibodies, which are prepared using hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981). The invention features antibodies that specifically bind human or murine NAIP polypeptides, or fragments thereof. In particular, the invention features "neutralizing" antibodies. By "neutralizing" antibodies is meant antibodies that interfere with any of the biological activities of the NAIP polypeptide, particularly the ability of NAIP to inhibit apoptosis. The neutralizing antibody may reduce the ability of NAIP polypeptides to inhibit apoptosis by, preferably 50%, more preferably by 70%, and most preferably by 90% or more. Any standard assay of apoptosis, including those described herein, may be used to assess potentially neutralizing antibodies.

In addition to intact monoclonal and polyclonal anti-NAIP antibodies, the invention features various genetically engineered antibodies, humanized antibodies, and antibody fragments, including F(ab')2, Fab', Fab, Fv and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., Nature Genetics 7:13–21, 1994).

Ladner (U.S. Pat. Nos. 4,946,778 and 4,704,692) describes methods for preparing single polypeptide chain antibodies. Ward et al. (Nature 341:544–546, 1989) describe the preparation of heavy chain variable domains, which they term "single domain antibodies," which have high antigen-binding affinities. McCafferty et al. (Nature 348:552–554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies.

In another aspect, the invention features a method of identifying a compound that modulates apoptosis. The method includes providing a cell expressing or capable of expressing a NAIP polypeptide, contacting the cell with a candidate compound, and monitoring the expression of the NAIP gene or a reporter gene linked to the NAIP gene regulatory sequences, or by monitoring NAIP biological activity. An alteration in the level of expression of the NAIP gene indicates the presence of a compound which modulates apoptosis. The compound may be an inhibitor or an enhancer of apoptosis. In various preferred embodiments, the mammalian cell is a myocardial cell, a fibroblast, a neuronal cell, a glial cell, a lymphocyte (T cell or B cell), or an insect cell.

In a related aspect, the invention features methods of detecting compounds that modulate apoptosis using the interaction trap technology and NAIP polypeptides, or fragments thereof, as a component of the bait. In preferred embodiments, the compound being tested as a modulator of apoptosis is also a polypeptide.

In a related aspect, the invention features a method for analyzing the anti-apoptotic effect of a candidate NAIP is provided comprising, i) providing an expression vector for the expression of the candidate NAIP; ii) transfecting mammalian cells with said expression vector; iii) inducing the transformed cells to undergo apoptosis; and iv) comparing the survival rate of the cells with appropriate mammalian cell controls.

In yet another aspect, the invention features a method for detecting the expression of NAIP in tissues comprising, i) providing a tissue or cellular sample; ii) incubating said sample with an anti-NAIP polyclonal or monoclonal antibody; and iii) visualizing the distribution of NAIP.

In another aspect, the invention features a method for diagnosing a cell proliferation disease, or an increased likelihood of such a disease, using a NAIP nucleic acid probe or NAIP antibody. Preferably, the disease is a cancer of the central nervous system. Most preferably, the disease is selected from the group consisting of neuroblastoma, meningioma, glialblastoma, astracystoma, neuroastrocytoma, promyelocytic leukemia, a HeLa-type carcinoma, chronic myelogenous leukemia (preferably using xiap or hiap-2 related probes), lymphoblastic leukemia (preferably using a xiap related probe), Burkitt's lymphoma, colorectal adenocarcinoma, lung carcinoma, and melanoma. Preferably, a diagnosis is indicated by a 2-fold increase in expression or activity, more preferably, at least a 10-fold increase in expression or activity.

In another aspect, the invention includes a method of treating a patient having deleterious levels apoptosis. Where the patient has more apoptosis than desirable or is otherwise deficient in normal NAIP, the method includes the step of administering to said patient a therapeutically effective amount of NAIP protein, NAIP nucleic acid, or a compound which enhances NAIP activity levels in a form which allows delivery to the cells which are undergoing more apoptosis than is therapeutically desirable. In one preferred embodiment, the cell having deleterious levels of apoptosis is a myocardial cell in a patient diagnosed with a cardiac condition.

Where insufficient levels of apoptosis are likely to occur, antisense NAIP nucleic acid, NAIP antibody, or a compound which otherwise decreases NAIP activity levels may be administered. Treatment of SMA is specifically excluded from the invention. Thus, apoptosis may be induced in a cell by administering to the cell a negative regulator of the NAIP-dependent anti-apoptotic pathway. The negative regulator may be, but is not limited to, a NAIP polypeptide fragment or purified NAIP specific antibody. For example, the antibody may bind to an epitope in any one of the three BIR domains. The negative regulator may also be a NAIP antisense RNA molecule.

Skilled artisans will recognize that a mammalian NAIP, or a fragment thereof (as described herein), may serve as an active ingredient in a therapeutic composition. This composition, depending on the NAIP or fragment included, may be used to modulate apoptosis and thereby treat any condition that is caused by a disturbance in apoptosis. Thus, it will be understood that another aspect of the invention described herein, includes the compounds of the invention in a pharmaceutically acceptable carrier.

As summarized above, a NAIP nucleic acid, polypeptide, or antibody may be used to modulate apoptosis. Furthermore, a NAIP nucleic acid, polypeptide, or antibody may be used in the discovery and/or manufacture of a medicament for the modulation of apoptosis.

By "NAIP gene" is meant a gene encoding a polypeptide having at least exon 14a or exon 17 FIG. 6 or 7, or the sequence of FIG. 5, Seq. ID No. 2, wherein at least 10 carboxy-terminal nucleic acids have been deleted to enhance activity, as described above. In preferred embodiments the NAIP gene encodes a polypeptide which is capable of inhibiting apoptosis or eliciting antibodies which specifically bind NAIP. In preferred embodiments the NAIP gene is a gene having about 50% or greater nucleotide sequence identity to the NAIP amino acid encoding sequences of FIG. 6 or 7. In another preferred embodiment, the NAIP gene encodes a fragment sufficient to inhibit apoptosis. Preferably, the region of sequence over which identity is measured is a region encoding exon 14a or exon 17. Mammalian NAIP genes include nucleotide sequences isolated from any mammalian source. Preferably, the mammal is a human.

The term "NAIP gene" is meant to encompass any NAIP gene, which is characterized by its ability to modulate apoptosis and encodes a polypeptide that has at least 20%, preferably at least 30%, and most preferably at least 50% amino acid sequence identity with the NAIP polypeptides shown in FIGS. 6 and 7. Specifically excluded is the full length sequence disclosed in PCT/CA95/00581 and shown in Seq. ID No. 1.

By "NAIP protein" or "NAIP polypeptide" is meant a polypeptide, or fragment thereof, encoded by a NAIP gene as described above.

By "modulating apoptosis" or "altering apoptosis" is meant increasing or decreasing the number of cells that would otherwise undergo apoptosis in a given cell population. Preferably, the cell population is selected from a group including T cells, neuronal cells, fibroblasts, myocardial cells, or any other cell line known to undergo apoptosis in a laboratory setting (e.g., the baculovirus infected insect cells). It will be appreciated that the degree of modulation provided by a NAIP or a modulating compound in a given assay will vary, but that one skilled in the art can determine the statistically significant change in the level of apoptosis which identifies a NAIP or a compound which modulates a NAIP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of more than two amino acids, regardless of post-translational modification such as glycosylation or phosphorylation.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a NAIP polypeptide that is at least 75%, more preferably at least 90%, and most preferably at least 99%, by weight, pure. A substantially pure NAIP polypeptide may be obtained, for example, by extraction from a natural source (e.g. a fibroblast, neuronal cell, or lymphocyte) by expression of a recombinant nucleic acid encoding a NAIP polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes. By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a NAIP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., a NAIP polypeptide, a recombinant protein or a RNA molecule).

By "reportor gene" is meant a gene whose expression may be assayed; such genes include, without limitation, glucuronidase (GUS), luciferase, chloramphenicol transacetylase (CAT), and β-galactosidase, and green fluorescent protein (GFP).

By "promoter" is meant minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins are bound to the regulatory sequences).

By "conserved region" is meant any stretch of six or more contiguous amino acids exhibiting at least 30%, preferably 50%, and most preferably 70% amino acid sequence identity between two or more of the NAIP family members, (e.g., between human NAIP and murine NAIP).

By "carboxy terminal amino acids of NAIP" is meant the amino acids of carboxy terminal to the three BIR domains of the NAIP gene. For example, the amino acids encoded beyond nucleic acid 1360 of Seq. ID. No. 21 are carboxy terminal.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "antisense," as used herein in reference to nucleic acids, is meant a nucleic acid sequence, regardless of length, that is complementary to the coding strand of a gene.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a NAIP specific antibody. A purified antibody may be obtained, for example, by affinity chromatography using recombinantly-produced protein or conserved motif peptides and standard techniques.

By "specifically binds" is meant an antibody that recognizes and binds a protein but that does not substantially recognize and bind other molecules in a sample, e.g., a biological sample, that naturally includes protein. The preferred antibody binds to the NAIP peptide sequence of sequence ID No. 2 but does not bind to the NAIP sequence disclosed in PCT/CA 95/00581.

Other features and advantages of the invention will be apparent from the following description of the preferred embodiments thereof, and from the claims.

BRIEF DESCRIPTION OF THE DRAWINGS

Various aspects of the invention are described with respect to the drawings wherein:

FIG. 5 shows the sequences obtained in 2 separate sequencings of the NAIP gene.

FIG. 6 shows a preferred NAIP cDNA (SEQ ID No. 21) sequence and the predicted NAIP polypeptide sequence.

FIG. 7 shows a NAIP sequence including the intron-exon boundaries. (Seq. ID No. 23).

DETAILED DESCRIPTION OF THE PREFERRED EMBODIMENT

Figure 1A:
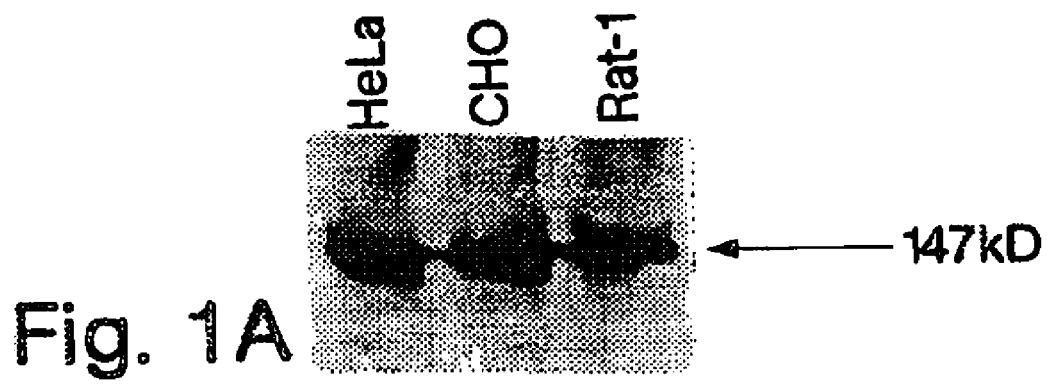
FIG. 1. shows expression of NAIP in HeLa, CHO and Rat-1 pooled stable lines and adenovirus infected cells analysed by Western blotting (A–D) and immunofluorescence. A–B are cells infected with adenovirus encoding NAIP-myc detected by a mouse anti-myc monoclonal antibody or by a rabbit anti human NAIP polyclonal antibody. C cells infected with adenovirus encoding NAIP detected by the NAIP polyclonal antibody. D expression of myc-NAIP in representative pooled cell lines by immunofluorescence detected with antibodies against myc. E–F rat-1 NAIP transfectants detected by E anti-myc and F anti-NAIP antibodies.

Although the precise site and mechanism of NAIP's anti-apoptotic effect is unknown, it is now demonstrated that NAIP is clearly involved in apoptotic pathways in mammalian cells. In addition, immunofluorescence localization indicates that NAIP is expressed in motor, but not sensory neurons. These findings are in keeping with the protein acting as a negative regulator of apoptosis, most particularly neuronal apoptosis and, when deficient or absent, contributes to the neurodegenerative phenotypes such as SMA and ALS.

I. The NAIP Gene

There are two nearly identical copies of NAIP on 5q13.1. The complete NAIP gene, shown in FIG. 7, contains 18 exons (1 to 14, and 14a to 17) and spans an estimated 90 kb of genomic DNA. (Other intermediate sequences obtained are shown in FIGS. 5 and 6). The NAIP coding region spans 4212 nucleotides resulting in a predicted gene product of 1404 amino acids (Seq. ID No. 22). The total length of the NAIP gene spans 6228 nucleotides (Seq. ID No. 23) with a 395 nucleotide 5' UTR and a 1621 nucleotide 3' UTR. The complete sequence, Sequence ID No. 2, allows one skilled in the art to develop probes and primers for the identification of homologous sequences and for the identification of mutations within the DNA. Both 5' and 3' regions may also prove useful as encoding binding sites for agents which may up or down-regulate the gene further delineating the NAIP pathway and function. The sequences identified as Seq. ID No. 2 and 23 are also useful for protein expression in appropriate vectors and hosts to produce NAIP and study its function as well as to develop antibodies. Sequencing of the PAC 125D9 154 kb, which was identified as a likely site of the SMA gene, resulted in the identification of the NAIP sequence shown in FIG. 5, Seq. ID No. 1. An additional coding sequence, exon 14a, has since been identified and is provided herewith. The NAIP DNA sequence containing exon 14a appears to be a predominant gene isoform which is not deleted or mutated in SMA patients. The techniques and primers used for the isolation and application of exon 14a from the human fetal spinal cord cDNA libraries was as described for the identification of the other exons and detailed in Example 4. Additional screening of cDNA libraries combined with analysis of PAC 125D9 genomic DNA sequence has resulted in the identification of a novel 3' end of NAIP which includes additional exon 17 sequence.

II. Synthesis of NAIP

The characteristics of the cloned NAIP gene sequence may be analyzed by introducing the sequence into various cell types or using in vitro extracellular systems. The function of the NAIP may then be examined under different physiological conditions. The NAIP DNA sequence may be manipulated in studies to understand the expression of the gene and gene product. Alternatively, cell lines may be produced which overexpress the gene product allowing purification of NAIP for biochemical characterization, large-scale production, antibody production, and patient therapy.

For protein expression, eukaryotic and prokaryotic expression systems may be generated in which the NAIP gene sequence is introduced into a plasmid or other vector which is then introduced into living cells. Constructs in which the NAIP cDNA sequence containing the entire open reading frame inserted in the correct orientation into an expression plasmid may be used for protein expression. Alternatively, portions of the sequence, including wild-type or mutant NAIP sequences, may be inserted. Prokaryotic and eukaryotic expression systems allow various important functional domains of the protein to be recovered as fusion proteins and then used for binding, structural and functional studies and also for the generation of appropriate antibodies. If a NAIP increases apoptosis, it may be desirable to express that protein under control of an inducible promotor.

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Some vectors contain selectable markers such as neomycin resistance that permit isolation of cells by growing them under selective conditions. Stable long-term vectors may be maintained as freely replicating entities by using regulatory elements of viruses. Cell lines may also be produced which have integrated the vector into the genomic DNA and in this manner the gene product is produced on a continuous basis.

Expression of foreign sequences in bacteria such as *E. coli* require the insertion of the NAIP sequence into an expression vector, usually a bacterial plasmid. This plasmid vector contains several elements such as sequences encoding a selectable marker that assures maintenance of the vector in the cell, a controllable transcriptional promoter (ie, lac) which upon induction can produce large amounts of mRNA from the cloned gene, translational control sequences and a polylinker to simplify insertion of the gene in the correct orientation within the vector. In a simple *E. coli* expression vector utilizing the lac promoter, the expression vector plasmid contains a fragment of the *E. coli* chromosome containing the lac promoter and the neighboring lacZ gene. In the presence of the lactose analog IPTG, RNA polymerase normally transcribes the lacZ gene producing lacZ mRNA which is translated into the encoded protein, β-galactosidase. The lacZ gene can be cut out of the expression vector with restriction enzymes and replaced by NAIP gene sequence. When this resulting plasmid is transfected into *E. coli*, addition of IPTG and subsequent transcription from the lac promoter produces NAIP mRNA, which is translated into NAIP.

Once the appropriate expression vector containing the NAIP gene is constructed it is introduced into an appropriate *E. coli* strain by transformation techniques including calcium phosphate transfection, DEAE-dextran transfection, electroporation, microinjection, protoplast fusion and liposome-mediated transfection.

The host cell which may be transfected with the vector of this invention may be selected from the group consisting of *E. coli, Pseudomonas, bacillus subtillus,* or other bacili, other bacteria, yeast, fungi, insect (using baculoviral vectors for expression), mouse or other animal or human tissue cells. Mammalian cells can also be used to express the NAIP protein using a vaccinia virus expression system.

In vitro expression of proteins encoded by cloned DNA is also possible using the T7 late-promoter expression system. This system depends on the regulated expression of T7 RNA polymerase which is an enzyme encoded in the DNA of bacteriophage T7. The T7 RNA polymerase transcribes DNA beginning within a specific 23-bp promotor sequence called the T7 late promoter. Copies of the T7 late promoter are located at several sites on the T7 genome, but none is present in *E. coli* chromosomal DNA. As a result, in T7 infected cells, T7 RNA polymerase catalyzes transcription of viral genes but not of *E. coli* genes. In this expression system recombinant *E. coli* cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed *E. coli* cells, large amounts of T7 RNA polymerase are produced. The polymerase then binds to the T7 late promoter on the plasmid expression vectors, catalyzing transcription of the inserted cDNA at a high rate. Since each *E. coli* cell contains many copies of the expression vector, large amounts of mRNA corresponding to the cloned cDNA can be produced in this system and the resulting protein can be radioactively labelled. Plasmid vectors containing late promoters and the corresponding RNA polymerases from related bacteriophages such as T3, T5 and SP6 may also be used for in vitro production of proteins from cloned DNA. *E. coli* can also be used for expression by infection with M13 Phage mGPI-2. *E. coli* vectors can also be used with phage lambda regulatory sequences, by fusion protein vectors, by maltose-binding protein fusions, and by glutathione-S-transferase fusion proteins.

A preferred expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (Mol. Cell Biol. 5:3610–3616, 1985).

Eukaryotic expression systems permit appropriate post-translational modifications to expressed proteins. This allows for studies of the NAIP gene and gene product including determination of proper expression and post-translational modifications for biological activity, identifying regulatory elements located in the 5' region of the NAIP gene and their role in tissue regulation of protein expression. It also permits the production of large amounts of normal and mutant proteins for isolation and purification, to use cells expressing NAIP as a functional assay system for antibodies generated against the protein, to test the effectiveness of pharmacological agents or as a component of a signal transduction system, to study the function of the normal complete protein, specific portions of the protein, or of naturally occurring polymorphisms and artificially produced mutated proteins. The NAIP DNA sequence can be altered using procedures such as restriction enzyme digestion, DNA polymerase fill-in, exonuclease deletion, terminal deoxynucleotide transferase extension, ligation of synthetic or cloned DNA sequences and site-directed sequence alteration using specific oligonucleotides together with PCR.

A NAIP may be produced by a stably-transfected mammalian cell line. A number of vectors suitable for stable transfection of mammalian cells are available to the public, e.g., see Pouwels et al. (supra), as are methods for constructing such cell lines (see e.g., Ausubel et al. (supra). In one example, cDNA encoding a NAIP is cloned into an expression vector that includes the dihydrofolate reductase (DHFR) gene. Integration of the plasmid and, therefore, integration of the NAIP-encoding gene into the host cell chromosome is selected for by inclusion of 0.01–300 $\mu$M methotrexate in the cell culture medium (as described, Ausubel et al., supra). This dominant selection can be accomplished in most cell types. Recombinant protein expression can be increased by DHFR-mediated amplification of the transfected gene.

Methods for selecting cell lines bearing gene amplifications are described in Ausubel et al. (supra). These methods generally involve extended culture in medium containing gradually increasing levels of methotrexate. The most commonly used DHFR-containing expression vectors are pCVSEII-DHFR and pAdD26SV(A) (described in Ausubel et al., supra). The host cells described above or, preferably, a DHFR-deficient CHO cell line (e.g., CHO DHFR cells, ATCC Accession No. CRL 9096) are among those most preferred for DHFR selection of a stably-transfected cell line or DHFR-mediated gene amplification.

Once the recombinant protein is expressed, it is isolated by, for example, affinity chromatography. In one example, an anti-NAIP antibody, which may be produced by the methods described herein, can be attached to a column and used to isolate the NAIP protein. Lysis and fractionation of NAIP-harboring cells prior to affinity chromatography may be performed by standard methods (see e.g., Ausubel et al., supra). Once isolated, the recombinant protein can, if desired, be purified further by e.g., by high performance liquid chromatography (HPLC; e.g., see Fisher, *Laboratory Techniques In Biochemistry And Molecular Biology*, Work and Burdon, Eds., Elsevier, 1980).

Polypeptides of the invention, particularly short NAIP fragments, can also be produced by chemical synthesis (e.g., by the methods described in *Solid Phase Peptide Synthesis*, 2nd ed., 1984 The Pierce Chemical Co., Rockford, Ill.). These general techniques of polypeptide expression and purification can also be used to produce and isolate useful NAIP fragments or analogs, as described herein.

Those skilled in the art of molecular biology will understand that a wide variety of expression systems may be used to produce the recombinant protein. The precise host cell used is not critical to the invention. The NAIP protein may be produced in a prokaryotic host (e.g., *E. coli*) or in a eukaryotic host (e.g., *S. cerevisiae*, insect cells such as Sf21 cells, or mammalian cells such as COS-1, NIH 3T3, or HeLa cells). These cells are publically available, for example, from the American Type Culture Collection, Rockville, Md.; see also Ausubel et al., *Current Protocols in Molecular Biology*, John Wiley & Sons, New York, N.Y., 1994). The method of transduction and the choice of expression vehicle will depend on the host system selected. Transformation and transfection methods are described, e.g., in Ausubel et al. (supra), and expression vehicles may be chosen from those provided, e.g. in *Cloning Vectors: A Laboratory Manual* (P. H. Pouwels et al., 1985, Supp. 1987).

III. Testing for the Presence of NAIP Biological Activity

To analyze the effect of NAIP on apoptosis in a first approach, expression plasmids alone or encoding nearly full length NAIP or Bcl-2 (a protein which functions under normal conditions to protect cells against apoptosis) were transfected into CHO, Rat-1 and HeLa cells followed by G418 selection. Initially, a NAIP cDNA was isolated by probing a human fetal brain cDNA library with a genomic DNA insert of a cosmid from the constructed cosmid library, and a cDNA fragment encoding most of the three BIR domains corresponding to the NAIP gene sequence was isolated.

IV. Cellular Distribution of NAIP

We have looked at the distribution of NAIP using immunofluorescence of labelled antibodies and find NAIP is expressed in at least the following tissues: motor neurons, myocardial cells, liver, placenta and CNS.

V. NAIP Fragments

The BIR domains of NAIP appear to be both necessary and sufficient for NAIP biological activity. Surprisingly, we have reason to believe carboxy terminal deletions of NAIP amino acids actually enhances inhibition of apoptosis by NAIP. Deletions may be up to the end of the last NAIP BIR domain (i.e., the third), but need not delete the entire region carboxy terminal to the third BIR domains.

VI. NAIP Antibodies

In order to prepare polyclonal antibodies, NAIP, fragments of NAIP, or fusion proteins containing defined portions or all of the NAIP protein can be synthesized in bacteria by expression of corresponding DNA sequences in a suitable cloning vehicle. Fusion proteins are commonly used as a source of antigen for producing antibodies. Two widely used expression systems for *E. coli* are lacZ fusions using the pUR series of vectors and trpE fusions using the pATH vectors. The protein can then be purified, coupled to a carrier protein and mixed with Freund's adjuvant (to help stimulate the antigenic response by the rabbits) and injected into rabbits or other laboratory animals. Alternatively, protein can be isolated from NAIP expressing cultured cells. Following booster injections at bi-weekly intervals, the rabbits or other laboratory animals are then bled and the sera isolated. The sera can be used directly or purified prior to use, by various methods including affinity chromatography employing Protein A-Sepharose, Antigen Sepharose, Anti-mouse-Ig-Sepharose. The sera can then be used to probe protein extracts from tissues run on a polyacrylamide gel to identify the NAIP protein. Alternatively, synthetic peptides can be made to the antigenic portions of the protein and used to innoculate the animals.

In order to generate peptide for use in making NAIP-specific antibodies, a NAIP coding sequence (i.e., amino acid fragments shown in Seq. ID Nos. 22 and 24) can be expressed as a C-terminal fusion with glutathione S-transferase (GST; Smith et al., Gene 67:31–40, 1988). The fusion protein can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titres are monitored by Western blot and immunoprecipitation analyses using the thrombin-cleaved NAIP fragment of the GST-NAIP fusion protein. Immune sera are affinity purified using CNBr-Sepharose-coupled NAIP protein. Antiserum specificity is determined using a panel of unrelated GST proteins (including GSTp53, Rb, HPV-16 E6, and E6-AP) and GST-trypsin (which was generated by PCR using known sequences).

It is also understood by those skilled in the art that monoclonal NAIP antibodies may be produced by culturing cells actively expressing the protein or isolated from tissues. The cell extracts, or recombinant protein extracts, containing the NAIP protein, may for example, be injected in Freund's adjuvant into mice. After being injected, the mice spleens may be removed and resuspended in phosphate buffered saline (PBS). The spleen cells serve as a source of lymphocytes, some of which are producing antibody of the appropriate specificity. These are then fused with a permanently growing myeloma partner cells, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant methods in which plasmids are generated which express the desired monoclonal antibody fragment(s) in a suitable host.

As an alternate or adjunct immunogen to GST fusion proteins, peptides corresponding to relatively unique hydrophilic regions of NAIP may be generated and coupled to keyhole limpet hemocyanin (KLH) through an introduced C-terminal lysine. Antiserum to each of these peptides is similarly affinity purified on peptides conjugated to BSA, and specificity is tested by ELISA and Western blotting using peptide conjugates, and by Western blotting and immunoprecipitation using NAIP expressed as a GST fusion protein.

Alternatively, monoclonal antibodies may be prepared using the NAIP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridonas*, Elsevier, New York, N.Y., 1981; Ausubel et al., supra). Once produced, monoclonal antibodies are also tested for specific NAIP recognition by Western blot or immunoprecipitation analysis (by the methods described in Ausubel et al., supra).

Antibodies that specifically recognize NAIP (or fragments of NAIP), such as those described herein containing one or more BIR domains are considered useful in the invention. They may, for example, be used in an immunoassay to monitor NAIP expression levels or to determine the subcellular location of a NAIP or NAIP fragment produced by a mammal. Antibodies that inhibit NAIP described herein may be especially useful in inducing apoptosis-in cells undergoing undesirable proliferation.

Preferably, antibodies of the invention are produced using NAIP sequence that does not reside within highly conserved regions, and that appears likely to be antigenic, as analyzed by criteria such as those provided by the Peptide structure program (Genetics Computer Group Sequence Analysis Package, Program Manual for the GCG Package, Version 7, 1991) using the algorithm of Jameson and Wolf (CABIOS 4:181, 1988). These fragments can be generated by standard techniques, e.g. by the PCR, and cloned into the pGEX expression vector (Ausubel et al., supra). Fusion proteins are expressed in *E. coli* and purified using a glutathione agarose affinity matrix as described in Ausubel et al. (supra). In order to minimize the potential for obtaining antisera that is non-specific, or exhibits low-affinity binding to NAIP, two or three fusions are generated for each protein, and each fusion is injected into at least two rabbits. Antisera are raised by injections in series, preferably including at least three booster injections.

VII. Use of NAIP Antibodies

Antibodies to NAIP may be used, as noted above, to detect NAIP or inhibit the protein. In addition, the antibodies coupled to compounds for diagnostic and/or therapeutic uses such as radionucleotides for imaging and therapy and liposomes for the targeting of compounds to a specific tissue location.

VIII. Detection of NAIP Gene Expression

As noted, the antibodies described above may be used to monitor NAIP protein expression. In addition, in situ hybridization is a method which may be used to detect the expression of the NAIP gene. In situ hybridization relies upon the hybridization of a specifically labelled nucleic acid probe to the cellular RNA in individual cells or tissues. Therefore, it allows the identification of mRNA within intact tissues, such as the brain. In this method. oligonucleotides or cloned nucleotide (RNA or DNA) fragments corresponding to unique portions of the NAIP gene are used to detect specific mRNA species, e.g., in the brain. In this method a rat is anesthetized and transcardially perfused with cold PBS, followed by perfusion with a formaldehyde solution. The brain or other tissues is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the primer is made by nick translation and incubated with the sectioned brain tissue. After incubation and air drying, the labelled areas are visualized by autoradiography. Dark spots on the tissue sample indicate hybridization of the probe with NAIP mRNA which demonstrates the expression of the protein.

IX. Identification of Molecules that Modulate NAIP Protein Expression

NAIP cDNAs may be used to facilitate the identification of molecules that increase or decrease NAIP expression. In one approach, candidate molecules are added, in varying concentration, to the culture medium of cells expressing NAIP mRNA. NAIP expression is then measured, for example, by Northern blot analysis (Ausubel et al., supra) using a NAIP cDNA, or cDNA or RNA fragment, as a hybridization probe. The level of NAIP expression in the presence of the candidate molecule is compared to the level of NAIP expression in the absence of the candidate molecule, all other factors (e.g. cell type and culture conditions) being equal.

The effect of candidate molecules on NAIP-mediated apoptosis may, instead, be measured at the level of translation by using the general approach described above with standard protein detection techniques, such as Western blotting or immunoprecipitation with a NAIP-specific antibody (for example, the NAIP antibody described herein).

Compounds that modulate the level of NAIP may be purified, or substantially purified, or may be one component of a mixture of compounds such as an extract or supernatant obtained from cells (Ausubel et al., supra). In an assay of a mixture of compounds, NAIP expression is tested against progressively smaller subsets of the compound pool (e.g., produced by standard purification techniques such as HPLC or FPLC) until a single compound or minimal number of effective compounds is demonstrated to modulate NAIP expression.

Compounds may also be screened for their ability to modulate NAIP apoptosis inhibiting activity. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the activity of NAIPs is to screen for compounds that interact physically with a given NAIP polypeptide. These compounds may be detected by adapting interaction trap expression systems known in the art. These systems detect protein interactions using a transcriptional activation assay and are generally described by Gyuris et al. (Cell 75:791–803, 1993) and Field et al., Nature 340:245–246, 1989), and are commercially available from Clontech (Palo Alto, Calif.). In addition, PCT Publication WO 95/28497 describes an interaction trap assay in which proteins involved in apoptosis, by virtue of their interaction with Bcl-2, are detected. A similar method may be used to identify proteins and other compounds that interact with NAIP.

Compounds or molecules that function as modulators of NAIP-mediated cell death may include peptide and non-peptide molecules such as those present in cell extracts, mammalian serum, or growth medium in which mammalian cells have been cultured.

A molecule that promotes an increase in NAIP expression or NAIP activity is considered particularly useful in the invention; such a molecule may be used, for example, as a therapeutic to increase cellular levels of NAIP and thereby exploit the ability of NAIP polypeptides to inhibit apoptosis.

A molecule that decreases NAIP activity (e.g., by decreasing NAIP gene expression or polypeptide activity) may be used to decrease cellular proliferation. This would be advantageous in the treatment of neoplasms or other cell proliferative diseases.

Molecules that are found, by the methods described above, to effectively modulate NAIP gene expression or polypeptide activity may be tested further in animal models. If they continue to function successfully in an in vivo setting, they may be used as therapeutics to either inhibit or enhance apoptosis, as appropriate.

X. Therapies

Therapies may be designed to circumvent or overcome an NAIP gene defect or inadequate NAIP gene expression, and thus moderate and possibly prevent apoptosis. The NAIP gene is expressed in the liver, myocardium, and placenta, as well as in the CNS. Hence, in considering various therapies, it is understood that such therapies may be targeted at tissue other than the brain, such as the liver, myocardium, and any other tissues subsequently demonstrated to express NAIP.

a) Protein Therapy

Treatment or prevention of apoptosis can be accomplished by replacing mutant or insufficient NAIP protein with normal protein, by modulating the function of mutant protein, or by delivering normal NAIP protein to the appropriate cells. Once the biological pathway of the NAIP protein has been completely understood, it may also be possible to modify the pathophysiologic pathway (e.g., a signal transduction pathway) in which the protein participates in order to correct the physiological defect.

To replace a mutant protein with normal protein, or to add, protein to cells which no longer express sufficient NAIP, it is necessary to obtain large amounts of pure NAIP from cultured cell systems which can express the protein. Delivery of the protein to the affected tissues can then be accomplished using appropriate packaging or administrating systems. Alternatively, small molecule analogs may be used and administered to act as NAIP agonists and in this manner produce a desired physiological effect. Methods for finding such molecules are provided herein.

b) Gene Therapy

Gene therapy is another potential therapeutic approach in which normal copies of the NAIP gene are introduced into selected tissues to successfully code for normal and abundant protein in affected cell types. The gene must be delivered to those cells in a form in which it can be taken up and code for sufficient protein to provide-effective function. Alternatively, in some mutants it may be possible to prevent apoptosis by introducing another copy of the homologous gene bearing a second mutation in that gene or to alter the mutation, or use another gene to block any negative effect.

Transducing retroviral vectors can be used for somatic cell gene therapy especially because of their high efficiency of infection and stable integration and expression. The targeted cells however must be able to divide and the expression of the levels of normal protein should be high. The full length NAIP gene, or portions thereof, can be cloned into a retroviral vector and driven from its endogenous promoter or from the retroviral long terminal repeat or from a promoter specific for the target cell type of interest (such as neurons). Other viral vectors which can be used include adeno-associated virus, vaccinia virus, bovine papilloma virus, or a herpes virus such as Epstein-Barr virus.

Gene transfer could also be achieved using non-viral means requiring infection iii vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can be employed to explore NAIP gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/ transport/translation and/or stability of the target NAIP mRNA. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

Transplantation of normal genes into the affected cells of a patient can also be useful therapy. In this procedure, normal NAIP is transferred into a cultivatable cell type, either exogenously or endogenously to the patient. These cells are then injected serotologically into the targeted tissue(s).

Retroviral vectors, adenoviral vectors, adeno associated viral vectors, or other viral vectors with the appropriate tropism for cells likely to be involved in apoptosis (for example, epithelial cells) may be used as a gene transfer delivery system for a therapeutic NAIP gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, current opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; Miller et al., Biotechniques 7:980–990, 1989; Le Gal La Salle et al., Science 259:988–990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Non-viral approaches may also be employed for the introduction of therapeutic DNA into cells otherwise predicted to undergo apoptosis. For example, NAIP may be introduced into a neuron or a T cell by lipofection (Felgner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983),asialorosonucoid-polylysine conjugation (Wu et al., J. Biol. Chem. 263:14621, 1988; Wu et al., J. Biol. Chem. 264:16985, 1989); or, less preferably, microinjection under surgical conditions (Wolff et al., Science 247:1465, 1990).

For any of the methods of application described above, the therapeutic NAIP DNA construct is preferably applied to the site of the predicted apoptosis event (for example, by injection). However, it may also be applied to tissue in the vicinity of the predicted apoptosis event or to a blood vessel supplying the cells predicted to undergo apoptosis.

In the constructs described, NAIP cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, T cells, or B cells may be used to direct NAIP expression. The enhancers used could include, without limitation, those that are characterized as tissue- or cell-specific in their expression. Alternatively, if a NAIP genomic clone is used as a therapeutic construct (for example, following its isolation by hybridization with the NAIP cDNA described above), regulation may be mediated by the cognate regulatory sequences or, if desired, by regulatory sequences derived from a heterologous source, including any of the promoters or regulatory elements described above.

Less preferably, NAIP gene therapy is accomplished by direct administration of the NAIP mRNA or antisense NAIP mRNA to a cell that is expected to undergo apoptosis. The mRNA may be produced and isolated by any standard technique, but is most readily produced by in vitro transcription using a NAIP cDNA under the control of a high efficiency promoter (e.g., the T7 promoter). Administration of NAIP antisense or mRNA to cells mRNA can be carried out by any of the methods for direct nucleic acid administration described above.

Ideally, the production of NAIP protein by any gene therapy approach will result in cellular levels of NAIP that are at least equivalent to the normal, cellular level of NAIP in an unaffected cell. Treatment by any NAIP-mediated gene therapy approach may be combined with more traditional therapies.

Another therapeutic approach within the invention involves administration of recombinant NAIP protein, either directly to the site of a predicted apoptosis event (for example, by injection) or systemically (for example, by any conventional recombinant protein administration technique). The dosage of NAIP depends on a number of factors, including the size and health of the individual patient, but, generally, between [0.1 mg and 100 mg] inclusive are administered per day to an adult in any pharmaceutically acceptable formulation.

XI. Administration of NAIP Polypeptides, NAIP Genes, or Modulators of NAIP Synthesis or Function A NAIP protein, gene, or modulator may be administered within a pharmaceutically-acceptable diluent, carrier, or excipient, in unit dosage form. Conventional pharmaceutical practice may be employed to provide suitable formulations or compositions to administer NAIP to patients suffering from a disease that is caused by excessive apoptosis. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for NAIP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a NAIP protein, gene, or modulatory compound may be combined with more traditional therapies for the disease such as surgery, steroid therapy, or chemotherapy for autoimmune disease; antiviral therapy for AIDS; and tissue plasminogen activator (TPA) for ischemic injury.

XII. Detection of Conditions Involving Altered Apoptosis

NAIP polypeptides and nucleic acid sequences find diagnostic use in the detection or monitoring of conditions involving aberrant levels of apoptosis. For example, decrease expression of NAIP may be correlated with enhanced apoptosis in humans (see XII, below). Accordingly, a decrease or increase in the level of NAIP production may provide an indication of a deleterious condition. Levels of NAIP expression may be assayed by any standard technique. For example, NAIP expression in a biological sample (e.g., a biopsy) may be monitored by standard Northern blot analysis or may be aided by PCR (see, e.g., Ausubel et al., supra; *PCR Technology: Principles and Applications for DNA Amplification*, H. A. Ehrlich, Ed. Stockton Press, N.Y.; Yap et al. Nucl. Acids. Res. 19:4294, 1991).

Alternatively, a biological sample obtained from a patient may be analyzed for one or more mutations in the NAIP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant NAIP detection, and each is well known in the art; examples of particular techniques are described, without limitation, in Orita et al., Proc. Natl. Acad. Sci. USA 86:2766–2770, 1989; Sheffield et al., Proc. Natl. Acad. Sci. USA 86:232–236, 1989).

In yet another approach, immunoassays are used to detect or monitor NAIP protein in a biological sample. NAIP specific polyclonal or monoclonal antibodies (produced as described above) may be used in any standard immunoassay format (e.g., ELISA, Western blot, or RIA) to measure NAIP polypeptide levels. These levels would be compared to wild-type NAIP levels, with a decrease in NAIP production indicating a condition involving increased apoptosis. Examples of immunoassays are described, e.g., in Ausubel et al., supra. Immunohistochemical techniques may also be utilized for NAIP detection. For example, a tissue sample may be obtained from a patient, sectioned, and stained for the presence of NAIP using an anti-NAIP antibody and any standard detection system (e.g., one which includes a secondary antibody conjugated to horseradish peroxidase). General guidance regarding such techniques can be found in, e.g., Bancroft and Stevens (*Theory and Practice of Histological Technigues*, Churchill Livingstone, 1982) and Ausubel et al. (supra).

In one preferred example, a combined diagnostic method may be employed that begins with an evaluation of NAIP protein production (for example, by immunological techniques or the protein truncation test (Hogerrorst et al., Nature Genetics 10:208–212, 1995) and also includes a nucleic acid-based detection technique designed to identify more subtle NAIP mutations (for example, point mutations). As described above, a number of mismatch detection assays are available to those skilled in the art, and any preferred technique may be used. Mutations in NAIP may be detected that either result in loss of NAIP expression or loss of NAIP biological activity. In a variation of this combined diagnostic method, NAIP biological activity is measured as anti-apoptotic activity using any appropriate apoptosis assay system (for example, those described herein).

Mismatch detection assays also provide an opportunity to diagnose a NAIP-mediated predisposition to diseases caused by inappropriate apoptosis. For example, a patient heterozygous for a NAIP mutation may show no clinical symptoms and yet possess a higher than normal probability of developing one or more types of neurodegenerative, myelodysplastic or having severe sequelae to an ischemic event. Given this diagnosis, a patient may take precautions to minimize their exposure to adverse environmental factors (for example, UV exposure or chemical mutagens) and to carefully monitor their medical condition (for example, through frequent physical examinations). This type of NAIP diagnostic approach may also be used to detect NAIP mutations in prenatal screens. The NAIP diagnostic assays described above may be carried out using any biological sample (for example, any biopsy sample or other tissue) in which NAIP is normally expressed. Identification of a mutant NAIP gene may also be assayed using these sources for test samples.

Alternatively, a NAIP mutation, particularly as part of a diagnosis for predisposition to NAIP-associated degenerative disease, may be tested using a DNA sample from any cell, for example, by mismatch detection techniques. Preferably, the DNA sample is subjected to PCR amplification prior to analysis.

XIII. Preventative Anti-Apoptotic Therapy

In a patient diagnosed to be heterozygous for a NAIP mutation or to be susceptible to NAIP mutations (even if those mutations do not yet result in alteration or loss of NAIP biological activity), or a patient diagnosed with a degenerative disease (e.g., motor neuron degenerative diseases such as SMA or ALS diseases), or diagnosed as HIV positive, any of the above therapies may be administered before the occurrence of the disease phenotype. For example, the therapies may be provided to a patient who is HIV positive but does not yet show a diminished T cell count or other overt signs of AIDS. In particular, compounds shown to increase NAIP expression or NAIP biological activity may be administered by any standard dosage and route of administration (see above). Alternatively, gene therapy using a NAIP expression construct may be undertaken to reverse or prevent the cell defect prior to the development of the degenerative disease.

The methods of the instant invention may be used to reduce or diagnose the disorders described herein in any mammal, for example, humans, domestic pets, or livestock. Where a non-human mammal is treated or diagnosed, the NAIP polypeptide, nucleic acid, or antibody employed is preferably specific for that species.

XV. Identification of Additional NAIP Genes

Standard techniques, such as the polymerase chain reaction (PCR) and DNA hybridization, may be used to clone additional NAIP homologues in other species. Southern blots of murine genomic DNA hybridized at low stringency with probes specific for human NAIP reveal bands that correspond to NAIP and/or related family members. Thus, additional NAIP sequences may be readily identified using low stringency hybridization. Examples of murine and human NAIP-specific primers, which may be used to clone additional genes by RT-PCR.

XVI. Characterization of NAIP Activity and Intracellular Localization Studies

The ability of NAIP to modulate apoptosis can be defined in in vitro systems in which alterations of apoptosis can be detected. Mammalian expression constructs carrying NAIP cDNAs, which are either full-length or truncated, can be introduced into cell lines such as CHO, NIH 3T3, HL60, Rat-1, or Jurkat cells. In addition, SF21 insect cells may be used, in which case the NAIP gene is preferentially expressed using an insect heat shock promotor. Following transfection, apoptosis can be induced by standard methods, which include serum withdrawal, or application of staurosporine, menadione (which induces apoptosis via free radical formation), or anti-Fas antibodies. As a control, cells are cultured under the same conditions as those induced to undergo apoptosis, but either not transfected, or transfected with a vector that lacks a NAIP insert. The ability of each NAIP construct to inhibit apoptosis upon expression can be quantified by calculating the survival index of the cells, i.e., the ratio of surviving transfected cells to surviving control cells. These experiments can confirm the presence of apoptosis inhibiting activity and, as discussed below, can also be used to determine the functional region(s) of a NAIP. These assays may also be performed in combination with the application of additional compounds in order to identify compounds that modulate apoptosis via NAIP expression.

XVII. Examples of Additional Apoptosis Assays

Specific examples of apoptosis assays are also provided in the following references. Assays for apoptosis in lymphocytes are disclosed by: Li et al., "Induction of apoptosis in uninfected lymphocytes by HIV-1 Tat protein", Science 268:429–431, 1995; Gibellini et al., "Tat-expressing Jurkat cells show an increased resistance to different apoptotic stimuli, including acute human immunodeficiency virus-type 1 (HIV-1) infection", Br. J. Haematol. 89:24–33, 1995; Martin et al., "HIV-1 infection of human $CD4^+$ T cells in vitro. Differential induction of apoptosis in these cells." J. Immunol. 152:330–42, 1994; Terai et al., "Apoptosis as a mechanism of cell death in cultured T lymphoblasts acutely infected with HIV-1", J. Clin Invest. 87:1710–5, 1991; Dhein et al., "Autocrine T-cell suicide mediated by APO-1/(Fas/CD95)11, Nature 373:438–441, 1995; Katsikis et al., "Fas antigen stimulation induces marked apoptosis of T lymphocytes in human immunodeficiency virus-infected individuals", J. Exp. Med. 1815:2029–2036, 1995; Westendorp et al., Sensitization of T cells to CD95-mediated apoptosis by HIV-1 Tat and gp12O", Nature 375:497, 1995; DeRossi et al., Virology 198:234–44, 1994.

Assays for apoptosis in fibroblasts are disclosed by: Vossbeck et al., "Direct transfoming activity of TGF-beta on rat fibroblasts", Int. J. Cancer 61:92–97, 1995; Goruppi et al., "Dissection of c-myc domains involved in S phase induction of NIH3T3 fibroblasts", Oncogene 9:1537–44, 1994; Fernandez et al., "Differential sensitivity of normal and Ha-ras transformed C3H mouse embryo fibroblasts to tumor necrosis factor: induction of bc1-2, c-myc, and manganese superoxide dismutase in resistant cells", Oncogene 9:2009–17, 1994; Harrington et al., "c-Myc-induced apoptosis in fibroblasts is inhibited by specific cytokines", EMBO J. 13:3286–3295, 1994; Itoh et al., "A novel protein domain required for apoptosis. Mutational analysis of human Fas antigen", J. Biol. Chem. 268:10932–7, 1993.

Assays for apoptosis in neuronal cells are disclosed by: Melino et al., "Tissue transglutaminase and apoptosis: sense and antisense transfection studies with human neuroblastoma cells", Mol. Cell Biol. 14:6584–6596, 1994; Rosenbaum et al., "Evidence for hypoxia-induced, programmed cell death of cultured neurons", Ann. Neurol. 36:864–870, 1994; Sato et al., "Neuronal differentiation of PC12 cells as a result of prevention of cell death by bc1-2", J. Neurobiol 25:1227–1234, 1994; Ferrari et al., "N-acetylcysteine D- and L-stereoisomers prevents apoptotic death of neuronal cells", J. Neurosci. 1516:2857–2866, 1995; Talley et al., "Tumor necrosis factor alpha-induced apoptosis in human neuronal cells: protection by the antioxidant N-acetylcysteine and the genes bc1-2 and crma", Mol. Cell Biol. 1585:2359–2366, 1995; Talley et al., "Tumor Necrosis Factor Alpha-Induced Apoptosis in Human Neuronal Cells: Protection by the Antioxidant N-Acetylcysteine and the Genes bc1-2 and crma", Mol. Cell. Biol. 15:2359–2366, 1995; Walkinshaw et al., "Induction of apoptosis in catecholaminergic PC12 cells by L-DOPA. Implications for the treatment of Parkinson's disease.", J. Clin. Invest. 95:2458–2464, 1995.

Assays for apoptosis in insect cells are disclosed by: Clem et al., "Prevention of apoptosis by a baculovirus gene during infection of insect cells", Science 254:1388–90, 1991; Crook et al., "An apoptosis-inhibiting baculovirus gene with a zinc finger-like motif", J. Virol. 67:2168–74, 1993; Rabizadeh et al., "Expression of the baculovirus p35 gene inhibits mammalian neural cell death", J. Neurochem. 61:2318–21, 1993; Birnbaum et al., "An apoptosis inhibiting gene from a nuclear polyhedrosis virus encoding a polypeptide with Cys/His sequence motifs", J. Virol. 68:2521–8, 1994; Clem et al., *Mol. Cell. Biol.* 14:5212–5222, 1994.

XVIII. Construction of a Transgenic Animal

Characterization of NAIP genes provides information that is necessary for a NAIP knockout animal model to be developed by homologous recombination. Preferably, the model is a mammalian animal, most preferably a mouse. Similarly, an animal model of NAIP overproduction may be generated by integrating one or more NAIP sequences into the genome, according to standard transgenic techniques.

A replacement-type targeting vector, which would be used to create a knockout model, can be constructed using an isogenic genomic clone, for example, from a mouse strain such as 129/Sv (Stratagene Inc., LaJolla, Calif.). The targeting vector will be introduced into a suitably-derived line of embryonic stem (ES) cells by electroporation to generate ES cell lines that carry a profoundly truncated form of a NAIP. To generate chimeric founder mice, the targeted cell lines will be injected into a mouse blastula stage embryo. Heterozygous offspring will be interbred to homozygosity. Knockout mice would provide the means, in vivo, to screen for therapeutic compounds that modulate apoptosis via an NAIP-dependent pathway. Making such mice may require use of loxP sites due to the multiple copies of NAIP on the chromosome (see Sauer and Henderson, Nucleic Aids Res. 17: 147–61 (1989)).

EXAMPLES

The examples are meant to illustrate, not limit the invention.

Example 1

Expression of NAIP in Rat-1, CHO and HeLa Pooled Stable Lines and Adenovirus Infected Cells Analysed by Western Blotting and Immunofluorescence To generate nearly 3.7 kb NAIP construct tagged with the myc epitope (I) MTG-SP3.7, a 2.5 kb Bsu36I/SalI fragment of NAIP cloned into Bluescript and (ii) Bsu36I/XhoI cut MTG-SE1.7, the expression vector pcDNA3 containing a 300 bp myc epitope and a 1.7 kb fragment of NAIP were ligated. HeLa, CHO and Rat-1 cells were transfected by lipofection (Gibco BRL) with 8 μg DNA and G418 resistant transformants were selected by maintaining the cells in 250 μg/ml, 400 μg/ml and 800 μg/ml G418 respectively. All cells were maintained in Eagles medium containing 10% fetal calf serum. For construction of the adenovirus, a 3.7 kb BamHI fragment of NAIP was cloned into the SwaI site of the adenovirus expression cosmid pAdexi CAwt. Production of vectors, purification by double cesium chloride gradient and titer determination was as described in Rosenfeld, M. A. et. al. 1992, and Graham, F. L. and Van Der Eb, A. 1973.

Western blot analysis was performed using mouse anti-human myc monoclonal antibody (Ellison, M. J. and Hochstrasser, M. J. 1991) or rabbit anti-human NAIP (E 1.0) polyclonal antibody. For NAIP antibody production, rabbits were immunized with purified bacterial produced fusion protein in complete Freunds adjuvant. Serum was pre-cleared with GST protein and anti-NAIP immunoglobin purified with immobilized GST-NAIP fusion proteins.

For immunofluorescence, cells were grown on glass slides, fixed with formaldehyde for 10 minutes, incubated with anti-NAIP (1:200) or anti-myc (1:20) in PBS, 0.3% Triton X-100™ for 1 hour followed by incubation with secondary antisera, FITC-labelled donkey anti-rabbit immunoglobulin (Amersham), biotinylated goat anti-mouse immunoglobulin (Amersham) and streptavidin Texas-Red™ (Amersham).

Example 2

The Effect of NAIP on Cell Death Induced by Serum Deprivation, Menadione and TNF-α

For each assay cells were plated at 5×10⁴ ml in triplicate. CHO or Rat-1 cells were treated with menadione for 1.5 hours, washed 5 times in PBS and maintained in normal media. For serum deprivation assays, cells were washed 5 times in PBS and maintained in media with 0% fetal calf serum. HeLa cells were treated with 20 units/ml TNF-α in combination with 30 g/ml cyclohexamide for 17 hours. Apoptosis was assayed for each trigger by propidium iodide staining. Adenovirus infected cells were subjected to triggers 36 hours post infection. LacZ expression was confirmed histochemically by 5-bromo-4-chloro-3-indoyl-β-D-galactoside (X-gal) as described in Ellison, M. J. and Hochstrasser, M. J. 1991. Transcription of PIAN was determined by in situ hybridization using the DIG labelled sense oligonucleotide following the manufacturers protocol (Boehringer Mannheim). The human Bcl-2 clone pB4 (ATCC) was digested with EcoRI and ligated into the EcoRI site of pcDNA3.

For adenovirus assays an adenovirus encoding LacZ, antisense NAIP (NAIP) or vector alone with no insert were utilized as controls. Bcl-2 was utilized as a positive control and pcDNA alone as a negative control in cell line assays. Cell viability was determined by trypan blue exclusion. Date are presented as averages of three independently derived transfected pools or infections.

Example 3

Immunofluorescence Analysis of Human Spinal Cord Tissue

Human tissues were obtained at autopsy from a 2 month old infant that died of non-neurological causes and stored at −80° C. 14 μM cryostat sections were fixed in formaldehyde for 20 minutes, rinsed in PBS and incubated in blocking solution (2% horse serum, 2% casien, 2% BSA in PBS) for 15 minutes prior to overnight incubation with anti-NAIP antisera diluted in this blocking solution. CY-3 labelled donkey anti-rabbit immunoglobulin (Sigma) was utilized as secondary antisera.

Example 4

Isolating and Cloning the NAIP Gene

PAC Contig Array

The 40G1 CATT subloci demonstrated linkage disequilibrium and therefore a PAC contiguous array containing the CATT region was constructed. This PAC contig array comprised 9 clones and extended approximately 400 kb. Genetic analysis combined with the physical mapping data indicated that the 40G1 CATT subloci marker which showed the greatest disequilibrium with SMA was duplicated and was localized at the extreme centromeric of the critical SMA interval. Consequently the 154 kb PAC clone 125D9 which contained within 10 kb of its centromeric end the SMA interval defining CMS allele 9 and extended telemetrically to incorporate the 40G1 CATT sublocus was chosen for further examination.

Two genomic libraries were constructed by performing complete and partial (average insert size 5 kb) Sau3A1 on PAC 125D9 and cloning the restricted products into BamHI digested Bluescript plasmids. Genomic sequencing was conducted on both termini of 200 clones from the 5 kb insert partial Sau3A1 library in the manner of (Chen et al., 1993) permitting the construction of contiguous and overlapping genomic clones covering most of the PAC. This proved instrumental in the elucidation of the neuronal apoptosis inhibitor protein gene structure.

PAC 125D9 is cleaved into 30 kb centromeric and 125 kb telomeric fragments by a NotI site (which was later shown to bisect exon 7 of the PAC 125D9 at the beginning of the apoptosis inhibitor domain. The NotI PAC fragments were isolated by preparative PFGE and used separately to probe fetal brain cDNA libraries. Physical mapping and sequencing of the NotI site region was also undertaken to assay for the presence of a CpG island, an approach which rapidly detected coding sequences. The PAC 125D9 was also used as a template in an exon trapping system resulting in the identification of the exons contained in the neuronal apoptosis inhibitor protein gene.

The multipronged approach, in addition to the presence of transcripts identified previously by hybridization by clones from the cosmid array (such as, GA1 and L7), resulted in the rapid identification of six cDNA clones contained in neuronal apoptosis inhibitor protein gene. The clones were arranged, where possible, into overlapping arrays. Chimerism was excluded on a number of occasions by detection of co-linearity of the cDNA clone termini with sequences from clones derived from the PAC 125D9 partial Sau3A1 genomic library.

Cloning of Neuronal Apoptosis Inhibitor Protein Gene

A human fetal spinal cord cDNA library was probed with the entire genomic DNA insert of cosmid 250B6 containing one of the 5 CATT subloci. This resulted in a detection of a 2.2 kb transcript referred to as GA1. Further probings of fetal brain libraries with the contiguous cosmid inserts (cosmids 40G1) as well as single copy subclones isolated from such cosmids were undertaken. A number of transcripts were obtained including one termed L7. No coding region was detected for L7 probably due to the fact that a substantial portion of the clone contained unprocessed heteronuclear RNA. However, it was later discovered that L7 proved to comprise part of what is believed to be the neuronal apoptosis inhibitor protein gene. Similarly, the GA1 transcript ultimately proved to be exon 13 of the neuronal apoptosis inhibitor protein. Since GA1 was found to contain exons indicating that it was an expressed gene, it was of particular interest. The GA1 transcript which was contained within the PAC clone 125D9 was subsequently extended by further probing in cDNA libraries.

The remaining gaps in the cDNA were completed and the final 3' extension was achieved by probing a fetal brain library with two trapped exons. A physical map of the cDNA with overlapping clones was prepared. The entire cDNA sequence is shown in Table 1 and contains 18 exons (1 to 14a and 14 to 17). The amino acid sequence starts with methionine which corresponds to the nucleotide triplet ATG.

DNA Manipulation and Analysis

Four genomic libraries containing PAC 125D9 insert were constructed by BamHI, BamHI/NotI, total and partial Sau3aI (selected for 5 kb insert size) digestions of the PAC genomic DNA insert and subcloned into Bluescript vector. Sequencing of approximately 400 bp of both termini of 200 five kb clones from the partial Sau3AI digestion library in the manner of Chen et al. (1993) was undertaken.

Coding sequences from the PACs were isolated by the exon amplification procedure as described by Church et al. (1994). PACs were digested with BamHI or BamHI and BgIII and subcloned into pSPL3. Pooled clones of each PAC were transfected into COS-1 cells. After a 24 h transfection total RNA was extracted. Exons were cloned into pAMP 10 (Gibco, BRL) and sequenced utilizing primer SD2 (GTG AAC TGC ACT GTG ACA AGC TGC) SEQ ID NO:25.

DNA sequencing was conducted on an ABI 373A automated DNA sequencer. Two commercial human fetal brain cDNA libraries in lambda gt (Stratagene) and lambda ZAP (Clontech) were used for candidate transcript isolation. The Northern blot was commercially acquired (Clontech) and probing was performed using standard methodology.

In general, primers used in the paper for PCR were selected for $T_m$s of 60° C. and can be used with the following conditions: 30 cycles of 94° C., 60 s; 60° C., 60 s; 72° C., 90 s. PCR primer mappings are as referred to in the figure legends and text. Primer sequences are as follows:

Our genetic and mapping analysis of SMA has led to the identification of the 154 kb insert of PAC125D9 as the likely site of the SMA gene. We report here the complete DNA sequence of the 131 kb portion of the PAC 125D9 insert which contains both NAIP and SMN$^{tel}$ as well as the 3' end of a copy of the Basic Transcription Factor gene BTF2p44.[9] PAC 125D9 insert digested with a variety of restriction enzymes was used to generate nine libraries. Shotgun sequencing of clones from the Sau3A1 library was hampered by the Alu rich nature of the area, sequencing was therefore conducted by a modified transposon based approach[10] yielding the configuration depicted in the figure. The NAIP and SMN$^{tel}$ genes, separated by 15.5 kb, are in a tail to tail (5'-->3':3'<--5') orientation, spanning 56 kb and 28 kb of genomic DNA, respectively. The gene BTF2p44 exists in a number of copies on 5q13.1[10]; exons 11–16 of one BTF2P44 copy occupy the most 5' eleven kb of the PAC insert followed by an 11 kb interval before NAIP exon 2. The first NAIP exon as originally reported[3] is not present in this PAC and may have been a heteronuclear artifact. An approximately 3 kb section of the 15.5 kb interval between NAIP and SMN (CCA, figure) is transcribed but contains no protein coding sequence. Indeed, no coding sequence in addition to BTF2P44, NAIP and SMN was identified throughout the entire interval.

CpG islands were identified in the 5' region of both SMN and NAIP genes. One hundred and forty five Alu sequences were identified in the 131 kb sequence, with five clusters of high density seen (figure legend). Such Alu density associated with L1 paucity (five copies) is in keeping with previous findings for light Giemsa staining (or reverse) chromosomal bands[11]. Copies of other repeats (e.g. MIR2, MST and MER) as detected by Sequin program are also as depicted[12]. The polymorphic microsatellite loci previously mapped to the SMA region; (CMS1[13], CATT[14] or C161[15], C171[15], C272[15] or AG-1[16,17]) as well as unusual single and di-nucleotide repeats are as shown.

```
1258 ATg CTT ggA TCT CTA gAA Tgg - Sequence ID No.3

1285 AgC AAA gAC ATg Tgg Cgg AA - Sequence ID No.4

1343 CCA gCT CCT AgA gAA AgA Agg A - Sequence ID No.5

1844 gAA CTA Cgg CTg gAC TCT TTT - Sequence ID No.6

1863 CTC TCA gCC TgC TCT TCA gAT - Sequence ID No.7

1864 AAA gCC TCT gAC gAg Agg ATC - Sequence ID No.8

1884 CgA CTg CCT gTT CAT CTA CgA - Sequence ID No.9

1886 TTT gTT CTC CAg CCA CAT ACT - Sequence ID No.10

1887 CAT TTg gCA TgT TCC TTC CAA g - Sequence ID No.11

1893 gTA gAT gAA TAC TgA TgT TTC ATA ATT - Sequence ID No.12

1910 TgC CAC TgC CAg gCA ATC TAA - Sequence ID No.13

1919 TAA ACA ggA CAC ggT ACA gTg - Sequence ID No.14

1923 CAT gTT TTA AgT CTC ggT gCT CTg - Sequence ID No.15

1926 TTA gCC AgA TgT gTT ggC ACA Tg - Sequence ID No.16

1927 gAT TCT ATg TgA TAg gCA gCC A - Sequence ID No.17

1933 gCC ACT gCT CCC gAT ggA TTA - Sequence ID No.18

1974 gCT CTC AgC TgC TCA TTC AgA T - Sequence ID No.19

1979 ACA AAg TTC ACC ACg gCT CTg - Sequence ID No.20
```

The full length NAIP cDNA (6228 bp with an ORF of 4212 bp) was also elucidated by cDNA sequencing and comparison with PAC sequence, comprising 17 exons encoding a predicted 156 kDa protein of 1403 amino acids (data not shown). A novel NAIP exon 14 between the original exon 14 and 15 was identified. The original exon 17 has been replaced by a novel exon which contains the stop codon, a 1.6 kb 3' UTR region and the polyadenylation consensus site (AATAAA) identified by 3' RACE. No new protein domains are found in the NAIP gene.

A rigorous definition of how far deletions extend on type 1 SMA chromosomes is central to our understanding of disease pathogenesis. If the genotype most frequently observed on type 1 SMA chromosomes (i.e. absence of NAIP exons 4 and 5 as well as $SMN^{tel}$ exons 7 and 8) are the result of a single event, then our sequencing suggests a minimal deletion size of 60 kb. The high deletion frequency on type 1 SMA chromosomes of the CATT-40G1[14], (which maps between NAIP exon 7 and 8) is consistent with such a deletion.

Southern blots containing genomic DNA probed with NAIP cDNA reveal a diversity of bands, a result of the polymorphic number of variant forms of this locus mapping to 5q13.1[3,18]. In contrast, the same blots probed with SMN cDNA reveals only the bands associated with the intact SMN locus, for SMA and non-SMA individuals alike. Thus, there is no evidence of truncated or partially deleted SMN genes such as seen with the NAIP gene. The absence of any detectable SMN junction fragment in SMA patients strongly suggests that the $SMN^{tel}$ exon 7 and 8 deletion detected in the significant majority of SMA cases incorporates the entire $SMN^{tel}$ gene, thus extending the putative minimal SMA type 1 deletion to approximately 100 kb (figure). This is in keeping with the high deletion frequency of C272[15] (or AG-1[16,17]) microsatellite (which maps to SMN exon 1, figure) on type 1 SMA chromosomes. A 15% deletion frequency of one copy of BTF2P44 is observed in all SMA cases irrespective of clinical severity[9], suggesting that this mutation may not be an extension of the putative SMN-NAIP deletion. Clarification of this issue must await details of which copy of p44 is deleted.

Our sequencing of PAC125D9 maps the intact NAIP locus and clinically relevant $SMN^{tel}$ to a 100 kb region which contains those microsatellite polymorphisms that are preferentially deleted on the significant majority of type 1 SMA chromosomes (i.e. CATT-40G1[14] C272[15] or AG-1[16,17]) The absence of any protein coding sequence, other than NAIP and SMN in this interval, focuses attention on these two genes as the key modulators of type 1 SMA. One potential pathogenic model is that $SMN^{tel}$ absence acts as the primary neurotoxic insult[19] with NAIP depletion/absence leading to an attenuated apoptotic resistance[5,6], exacerbating motor neuron attrition. Presence of additional $SMN^{cen}$ may also act to modulate the course of the disease[20]. In addition to aiding in our comprehension of the molecular pathology of acute SMA, the sequence presented here should help in the study of transcriptional control elements for both genes, possibly facilitating the formulation of genetic therapies for this devastating neuromuscular disease.

DNA Sequencing

Partial Sau3A1 (selected for 3–5 kb) BamHI, EcoRI, HindIII, PstI, SstI, XbaI and EcoRV libraries) were made from the PAC125D9 insert and sequenced using a transposon-based methodology (TN1000 Gold Biotechnology[10]). Subcloning of a large number of inserts into the commercially supplied pMOB plasmid was found to be problematic, therefore pUC 18 and pBluescript SK were used. In general, fewer than 10% of clones had transposons in the vector region. *E. coli* lysate was employed as sequencing template using our modified heat soaked protocol[21]. Sequencing was from the TN1000 transposon randomly inserted into the target DNA, using primers of opposite orientation (5'-ATA TAA ACA ACGAAT TAT CTC C-3'; 5'-GTA TTA TAA TCA ATA AGTTAT ACC-3'), generating approximately 1 kb of sequence with a 5 bp overlap, easily spanning 300 bp Alu repeats. Our approach permitted sequencing of inserts as large as 14 kb.

As the SMA region is known to be unstable, special care to ensure an intact, unaltered PAC insert was undertaken primarily by comparison of PAC125D9 insert and genomic DNA hybridization patterns on Southern blots.

Raw DNA sequence data generated by our automated sequencers (ABI 373 and ABI 373A) were processed and assembled in parallel by the Sequencher 3.0 program (Gene Codes Inc.); and the GAP4 program from the Staden package[27]. The edited results were automatically converted into GCG file formats[22] and placed in a separate database for searches by outside users using our e-mail server at smafasta@mgcheo.med.uottawa.ca. GRAIL[28] and Blast[29] searches were employed to screen for protein coding sequence and the PROSITE Protein database[24] was used to search for protein domains.

Example 5

NAIP Expression Vectors

Using the identified NAIP sequence information, a full length 3.7 kb NAIP construct tagged with the myc epitope (1) MTG-SP3.7, a 2.5 kb Bsu36I/SalI fragment of NAIP cloned into Bluescript and (ii) Bsu36I/XhoI cut MTG-SE1.7, the expression vector pcDNA3 containing a 300 bp myc epitope and a 1.7 kb fragment of NAIP were ligated. HeLa, CHO and Rat-1 cells were transfected by lipofection (Gibco BRL) with 8 µg DNA and G418 resistant transformants were selected by maintaining the cells in 250 µg/ml, 400 µg/ml and 800 µg/ml G418 respectively.

Figure 1B:
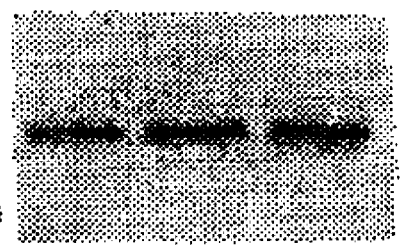
Figure 1C:
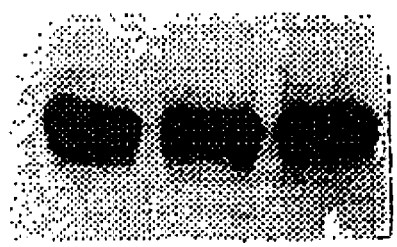
Figure 1D:
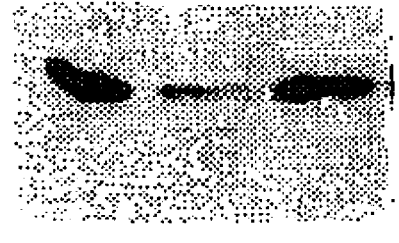
Figure 1E:
Figure 1F:
Figure 2A:
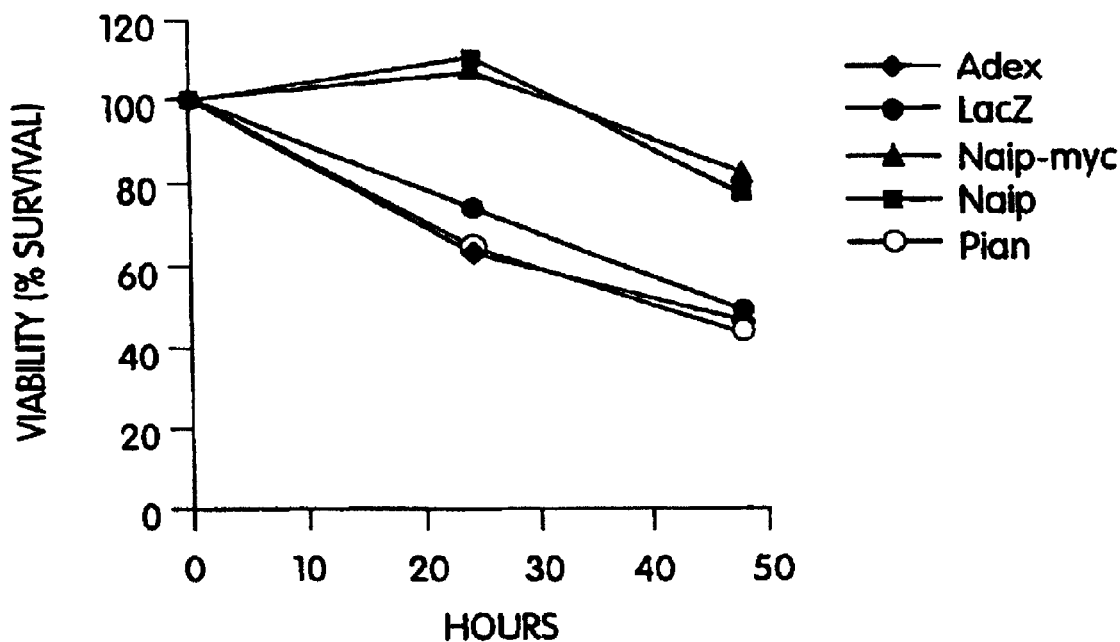
FIG. 2. shows the effect of NAIP on cell death induced by serum deprivation, menadione and TNF-α. Viability of a CHO cells deprived of serum in A, adenovirus infected cells and B, pooled transformants. C–H, cell death induced by menadione in adenvirus infected CHO (C, D) and Rat-1 (E, F and G, H) adenovirus infected cells and pooled transformants respectively. I, adenovirus infected and J, pooled transformants of TNF-α/cyclohexamide treated HeLa cells.
Figure 2B:
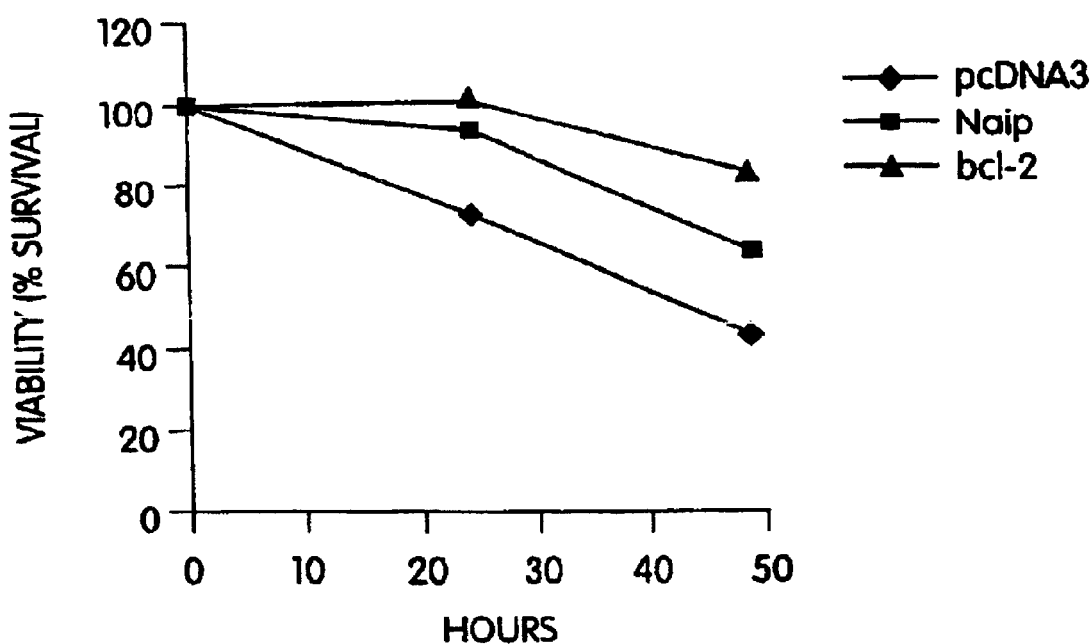
Figure 2C:
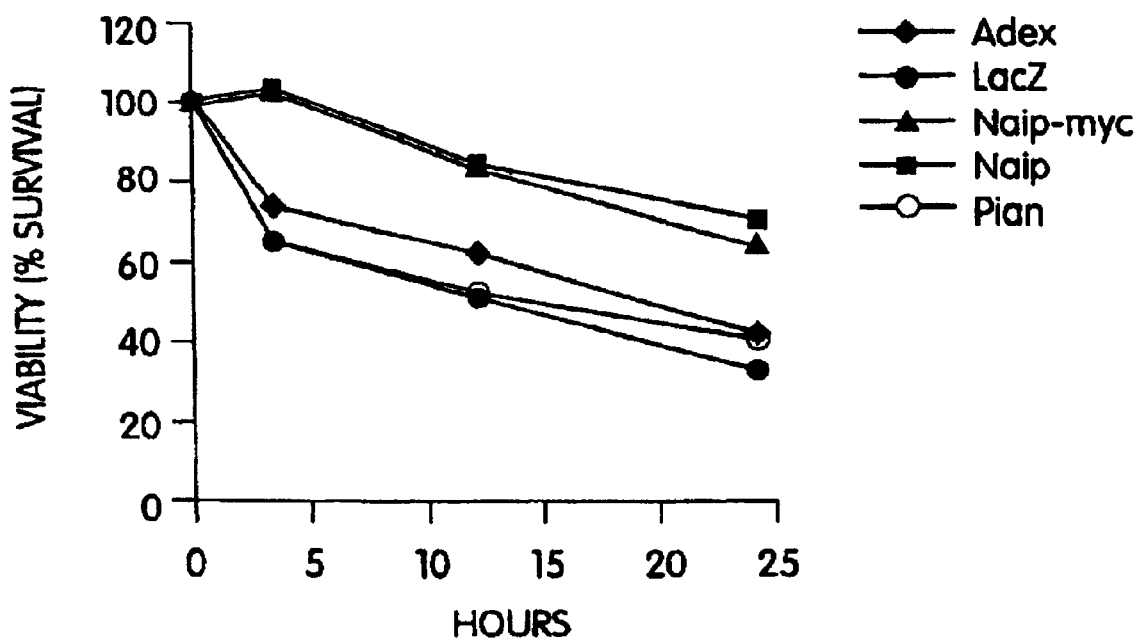
Figure 2D:
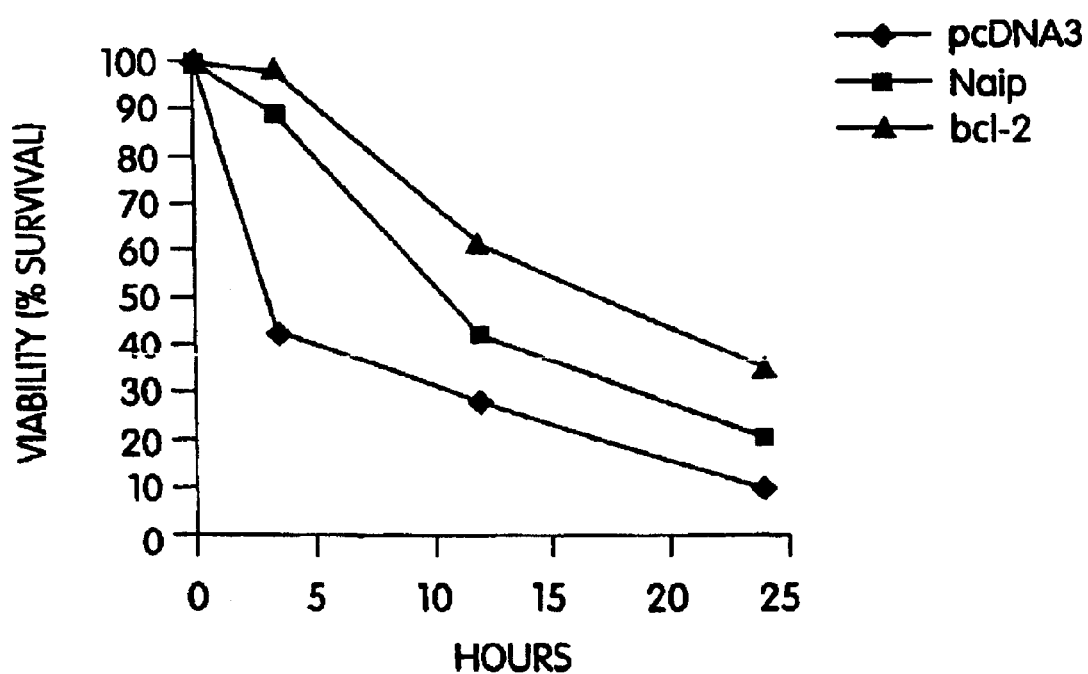
Figure 2E:
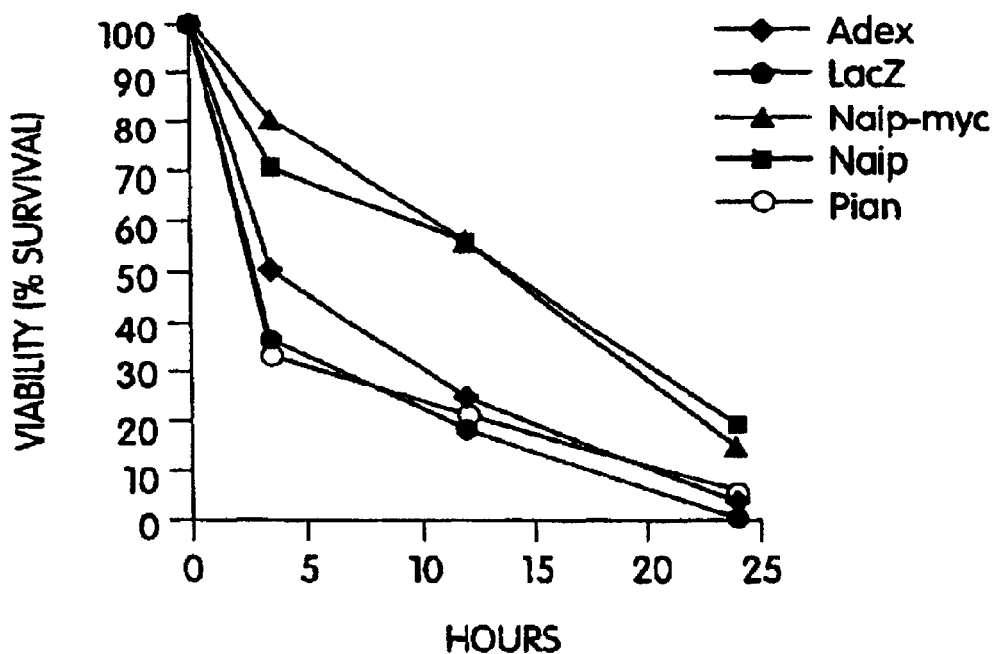
Figure 2F:
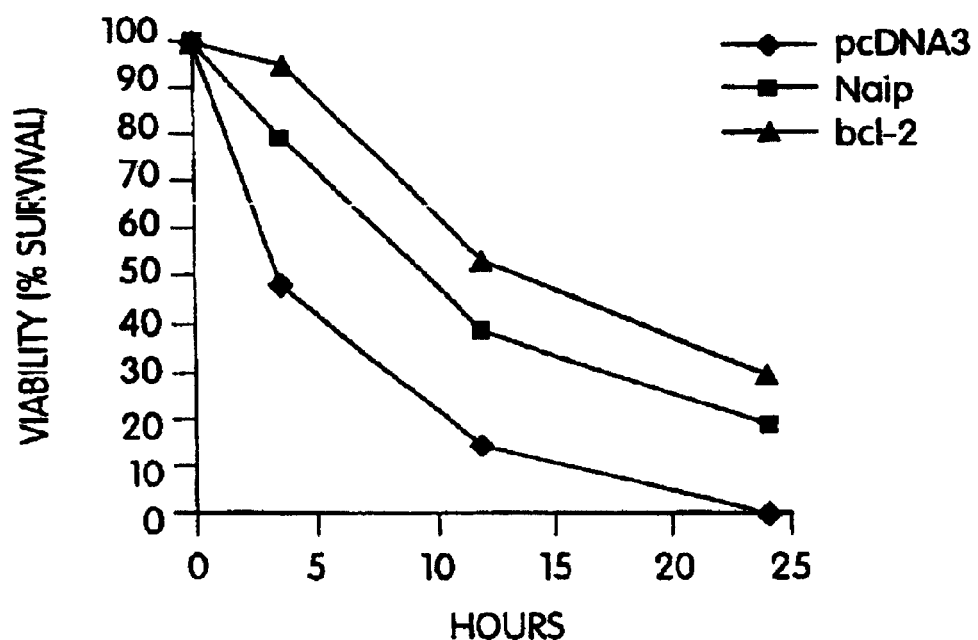
Figure 2G:
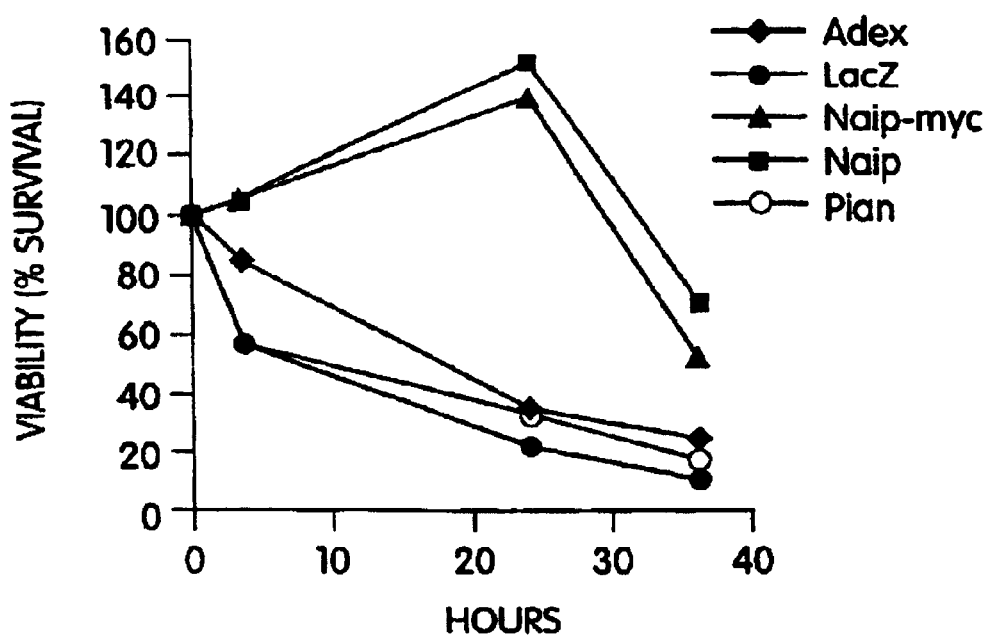
Figure 2H:
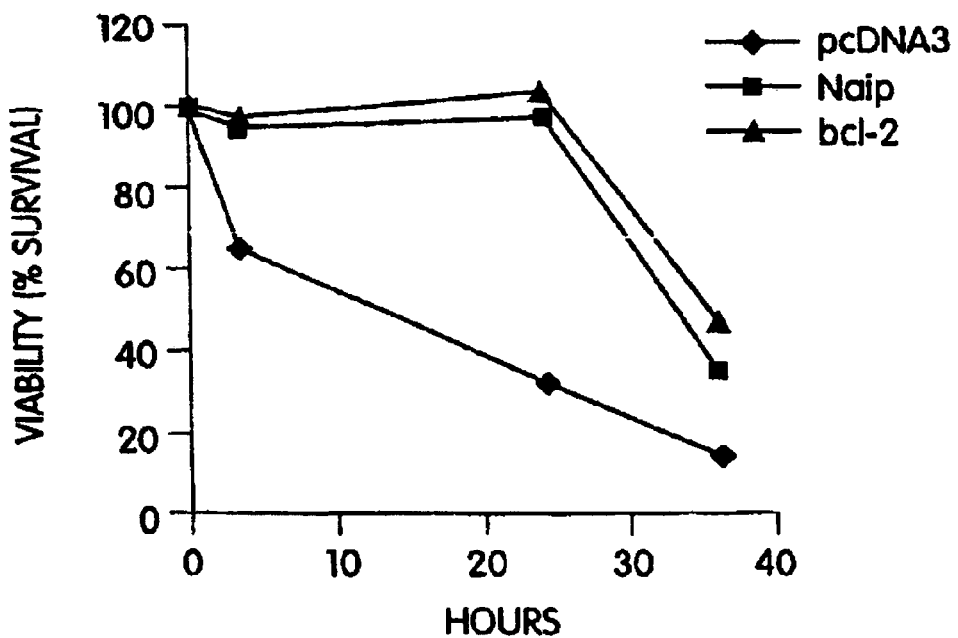
Figure 2I:
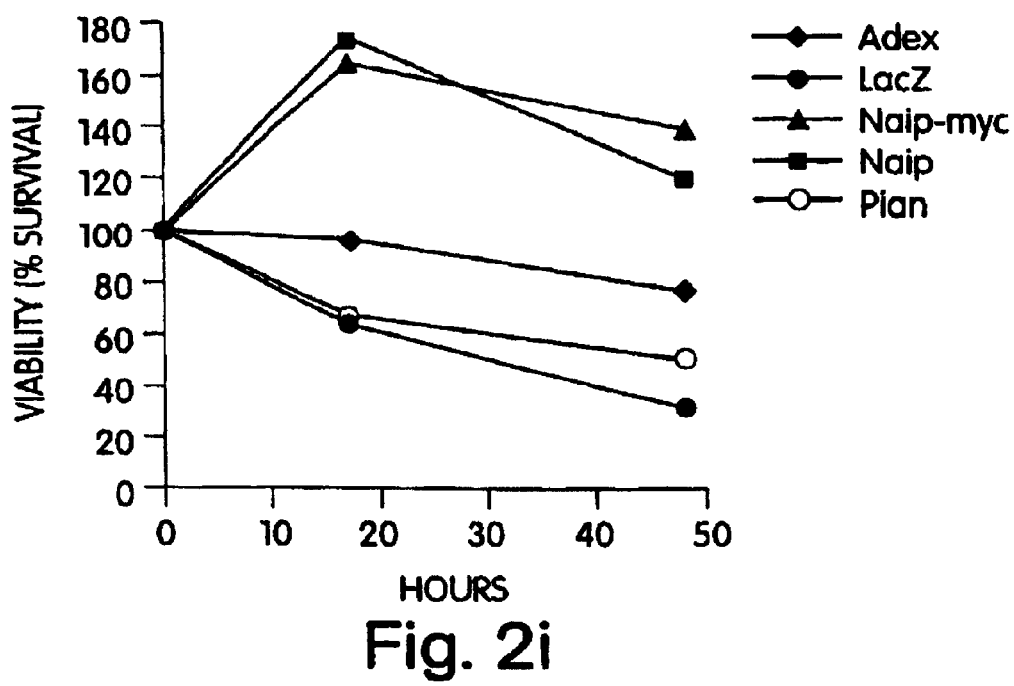
Figure 2J:
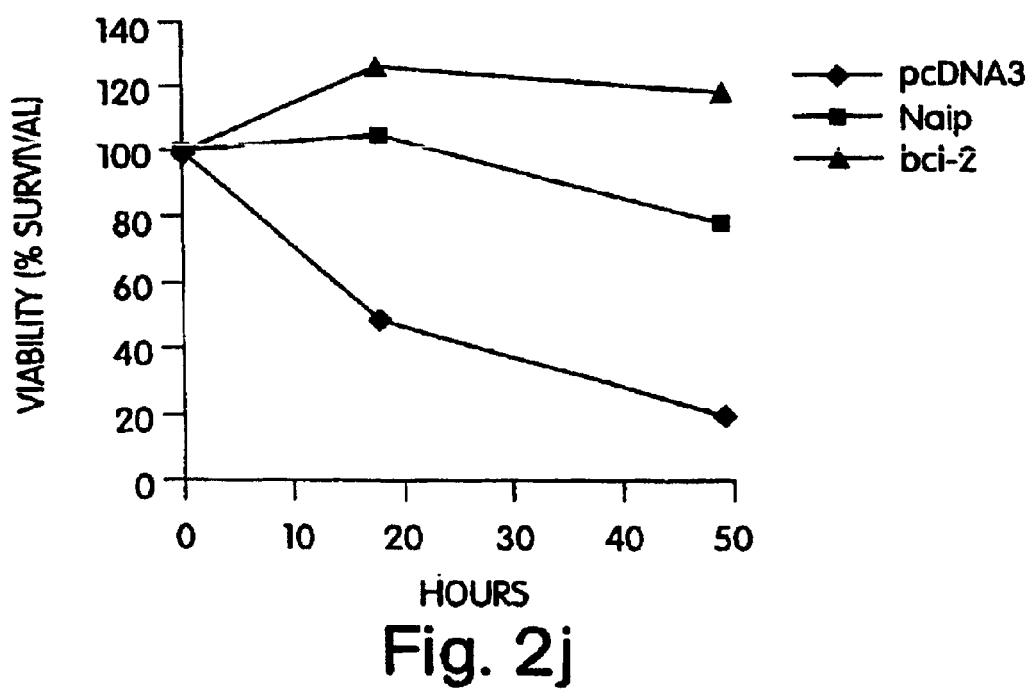

In a second approach, cells were infected with adenovirus alone or adenovirus expressing either NAIP, antisense NAIP, or LacZ. For construction of the adenovirus, a 3.7 kb BamHI fragment of NAIP was cloned into the SwaI site of the adenovirus expression cosmid pAdex1CAwt. The antisense NAIP RNA contains a sequence complementary to the region of an mRNA containing an initiator codon. Expression of NAIP was confirmed in both procedures by Western blot analysis and immunofluorescence. Following infection with the recombinant adenoviruses, CHO cells were induced to undergo apoptosis by serum deprivation with survival rates of 48% (no insert), 51% (LacZ) and 45% (antisense NAIP) at 48 hours (FIG. 1*a*). In contrast, CHO cells infected with adenovirus expressing NAIP demonstrate 78–83% survival. NAIP also induced survival in stably transfected CHO pools, albeit slightly less than that seen in adenovirus infected cells: 44% of the vector transfectants and 65% of the NAIP transfectants survived at 48 hours (FIG. 1*b*). Next, overexpression of NAIP in CHO cells treated with 20 µM menadione (a potent inducer of free radicals) resulted in 20–30% enhancement of survival compared with controls after 24 hours (FIGS. 1*c*, 1*d*). Overexpression of NAIP also protected menadione treated Rat-1 fibroblasts from undergoing cell death (FIGS. 1*e*, 1*f*, 1*g*, 1*h*). Only 15% of cells infected with LacZ expressing adenovirus were viable at 12 hours in contrast to 80% of NAIP infected cells, an effect also detected with the pooled Rat-1 NAIP transfectants.

Even greater survival was induced by NAIP overexpression at a lower menadione concentration (5 µM), with 98% of pooled NAIP transfectants and 33% of control transfectants viable at 24 hours (FIGS. 1g, 1h). Also assessed was the protective effect of NAIP on cells exposed to the cytokine TNF-α. HeLa cells treated with TNF-α and cyclohexamide were protected from apoptosis when infected with adenovirus expressing high levels of NAIP (139%) at 48 hours, an effect not observed with antisense NAIP (52%) (FIGS. 1i, 1j). A similar effect was observed in pooled HeLa transformants.

To confirm that cells surviving the apoptotic agents expressed NAIP, immunofluorescence with anti-NAIP antisera was performed on a number of the cell death assays. Immunofluorescence is a technique which localizes proteins within a cell by light microscopy by the use of antibodies specific for a desired protein and a fluorescence microscope. Dyes can be chemically coupled to antibodies directed against purified antibodies specific for a desired protein. This flourescent dye-antibody complex when added to permeabilized cells or tissue sections binds to the desired antigen-antibody which lights up when illuminated by the exciting wavelength. Fluorescent antibodies may also be microinjected into cultured cells for visualization. Using immunofluorescence, CY-3, a dye which emits red light, was coupled to a secondary antibody used to detect the bount anti-NAIP antibodies. A dramatic enrichment of NAIP expressing cells was observed, with no alteration noted in the cytoplasmic distribution of NAIP. These data offer strong support for the apoptotic suppression activity of NAIP.

Example 6

Cellular Distribution of NAIP using NAIP Antibodies

It was previously demonstrated (Roy, N. et. al. The gene for NAIP, a novel protein with homology to baculoviral inhibitor of apoptosis, is partially deleted in individuals with spinal muscle atrophy. *Cell* 80: 167–178 (1995).) by reverse transcriptase PCR analysis that the NAIP transcript is present in human spinal cord. To define more precisely the cellular distribution of NAIP, a polyclonal antiserum was raised against NAIP. The NAIP antibodies were then used in both immunocytochemistry and immunofluorescence techniques to visualize the protein directly in cells and tissues in order to establish the subcellular location and tissue specificity of the protein.

Figure 3A:
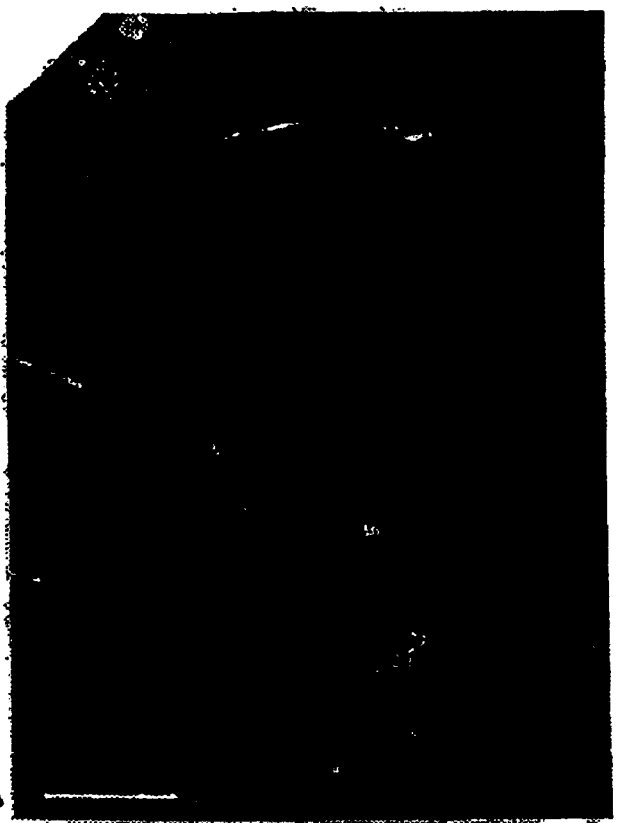
FIG. 3. shows immunofluorescence analysis of human spinal cord tissue. A, Anterior horn cells. B, Intermediolateral neurons. C, Dorsal roots. D, Ventral roots.
Figure 3B:
Figure 3C:
Figure 3D:
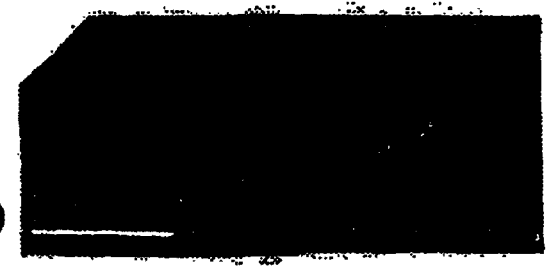
Figure 4:
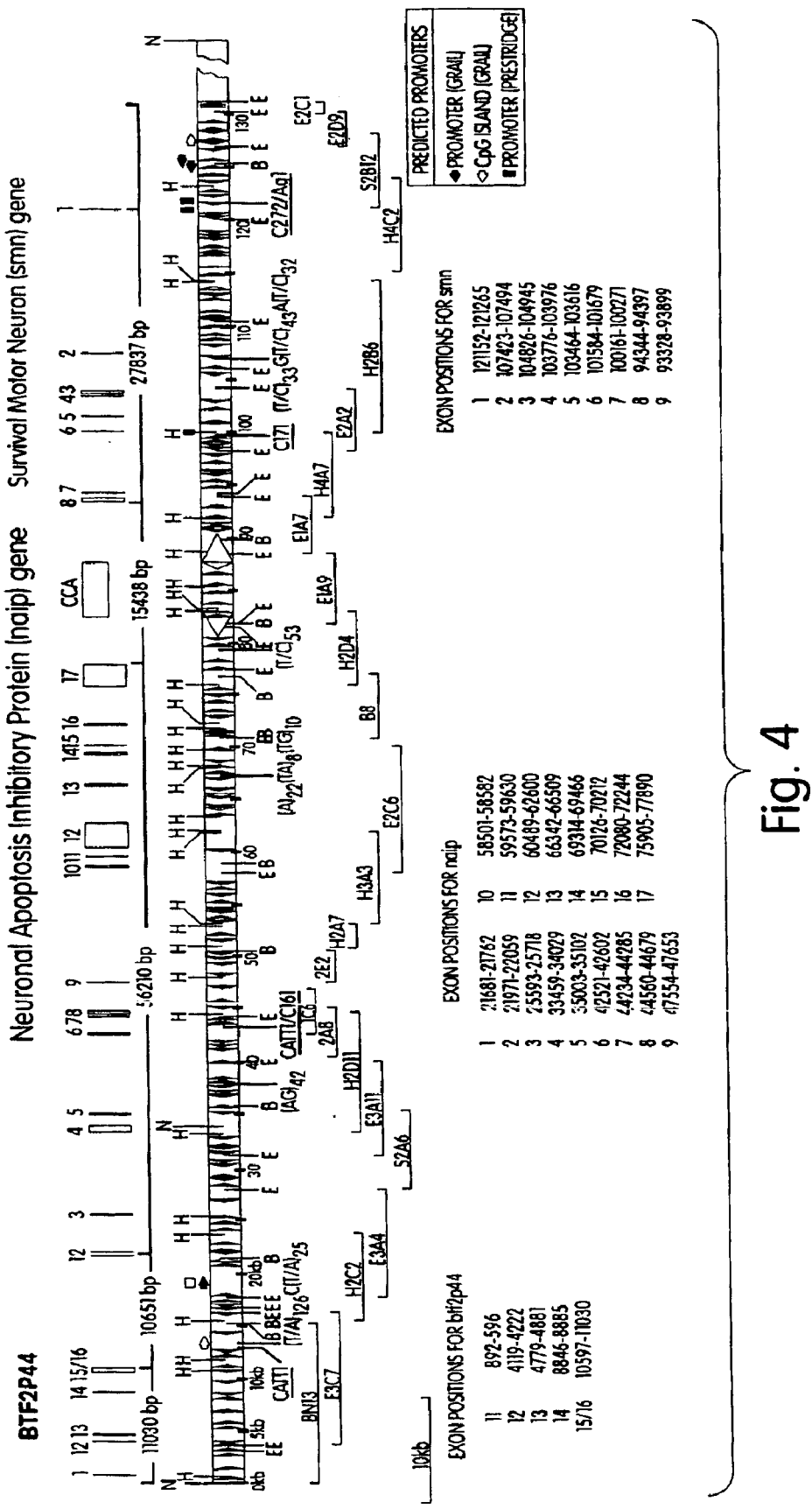
FIG. 4, depicts the genomic structure of PAC 125D9 from human chromosome 5q 13.1. Both strands of the 131,708 bp region shown in the figure have been sequenced and can be found as GenBank accession #U80017. NotI (N), EcoRI (E), HindIII (H) and BamHI (B) sites are indicated. The exons of BTF2p44, NAIP and SMN are bracketed. The transcribed (but not translated) CCA sequence is indicated by the box. The number of nucleotides which a specific region spans is as indicated, eg. the gap between NAIP and SMN is 15471 bp. The minimal tiling pattern of plasmid clones covering the PAC is shown below. The letters at the beginning of each clone indicate the restriction enzymes used for preparing the plasmid libraries, except for 1C6, 2A8 and 2E2 which are clones from the partial Sau3AI libraries. (SstI-S). The location and orientation of eight classes of repeat sequences found using the NIH Sequin program are depicted by triangles. Promotor sequences as detected by GRAIL (filled arrows) or Prestridge (Prestidge, D. S. *J. Mol. Biol.* 249, 923–932 (1995) (filled block) programs and CpG islands (unifilled arrow) are shown as arrows or blocks above the bar.

The ability of the polyclonal antibody to detect NAIP was confirmed by immunofluorescence of cells transfected with myc tagged NAIP employed both the anti-NAIP and anti-Myc antibodies, as well as western blot analysis on protein extracts of these cells (FIG. 1). In the western blotting technique, proteins are run on polyacrylamide gel and then transferred onto nitrocellulose membranes. These membranes are then incubated in the presence of the antibody (primary), then following washing are incubated to a secondary antibody which is used for detection of the protein-primary antibody complex. Following repeated washing, the entire complex is visualized using colorimetric or chemiluminescent methods. A protein of the expected molecular weight was detected by both antibodies in western blots and their cellular co-localization demonstrated by immunofluorescence. Sections of human spinal cord stained with anti-NAIP showed strong immunoreactivity in the cytoplasm of the anterior horn cells and intermediolateral neurons (FIGS. 3a and 3b). Consistent with the motor neuron staining, NAIP reactivity was observed in the ventral roots which contain motor axons but not the dorsal roots comprised of sensory axons (FIGS. 3c and 3d). The observation of motor neuron staining correlates well with a role for the protein in the pathogenesis of SMA. However, the presence of NAIP in intermediolateral neurons which are not reported to be affected in SMA, implies heterogeneity in the apoptotic pathways between the two classes of neurons.

Other Embodiments

Figure 7C:
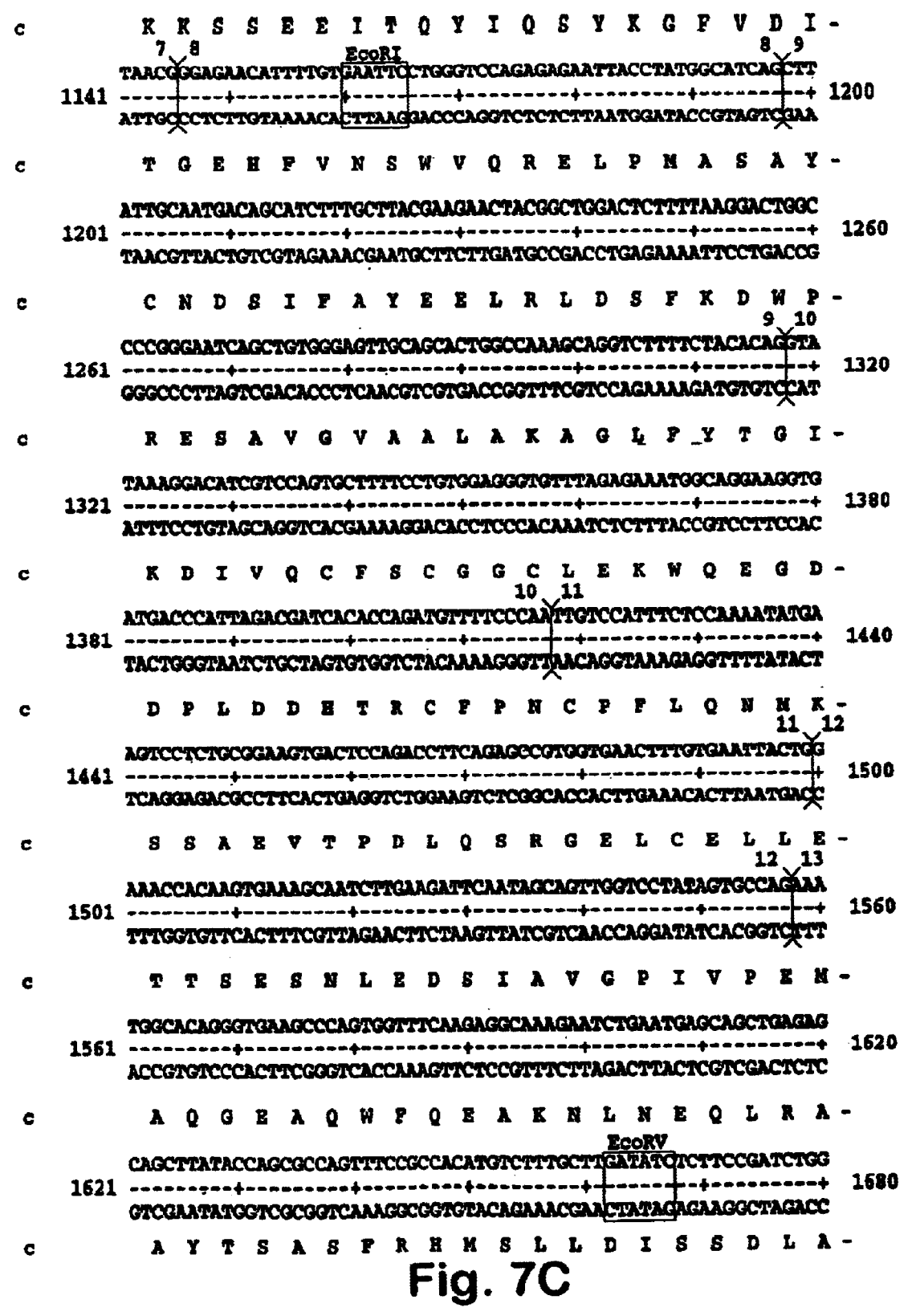

In other embodiments, the invention includes any protein which is substantially identical to a mammalian NAIP polypeptides provided in FIGS. 6 and 7, Seq. ID NOS: 22 and 24); such homologs include other substantially pure naturally-occurring mammalian NAIP proteins as well as allelic variants; natural mutants; induced mutants; DNA sequences which encode proteins and also hybridize to the NAIP DNA sequences of FIGS. 6 and 7, (Seq. ID NOS: 21 and 23) under high stringency conditions or, less preferably, under low stringency conditions (e.g., washing at 2×SSC at 400 C with a probe length of at least 40 nucleotides); and proteins specifically bound by antisera directed to a NAIP polypeptide. The term also includes chimeric polypeptides that include a NAIP portion. The sequence of Seq. ID No. 1 and the IAP proteins are specifically excluded.

The invention further includes analogs of any naturally-occurring NAIP polypeptide. Analogs can differ from the naturally-occurring NAIP protein by amino acid sequence differences, by post-translational modifications, or by both. Analogs of the invention will generally exhibit at least 85%, more preferably 90%, and most preferably 95% or even 99% identity with all or part of a naturally occurring NAIP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring NAIP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or nonnaturally occurring or synthetic amino acids, e.g., B or y amino acids. In addition to full-length polypeptides, the invention also includes NAIP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of NAIP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a NAIP nucleic acid or amino acid sequence in a sample to be diagnosed. Particularly useful NAIP fragments for this purpose include, without limitation, the amino acid fragments shown in Table 2.

What is claimed is:

1. A substantially pure recombinant nucleic acid encoding the amino acid sequence of SEQ ID NO: 22.

2. The nucleic acid of claim 1, wherein said nucleic acid is operably linked to a regulatory sequence for expression of said polypeptide and wherein said regulatore sequence comprises a promoter.

3. The nucleic acid of claim 2, wherein said promoter is a constitutive promoter, is inducible by one or more external agents, or is cell-type specific.

4. A vector comprising the nucleic acid of claim 1, said vector being capable of directing expression of the polypeptide encoded by said nucleic acid in a vector-containing cell.

5. A substantially pure recombinant isolated nucleic acid encoding a NAIP polypeptide that inhibits apoptosis, wherein said nucleic acid is nucleotide 292 to nucleotide 4503 of SEQ ID NO: 21.

6. The nucleic acid of claim 5, wherein said nucleic acid is operably linked to a regulatory sequence for expression of said polypeptide and wherein said regulatory sequence comprises a promoter.

7. The nucleic acid of claim 6, wherein said promoter is a constitutive promoter, is inducible by one or more external agents, or is cell-type specific.

8. A vector comprising the nucleic acid of claim 5, said vector being capable of directing expression of the polypeptide encoded by said nucleic acid in a vector-containing cell.

* * * * *

UNITED STATES PATENT AND TRADEMARK OFFICE
CERTIFICATE OF CORRECTION

PATENT NO. : 6,994,957 B2 Page 1 of 1
APPLICATION NO. : 08/913322
DATED : February 7, 2006
INVENTOR(S) : Robert G. Korneluk et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 39 days.

Delete the phrase "by 39 days" and insert -- by 159 days --

Signed and Sealed this

Twenty-sixth Day of February, 2008

JON W. DUDAS
*Director of the United States Patent and Trademark Office*

SEQUENCE LISTING

<160> NUMBER OF SEQ ID NOS: 27

<210> SEQ ID NO 1
<211> LENGTH: 5504
<212> TYPE: DNA
<213> ORGANISM: Homo sapiens

<400> SEQUENCE: 1

| | | | | | |
|---|---|---|---|---|---|
| ttccggctgg | acgttgccct | gtgtacctct | tcgactgcct | gttcatctac | gacgaacccc | 60 |
| gggtattgac | cccagacaac | aatgccactt | catattgcat | gaagacaaaa | ggtcctgtgc | 120 |
| tcacctggga | cccttctgga | cgttgccctg | tgttcctctt | cgcctgcctg | ttcatctacg | 180 |
| acgaaccccg | ggtattgacc | ccagacaaca | atgccacttc | atattgggga | cttcgtctgg | 240 |
| gattccaagg | tgcattcatt | gcaaagttcc | ttaaatattt | tctcactgct | tcctactaaa | 300 |
| ggacggacag | agcatttgtt | cttcagccac | atactttcct | tccactggcc | agcattctcc | 360 |
| tctattagac | tagaactgtg | gataaacctc | agaaaatggc | cacccagcag | aaagcctctg | 420 |
| acgagaggat | ctcccagttt | gatcacaatt | tgctgccaga | gctgtctgct | cttctgggcc | 480 |
| tagatgcagt | tcagttggca | aggaactaga | agaagagga | gcagaaggag | cgagcaaaaa | 540 |
| tgcagaaagg | ctacaactct | caaatgcgca | gtgaagcaaa | aaggttaaag | acttttgtga | 600 |
| cttatgagcc | gtacagctca | tggataccac | aggagatggc | ggccgctggg | ttttacttca | 660 |
| ctggggtaaa | atctgggatt | cagtgcttct | gctgtagcct | aatcctcttt | ggtgccggcc | 720 |
| tcacgagact | ccccatagaa | gaccacaaga | ggtttcatcc | agattgtggg | ttccttttga | 780 |
| acaaggatgt | tggtaacatt | gccaagtacg | acataagggt | gaagaatctg | aagagcaggc | 840 |
| tgagaggagg | taaaatgagg | taccaagaag | aggaggctag | acttgcatcc | ttcaggaact | 900 |
| ggccatttta | tgtccaaggg | atatcccctt | gtgtgctctc | agaggctggc | tttgtcttta | 960 |
| caggtaaaca | ggacacggta | cagtgttttt | cctgtggtgg | atgtttagga | aattgggaag | 1020 |
| aaggagatga | tccttggaag | gaacatgcca | aatggttccc | caaatgtgaa | tttcttcgga | 1080 |
| gtaagaaatc | ctcagaggaa | attacccagt | atattcaaag | ctacaaggga | tttgttgaca | 1140 |
| taacgggaga | acattttgtg | aattcctggg | tccagagaga | attacctatg | gcatcagctt | 1200 |
| attgcaatga | cagcatcttt | gcttacgaag | aactacggct | ggactctttt | aaggactggc | 1260 |
| cccgggaatc | agctgtggga | gttgcagcac | tggccaaagc | aggtctttc | tacacaggta | 1320 |
| taaaggacat | cgtccagtgc | ttttcctgtg | gagggtgttt | agagaaatgg | caggaaggtg | 1380 |
| atgacccatt | agacgatcac | accagatgtt | tcccaattg | tccattctc | caaaatatga | 1440 |
| agtcctctgc | ggaagtgact | ccagaccttc | agagccgtgg | tgaactttgt | gaattactgg | 1500 |
| aaaccacaag | tgaaagcaat | cttgaagatt | caatagcagt | tggtcctata | gtgccagaaa | 1560 |
| tggcacaggg | tgaagcccag | tggtttcaag | aggcaaagaa | tctgaatgag | cagctgagag | 1620 |
| cagcttatac | cagcgccagt | tccgccaca | tgtctttgct | tgatatctct | tccgatctgg | 1680 |
| ccacggacca | cttgctgggc | tgtgatctgt | ctattgcttc | aaaacacatc | agcaaacctg | 1740 |
| tgcaagaacc | tctggtgctg | cctgaggtct | ttggcaactt | gaactctgtc | atgtgtgtgg | 1800 |
| agggtgaagc | tggaagtgga | aagacggtcc | tcctgaagaa | aatagctttt | ctgtgggcat | 1860 |
| ctggatgctg | tcccctgtta | aacaggttcc | agctggtttt | ctacctctcc | cttagttcca | 1920 |
| ccagaccaga | cgagggggctg | gccagtatca | tctgtgacca | gctcctagag | aaagaaggat | 1980 |
| ctgttactga | aatgtgcatg | aggaacatta | tccagcagtt | aaagaatcag | gtcttattcc | 2040 |

-continued

```
ttttagatga ctacaaagaa atatgttcaa tccctcaagt cataggaaaa ctgattcaaa    2100
aaaaccactt atcccggacc tgcctattga ttgctgtccg tacaaacagg ccagggaca     2160
tccgccgata cctagagacc attctagaga tccaagcatt tccctttat aatactgtct     2220
gtatattacg gaagctcttt tcacataata tgactcgtct gcgaaagttt atggtttact    2280
ttggaaagaa ccaaagtttg cagaagatac agaaaactcc tctctttgtg gcggcgatct    2340
gtgctcattg gtttcagtat ccttttgacc catcctttga tgatgtggct gttttcaagt    2400
cctatatgga acgcctttcc ttaaggaaca aagcgacagc tgaaattctc aaagcaactg    2460
tgtcctcctg tggtgagctg gccttgaaag gttttttttc atgttgcttt gagtttaatg    2520
atgatgatct cgcagaagca ggggttgatg aagatgaaga tctaaccatg tgcttgatga    2580
gcaaatttac agcccagaga ctaagaccat tctaccggtt tttaagtcct gccttccaag    2640
aatttcttgc ggggatgagg ctgattgaac tcctggattc agataggcag gaacatcaag    2700
atttgggact gtatcatttg aaacaaatca actcacccat gatgactgta agcgcctaca    2760
acaattttt gaactatgtc tccagcctcc cttcaacaaa gcagggccc aaaattgtgt      2820
ctcatttgct ccatttagtg gataacaaag agtcattgga gaatatatct gaaaatgatg    2880
actacttaaa gcaccagcca gaaatttcac tgcagatgca gttacttagg ggattgtggc    2940
aaatttgtcc acaagcttac ttttcaatgg tttcagaaca tttactggtt cttgccctga    3000
aaactgctta tcaaagcaac actgttgctg cgtgttctcc atttgttttg caattccttc    3060
aagggagaac actgactttg ggtgcgctta acttacagta cttttttcgac cacccagaaa   3120
gcttgtcatt gttgaggagc atccacttct caatacgagg aaataagaca tcacccagag    3180
cacatttttc agttctggaa acatgttttg acaaatcaca ggtgccaact atagatcagg    3240
actatgcttc tgccttttgaa cctatgaatg aatgggagcg aaatttagct gaaaagagg    3300
ataatgtaaa gagctatatg gatatgcagc gcagggcatc accagacctt agtactggct    3360
attggaaact ttctccaaag cagtacaaga ttccctgtct agaagtcgat gtgaatgata    3420
ttgatgttgt aggccaggat atgcttgaga ttctaatgac agttttctca gcttcacagc    3480
gcatcgaact ccatttaaac cacagcagag ctttataga aagcatccgc ccagctcttg     3540
agctgtctaa ggcctctgtc accaagtgct ccataagcaa gttggaactc agcgcagccg    3600
aacaggaact gcttctcacc ctgccttccc tggaatctct tgaagtctca gggacaatcc    3660
agtcacaaga ccaaatcttt cctaatctgg ataagttcct gtgcctgaaa gaactgtctg    3720
tggatctgga gggcaatata aatgtttttt cagtcattcc tgaagaattt ccaaacttcc    3780
accatatgga gaaattattg atccaaattt cagctgagta tgatccttcc aaactagtaa    3840
tgccagtttg ccaaatttta tttctctgaa gatattaaat cttgaaggcc agcaatttcc    3900
tgatgaggaa acatcagaaa aatttgccta cattttaggt tctcttagta acctggaaga    3960
attgatcctt cctactgggg atggaattta tcgagtggcc aaactgatca tccagcagtg    4020
tcagcagctt cattgtctcc gagtcctctc atttttcaag actttgaatg atgacagcgt    4080
ggtggaaatt ggttaaaaat gtgtctgcag gcacacagga cgtgccttca cccccatctg    4140
actatgtgga aagagttgac agtcccatgg catactcttc caatggcaaa gtgaatgaca    4200
agcggtttta tccagagtct tcctataaat ccacgccggt tcctgaagtg gttcaggagc    4260
ttccattaac ttcgcctgtg gatgacttca ggcagcctcg ttacagcagc ggtggtaact    4320
ttgagacacc ttcaaaaaga gcacctgcaa agggaagagc aggaaggtca agagaaacag    4380
```

-continued

```
agcaagatca ctatgagaca gactacacaa ctggcggcga gtcctgtgat gagctggagg    4440
aggactggat cagggaatat ccacctatca cttcagatca acaaagacaa ctgtacaaga    4500
ggaattttga cactggccta caggaataca agagcttaca atcagaactt gatgagatca    4560
ataaagaact ctcccgtttg ataaagaat tggatgacta tagagaagaa agtgaagagt    4620
acatggctgc tgctgatgaa tacaatagac tgaagcaagt gaaggatct gcagattaca    4680 aaagtaagaa gaatcattgc aagcagttaa acagcaaatt gtcacacatc aagaagatgg    4740
ttggagacta tgatagacag aaaacataga aggctgatgc caagttgttt gagaaattaa    4800
gtatctgaca tctctgcaat cttctcagaa ggcaaatgac tttggaccat aaccccggaa    4860
gccaaacctc tgtgagcatc acagttttgg ttgctttaat atcatcagta ttgaagcatt    4920
ttataaatcg cttttgataa tcaactgggc tgaacactcc aattaaggat tttatgcttt    4980
aaacattggt tcttgtatta agaatgaaat actgtttgag gtttttaagc cttaaaggaa    5040
ggttctggtg tgaactaaac tttcacaccc cagacgatgt cttcatacct acatgtattt    5100
gtttgcatag gtgatctcat ttaatcctct caaccacctt tcagataact gttatttata    5160
atcacttttt tccacataag gaaactgggt tcctgcaatg aagtctctga agtgaaactg    5220
cttgtttcct agcacacact tttggttaag tctgttttat gacttcatta ataataaatt    5280
ccggcatcat acagctactc ctccctaccg ccacctccac agacaccact ctcctggttc    5340
catctcctct gctgcttcta gctccctgct ctggcttcaa ggtgcgcagg acctgcttcc    5400
ttggtgatcc tctgtagtct cccacacccc acattatcta caaactgatg actcctaatt    5460
tacatctcca gctcagacct ctccatcaat cccaacgcat acac                    5504
```

<210> SEQ ID NO 2
<211> LENGTH: 6133
<212> TYPE: DNA
<213> ORGANISM: Homo sapiens

<400> SEQUENCE: 2

```
tgcatgaaga caaaaggtcc tgtgctcacc tgggacccctt ctggacgttg ccctgtgtac      60
ctcttcgact gcctgttcat ctacgacgaa ccccgggtat tgaccccaga caacaatgcc     120
acttcatatt ggggacttcg tctgggattc caaggtgcat tcattgcaaa gttccttaaa     180
tattttctca ctgcttccta ctaaaggacg gacagagcat ttgttcttca gccacatact     240
ttccttccac tggccagcat tctcctctat tagactagaa ctgtggataa acctcagaaa     300
atggccaccc agcagaaagc ctctgacgag aggatctccc agtttgatca caatttgctg     360
ccagagctgt ctgctcttct gggcctagat gcagttcagt tggcaaagga actagaagaa     420
gaggagcaga aggagcgagc aaaaatgcag aaaggctaca actctcaaat gcgcagtgaa     480
gcaaaaaggt taaagacttt tgtgacttat gagccgtaca gctcatggat accacaggag     540
atggcggccg ctgggttttta cttcactggg gtaaaatctg ggattcagtg cttctgctgt     600
agcctaatcc tctttggtgc cggcctcacg agactcccca tagaagacca caagaggttt     660
catccagatt gtgggttcct tttgaacaag gatgttggta acattgccaa gtacgacata     720
agggtgaaga atctgaagag caggctgaga ggaggtaaaa tgaggtacca agaagaggag     780
gctagacttg cgtccttcag gaactggcca tttatgtcc aagggatatc cccttgtgtg     840
ctctcagagg ctggctttgt ctttacaggt aaacaggaca cggtacagtg ttttttcctgt    900 ggtggatgtt taggaaattg ggaagaagga gatgatcctt ggaaggaaca tgccaaatgg    960
ttccccaaat gtgaatttct tcggagtaag aaatcctcag aggaaattac ccagtatatt    1020
```

-continued

```
caaagctaca agggatttgt tgacataacg ggagaacatt ttgtgaattc ctgggtccag    1080
agagaattac ctatggcatc agcttattgc aatgacagca tctttgctta cgaagaacta    1140
cggctggact cttttaagga ctggccccgg gaatcagctg tgggagttgc agcactggcc    1200
aaagcaggtc ttttctacac aggtataaag gacatcgtcc agtgcttttc ctgtggaggg    1260
tgtttagaga atggcagga aggtgatgac ccattagacg atcacaccag atgttttccc    1320
aattgtccat ttctccaaaa tatgaagtcc tctgcggaag tgactccaga ccttcagagc    1380
cgtggtgaac tttgtgaatt actggaaacc acaagtgaaa gcaatcttga agattcaata    1440
gcagttggtc ctatagtgcc agaaatggca cagggtgaag cccagtggtt tcaagaggca    1500
aagaatctga atgagcagct gagagcagct tataccagcg ccagtttccg ccacatgtct    1560
ttgcttgata tctcttccga tctggccacg gaccacttgc tgggctgtga tctgtctatt    1620
gcttcaaaac acatcagcaa acctgtgcaa gaacctctgg tgctgcctga ggtctttggc    1680
aacttgaact ctgtcatgtg tgtggagggt gaagctggaa gtggaaagac ggtcctcctg    1740
aagaaaatag cttttctgtg ggcatctgga tgctgtcccc tgttaaacag gttccagctg    1800
gttttctacc tctcccttag ttccaccaga ccagacgagg ggctggccag tatcatctgt    1860
gaccagctcc tagagaaaga aggatctgtt actgaaatgt gcatgaggaa cattatccag    1920
cagttaaaga atcaggtctt attccttta gatgactaca agaaaatatg ttcaatccct    1980
caagtcatag gaaaactgat tcaaaaaaac cacttatccc ggacctgcct attgattgct    2040
gtccgtacaa acagggccag ggacatccgc cgatacctag agaccattct agagatcaaa    2100
gcatttccct tttataatac tgtctgtata ttacggaagc tcttttcaca taatatgact    2160
cgtctgcgaa agtttatggt ttactttgga aagaaccaaa gtttgcagaa gatacagaaa    2220
actcctctct ttgtggcggc gatctgtgct cattggtttc agtatccttt tgacccatcc    2280
tttgatgatg tggctgtttt caagtcctat atggaacgcc tttccttaag gaacaaagcg    2340
acagctgaaa ttctcaaagc aactgtgtcc tcctgtggtg agctggcctt gaaagggttt    2400
ttttcatgtt gctttgagtt taatgatgat gatctcgcag aagcaggggt tgatgaagat    2460
gaagatctaa ccatgtgctt gatgagcaaa tttacagccc agagactaag accattctac    2520
cggtttttaa gtcctgcctt ccaagaattt cttgcgggga tgaggctgat tgaactcctg    2580
gattcagata ggcaggaaca tcaagatttg ggactgtatc atttgaaaca aatcaactca    2640
cccatgatga ctgtaagcgc ctacaacaat tttttgaact atgtctccag cctcccttca    2700
acaaaagcag ggcccaaaat tgtgtctcat ttgctccatt tagtggataa caaagagtca    2760
ttggagaata tatctgaaaa tgatgactac ttaaagcacc agccagaaat ttcactgcag    2820
atgcagttac ttaggggatt gtggcaaatt tgtccacaag cttacttttc aatggtttca    2880
gaacatttac tggttcttgc cctgaaaact gcttatcaaa gcaacactgt tgctgcgtgt    2940
tctccatttg ttttgcaatt ccttcaaggg agaacactga ctttgggtgc gcttaactta    3000
cagtactttt tcgaccaccc agaaagcttg tcattgttga ggagcatcca cttcccaata    3060
cgaggaaata agacatcacc cagagcacat ttttcagttc tggaaacatg ttttgacaaa    3120
tcacaggtgc caactataga tcaggactat gcttctgcct ttgaacctat gaatgaatgg    3180
gagcgaaatt tagctgaaaa agaggataat gtaaagagct atatggatat gcagcgcagg    3240
gcatcaccag accttagtac tggctattgg aaactttctc caaagcagta caagattccc    3300
tgtctagaag tcgatgtgaa tgatattgat gttgtaggcc aggatatgct tgagattcta    3360
```

```
atgacagttt tctcagcttc acagcgcatc gaactccatt taaaccacag cagaggcttt    3420
atagaaagca tccgcccagc tcttgagctg tctaaggcct ctgtcaccaa gtgctccata    3480
agcaagttgg aactcagcgc agccgaacag gaactgcttc tcaccctgcc ttccctggaa    3540
tctcttgaag tctcagggac aatccagtca caagaccaaa tctttcctaa tctggataag    3600
ttcctgtgcc tgaaagaact gtctgtggat ctggagggca atataaatgt tttttcagtc    3660
attcctgaag aatttccaaa cttccaccat atggagaaat tattgatcca aatttcagct    3720
gagtatgatc cttccaaact agtaaaatta attcaaaatt ctccaaacct tcatgttttc    3780
catctgaagt gtaacttctt ttcggatttt gggtctctca tgactatgct tgtttcctgt    3840
aagaaactca cagaaattaa gttttcggat tcattttttc aagccgtccc atttgttgcc    3900
agtttgccaa attttatttc tctgaagata ttaaatcttg aaggccagca atttcctgat    3960
gaggaaacat cagaaaaatt tgcctacatt ttaggttctc ttagtaacct ggaagaattg    4020
atccttccta ctggggatgg aatttatcga gtggccaaac tgatcatcca gcagtgtcag    4080
cagcttcatt gtctccgagt cctctcattt ttcaagactt tgaatgatga cagcgtggtg    4140
gaaattgcca agtagcaat cagtggaggt ttccagaaac ttgagaacct aaagctttca    4200
atcaatcaca agattacaga ggaaggatac agaaatttct ttcaagcact ggacaacatg    4260
ccaaacttgc aggagttgga catctccagg catttcacag agtgtatcaa agctcaggcc    4320
acaacagtca agtctttgag tcaatgtgtg ttacgactac caaggctcat tagactgaac    4380
atgttaagtt ggctcttgga tgcagatgat attgcattgc ttaatgtcat gaaagaaaga    4440
catcctcaat ctaagtactt aactattctc cagaaatgga tactgccgtt ctctccaatc    4500
attcagaaat aaaagattca gctaaaaact gctgaatcaa taatttgtct tggggcatat    4560
tgaggatgta aaaaagttg ttgattaatg ctaaaaacca aattatccaa aattatttta    4620
ttaaatattg catacaaaag aaaatgtgta aggcttgcta aaaaacaaaa caaaacaaaa    4680
cacagtcctg catactcacc accaagctca agaaataaat catcaccaat acctttgagg    4740
tccctgagta atccacccca gctaaaggca aacccttcaa tcaagtttat acagcaaacc    4800
ctccattgtc catggtcaac agggaagggg ttggggacag gtctgccaat ctatctaaaa    4860
gccacaatat ggaagaagta ttcaatttat ataataaatg gctaacttaa cggttgaatc    4920
actttcatac atggatgaaa cgggtttaac acaggatcca catgaatctt ctgtgggcca    4980
agagatgttc cttaatcctt gtagaacctg ttttctatat tgaactagct ttggtacagt    5040
agagttaact tactttccat ttatccactg ccaatataaa gaggaaacag gggttaggga    5100
aaaatgactt cattccagag gcttctcaga gttcaacata tgctataatt tagaattttc    5160
ttatgaatcc actctacttg ggtagaaaat attttatctc tagtgattgc atattatttc    5220
catatcatag tatttcatag tattatattt gatatgagtg tctatatcaa tgtcagtgtc    5280
cagaatttcg ttcctaccag ttaagtagtt ttctgaacgg ccagaagacc attcgaaatt    5340
catgatacta ctataagttg gtaaacaacc atacttttat cctcattttt attctcacta    5400
agaaaaaagt caactcccct ccccttgccc aagtatgaaa tatagggaca gtatgtatgg    5460
tgtggtctca tttgtttaga aaaccactta tgactgggtg cggtggctca cacctgtaat    5520
cccagcactt tgggaggctg aggcgggcga atcatttgag gtgaggaatt cgagaccagc    5580
ctggccagca tggtgaaacc ccatctctac taaaaataca aaattagcc aggtgtggtg    5640 gcacatgcct gtagtcccag ccactagggc ggctgagacg caagacttgc ttgaacccgg    5700
gaggcagagg ttgcagtgag ccaagatggc gccactgcat tccagcctgg gcaacagagc    5760
```

-continued

```
aagaccctgt ctgtctcaaa acaaaaaaca aaaccactta tattgctagc tacattaaga    5820
atttctgaat atgttactga gcttgcttgt ggtaaccatt tataatatca gaaagtatat    5880
gtacaccaaa acatgttgaa catccatgtt gtacaactga aatataaata attttgtcaa    5940
ttatacctaa ataaaactgg aaaaaaattt ctggaagttt atatctaaaa atgttaatag    6000
tgcgtacctc taggaagtgg gcctggaagc cattcttact tttcagtctc tcccattctg    6060
tactgttttt tgttttactt tcgtgcctgc attattttc tatttaaaac aaaaataaat     6120
ctagtttagc act                                                       6133

<210> SEQ ID NO 3
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 3
atgcttggat ctctagaatg g                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer based on Homo sapiens

<400> SEQUENCE: 4
agcaaagaca tgtggcggaa                                                20

<210> SEQ ID NO 5
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 5
ccagctccta gagaaagaag ga                                             22

<210> SEQ ID NO 6
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 6
gaactacggc tggactcttt t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 7
ctctcagcct gctcttcaga t                                              21

<210> SEQ ID NO 8
<211> LENGTH: 21
<212> TYPE: DNA
```

-continued

<213> ORGANISM: Artificial Sequence
<220> FEATURE:
<223> OTHER INFORMATION: Synthetic primer based on Homo sapiens

<400> SEQUENCE: 8
aaagcctctg acgagaggat c                                     21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 9
cgactgcctg ttcatctacg a                                     21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 10
tttgttctcc agccacatac t                                     21

<210> SEQ ID NO 11
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 11
catttggcat gttccttcca ag                                    22

<210> SEQ ID NO 12
<211> LENGTH: 27
<212> TYPE: DNA
<213> ORGANISM: Artificial Sequence
<220> FEATURE:
<223> OTHER INFORMATION: Syntehtic primer based on Homo sapiens

<400> SEQUENCE: 12
gtagatgaat actgatgttt cataatt                               27

<210> SEQ ID NO 13
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 13
tgccactgcc aggcaatcta a                                     21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 14
taaacaggac acggtacagt g                                     21

```
<210> SEQ ID NO 15
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 15
catgttttaa gtctcggtgc tctg                                              24

<210> SEQ ID NO 16
<211> LENGTH: 23
<212> TYPE: DNA
<213> ORGANISM: Artificial Sequence
<220> FEATURE:
<223> OTHER INFORMATION: Synthetic primer based on Homo sapiens

<400> SEQUENCE: 16
ttagccagat gtgttggcac atg                                               23

<210> SEQ ID NO 17
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 17
gattctatgt gataggcagc ca                                                22

<210> SEQ ID NO 18
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 18
gccactgctc ccgatggatt a                                                 21

<210> SEQ ID NO 19
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 19
gctctcagct gctcattcag at                                                22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 20
acaaagttca ccacggctct g                                                 21

<210> SEQ ID NO 21
<211> LENGTH: 6124
<212> TYPE: DNA
<213> ORGANISM: Homo sapiens
```

-continued

```
<400> SEQUENCE: 21
acaaaaggtc ctgtgctcac ctgggaccct tctggacgtt gccctgtgta cctcttcgac      60
tgcctgttca tctacgacga accccgggta ttgaccccag acaacaatgc cacttcatat     120
tggggacttc gtctgggatt ccaaggtgca ttcattgcaa agttccttaa atattttctc     180
actgcttcct actaaaggac ggacagagca tttgttcttc agccacatac tttccttcca     240
ctggccagca ttctcctcta ttagactaga actgtggata aacctcagaa aatggccacc     300
cagcagaaag cctctgacga gaggatctcc cagtttgatc acaatttgct gccagagctg     360
tctgctcttc tgggcctaga tgcagttcag ttggcaaagg aactagaaga agaggagcag     420
aaggagcgag caaaaatgca gaaaggctac aactctcaaa tgcgcagtga agcaaaaagg     480
ttaaagactt ttgtgactta tgagccgtac agctcatgga taccacagga gatgcggcc      540 gctgggtttt acttcactgg ggtaaaatct gggattcagt gcttctgctg tagcctaatc     600
ctctttggtg ccggcctcac gagactcccc atagaagacc acaagaggtt tcatccagat     660
tgtgggttcc ttttgaacaa ggatgttggt aacattgcca agtacgacat aagggtgaag     720
aatctgaaga gcaggctgag aggaggtaaa atgaggtacc aagaagagga ggctagactt     780
gcgtccttca ggaactggcc attttatgtc caagggatat cccttgtgt gctctcagag      840 gctggctttt tctttacagg taaacaggac acggtacagt gttttcctg tggtggatgt      900 ttaggaaatt gggaagaagg agatgatcct tggaaggaac atgccaaatg gttccccaaa     960
tgtgaatttc ttcggagtaa gaaatcctca gaggaaatta cccagtatat tcaaagctac    1020
aagggatttg ttgacataac gggagaacat tttgtgaatt cctgggtcca gagagaatta    1080
cctatggcat cagcttattg caatgacagc atctttgctt acgaagaact acggctggac    1140
tcttttaagg actggccccg ggaatcagct gtgggagttg cagcactggc caaagcaggt    1200
cttttctaca caggtataaa ggacatcgtc cagtgctttt cctgtggagg gtgtttagag    1260
aaatggcagg aaggtgatga cccattagac gatcacacca gatgttttcc caattgtcca    1320
tttctccaaa atatgaagtc ctctgcggaa gtgactccag accttcagag ccgtggtgaa    1380
ctttgtgaat tactggaaac cacaagtgaa agcaatcttg aagattcaat agcagttggt    1440
cctatagtgc cagaaatggc acagggtgaa gcccagtggt ttcaagaggc aaagaatctg    1500
aatgagcagc tgagagcagc ttataccagc gccagtttcc gccacatgtc tttgcttgat    1560
atctcttccg atctggccac ggaccacttg ctgggctgtg atctgtctat tgcttcaaaa    1620
cacatcagca aacctgtgca agaacctctg gtgctgcctg aggtctttgg caacttgaac    1680
tctgtcatgt gtgtgagggg tgaagctgga agtggaaaga cggtcctcct gaagaaaata    1740
gcttttctgt gggcatctgg atgctgtccc ctgttaaaca ggttccagct ggttttctac    1800
ctctccctta gttccaccag accagacgag gggctggcca gtatcatctg tgaccagctc    1860
ctagagaaag aaggatctgt tactgaaatg tgcatgagga acattatcca gcagttaaag    1920
aatcaggtct tattccttt agatgactac aaagaaatat gttcaatccc tcaagtcata    1980
ggaaaactga ttcaaaaaaa ccacttatcc cggacctgcc tattgattgc tgtccgtaca    2040
aacagggcca gggacatccg ccgatacctt agaccattc tagagatcaa agcatttccc    2100
ttttataata ctgtctgtat attacggaag ctcttttcac ataatatgac tcgtctgcga    2160
aagtttatgg tttactttgg aaagaaccaa agtttgcaga agatacagaa aactcctctc    2220
tttgtggcgg cgatcgtgc tcattggttt cagtatcctt ttgacccatc ctttgatgat    2280
gtggctgttt tcaagtccta tatggaacgc ctttccttaa ggaacaaagc gacagctgaa    2340
```

-continued

```
attctcaaag caactgtgtc ctcctgtggt gagctggcct tgaaagggtt tttttcatgt    2400
tgctttgagt ttaatgatga tgatctcgca gaagcagggg ttgatgaaga tgaagatcta    2460
accatgtgct tgatgagcaa atttacagcc cagagactaa gaccattcta ccggttttta    2520
agtcctgcct tccaagaatt tcttgcgggg atgaggctga ttgaactcct ggattcagat    2580
aggcaggaac atcaagattt gggactgtat catttgaaac aaatcaactc acccatgatg    2640
actgtaagcg cctacaacaa ttttttgaac tatgtctcca gcctcccttc aacaaaagca    2700
gggcccaaaa ttgtgtctca tttgctccat ttagtggata caaagagtc attggagaat     2760
atatctgaaa atgatgacta cttaaagcac cagccagaaa tttcactgca gatgcagtta    2820
cttaggggat tgtggcaaat ttgtccacaa gcttactttt caatggtttc agaacattta    2880
ctggttcttg ccctgaaaac tgcttatcaa agcaacactg ttgctgcgtg ttctccattt    2940
gttttgcaat tccttcaagg gagaaactg actttgggtg cgcttaactt acagtacttt     3000
ttcgaccacc cagaaagctt gtcattgttg aggagcatcc acttcccaat acgaggaaat    3060
aagcatcac ccagagcaca ttttttcagtt ctggaaacat gttttgacaa atcacaggtg    3120
ccaactatag atcaggacta tgcttctgcc tttgaaccta tgaatgaatg ggagcgaaat    3180
ttagctgaaa aagaggataa tgtaaagagc tatatggata tgcagcgcag ggcatcacca    3240
gaccttagta ctggctattg gaaactttct ccaaagcagt acaagattcc ctgtctagaa    3300
gtcgatgtga atgatattga tgttgtaggc caggatatgc ttgagattct aatgacagtt    3360
ttctcagctt cacagcgcat cgaactccat ttaaaccaca gcagaggctt tatagaaagc    3420
atccgcccag ctcttgagct gtctaaggcc tctgtcacca agtgctccat aagcaagttg    3480
gaactcagcg cagccgaaca ggaactgctt ctcaccctgc cttccctgga atctcttgaa    3540
gtctcaggga caatccagtc acaagaccaa atctttccta atctggataa gttcctgtgc    3600
ctgaaagaac tgtctgtgga tctggagggc aatataaatg tttttttcagt cattcctgaa    3660
gaatttccaa acttccacca tatggagaaa ttattgatcc aaatttcagc tgagtatgat    3720
ccttccaaac tagtaaaatt aattcaaaat tctccaaacc ttcatgtttt ccatctgaag    3780
tgtaacttct tttcggattt tgggtctctc atgactatgc ttgtttcctg taagaaactc    3840
acagaaatta gttttcgga ttcattttt caagccgtcc catttgttgc cagtttgcca      3900
aattttattt ctctgaagat attaaatctt gaaggccagc aatttcctga tgaggaaaca    3960
tcagaaaaat ttgcctacat tttaggttct cttagtaacc tggaagaatt gatccttcct    4020
actggggatg gaattatcg agtggccaaa ctgatcatcc agcagtgtca gcagcttcat     4080
tgtctccgag tcctctcatt tttcaagact ttgaatgatg acagcgtggt ggaaattgcc    4140
aaagtagcaa tcagtggagg tttccagaaa cttgagaacc taaagctttc aatcaatcac    4200
aagattacag aggaaggata cagaaatttc tttcaagcac tggacaacat gccaaacttg    4260
caggagttgg acatctccag gcatttcaca gagtgtatca agctcaggc cacaacagtc      4320
aagtctttga gtcaatgtgt gttacgacta ccaaggctca ttagactgaa catgttaagt    4380
tggctcttgg atgcagatga tattgcattg cttaatgtca tgaaagaaag acatcctcaa    4440
tctaagtact aactattct ccagaaatgg atactgccgt tctctccaat cattcagaaa     4500
taaagattc agctaaaaac tgctgaatca ataatttgtc ttggggcata ttgaggatgt     4560
aaaaaagtt gttgattaat gctaaaaacc aaattatcca aaattatttt attaaatatt     4620
gcatacaaaa gaaaatgtgt aaggcttgct aaaaacaaa acaaaacaaa acacagtcct     4680
```

-continued

```
gcatactcac caccaagctc aagaaataaa tcatcaccaa tacctttgag gtccctgagt      4740
aatccacccc agctaaaggc aaaccccttca atcaagttta tacagcaaac cctccattgt    4800
ccatggtcaa cagggaaggg gttggggaca ggtctgccaa tctatctaaa agccacaata    4860
tggaagaagt attcaattta tataataaat ggctaactta acggttgaat cactttcata    4920
catggatgaa acgggtttaa cacaggatcc acatgaatct tctgtgggcc aagagatgtt    4980
ccttaatcct tgtagaacct gttttctata ttgaactagc tttggtacag tagagttaac    5040
ttactttcca tttatccact gccaatataa agaggaaaca ggggttaggg aaaaatgact    5100
tcattccaga ggcttctcag agttcaacat atgctataat ttagaatttt cttatgaatc    5160
cactctactt gggtagaaaa tattttatct ctagtgattg catattattt ccatatcata    5220
gtatttcata gtattatatt tgatatgagt gtctatatca atgtcagtgt ccagaatttc    5280
gttcctacca gttaagtagt tttctgaacg gccagaagac cattcgaaat tcatgatact    5340
actataagtt ggtaaacaac catacttta tcctcatttt tattctcact aagaaaaaag    5400
tcaactcccc tcccttgcc caagtatgaa atataggggac agtatgtatg gtgtggtctc    5460
atttgtttag aaaaccactt atgactgggt gcggtggctc acacctgtaa tcccagcact    5520
ttgggaggct gaggcgggcg aatcatttga ggtgaggaat tcgagaccag cctggccagc    5580
atggtgaaac cccatctcta ctaaaaatac aaaaattagc caggtgtggt ggcacatgcc    5640
tgtagtccca gccactaggg cggctgagac gcaagacttg cttgaacccg ggaggcagag    5700
gttgcagtga gccaagatgg cgccactgca ttccagcctg ggcaacagag caagaccctg    5760
tctgtctcaa aacaaaaaac aaaaccactt atattgctag ctacattaag aatttctgaa    5820
tatgttactg agcttgcttg tggtaaccat ttataatatc agaaagtata tgtacaccaa    5880
aacatgttga acatccatgt tgtacaactg aaatataaat aattttgtca attataccta    5940
aataaaactg gaaaaaaatt tctggaagtt tatatctaaa aatgttaata gtgcgtacct    6000
ctaggaagtg ggcctggaag ccattcttac ttttcagtct ctcccattct gtactgtttt    6060
ttgttttact ttcgtgcctg cattattttt ctatttaaaa caaaaataaa tctagtttag    6120
cact                                                                  6124
```

<210> SEQ ID NO 22
<211> LENGTH: 1403
<212> TYPE: PRT
<213> ORGANISM: Homo sapiens

<400> SEQUENCE: 22

```
Met Ala Thr Gln Gln Lys Ala Ser Asp Glu Arg Ile Ser Gln Phe Asp
  1               5                  10                  15

His Asn Leu Leu Pro Glu Leu Ser Ala Leu Leu Gly Leu Asp Ala Val
                 20                  25                  30

Gln Leu Ala Lys Glu Leu Glu Glu Glu Gln Lys Glu Arg Ala Lys
             35                  40                  45

Met Gln Lys Gly Tyr Asn Ser Gln Met Arg Ser Glu Ala Lys Arg Leu
         50                  55                  60

Lys Thr Phe Val Thr Tyr Glu Pro Tyr Ser Ser Trp Ile Pro Gln Glu
 65                  70                  75                  80

Met Ala Ala Ala Gly Phe Tyr Phe Thr Gly Val Lys Ser Gly Ile Gln
                 85                  90                  95

Cys Phe Cys Cys Ser Leu Ile Leu Phe Gly Ala Gly Leu Thr Arg Leu
                100                 105                 110
```

-continued

```
Pro Ile Glu Asp His Lys Arg Phe His Pro Asp Cys Gly Phe Leu Leu
    115                 120                 125

Asn Lys Asp Val Gly Asn Ile Ala Lys Tyr Asp Ile Arg Val Lys Asn
130                 135                 140

Leu Lys Ser Arg Leu Arg Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
    210                 215                 220

Glu Phe Leu Arg Ser Lys Lys Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
    370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
        435                 440                 445

Val Gln Glu Pro Leu Val Leu Pro Glu Val Phe Gly Asn Leu Asn Ser
    450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
        515                 520                 525

Ser Val Thr Glu Met Cys Met Arg Asn Ile Ile Gln Gln Leu Lys Asn
```

```
                530                 535                 540
Gln Val Leu Phe Leu Leu Asp Asp Tyr Lys Glu Ile Cys Ser Ile Pro
545                 550                 555                 560
Gln Val Ile Gly Lys Leu Ile Gln Lys Asn His Leu Ser Arg Thr Cys
                565                 570                 575
Leu Leu Ile Ala Val Arg Thr Asn Arg Ala Arg Asp Ile Arg Arg Tyr
                580                 585                 590
Leu Glu Thr Ile Leu Glu Ile Lys Ala Phe Pro Phe Tyr Asn Thr Val
                595                 600                 605
Cys Ile Leu Arg Lys Leu Phe Ser His Asn Met Thr Arg Leu Arg Lys
610                 615                 620
Phe Met Val Tyr Phe Gly Lys Asn Gln Ser Leu Gln Lys Ile Gln Lys
625                 630                 635                 640
Thr Pro Leu Phe Val Ala Ala Ile Cys Ala His Trp Phe Gln Tyr Pro
                645                 650                 655
Phe Asp Pro Ser Phe Asp Asp Val Ala Val Phe Lys Ser Tyr Met Glu
                660                 665                 670
Arg Leu Ser Leu Arg Asn Lys Ala Thr Ala Glu Ile Leu Lys Ala Thr
                675                 680                 685
Val Ser Ser Cys Gly Glu Leu Ala Leu Lys Gly Phe Phe Ser Cys Cys
                690                 695                 700
Phe Glu Phe Asn Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
                725                 730                 735
Arg Pro Phe Tyr Arg Phe Leu Ser Pro Ala Phe Gln Glu Phe Leu Ala
                740                 745                 750
Gly Met Arg Leu Ile Glu Leu Leu Asp Ser Asp Arg Gln Glu His Gln
                755                 760                 765
Asp Leu Gly Leu Tyr His Leu Lys Gln Ile Asn Ser Pro Met Met Thr
                770                 775                 780
Val Ser Ala Tyr Asn Asn Phe Leu Asn Tyr Val Ser Ser Leu Pro Ser
785                 790                 795                 800
Thr Lys Ala Gly Pro Lys Ile Val Ser His Leu Leu His Leu Val Asp
                805                 810                 815
Asn Lys Glu Ser Leu Glu Asn Ile Ser Glu Asn Asp Asp Tyr Leu Lys
                820                 825                 830
His Gln Pro Glu Ile Ser Leu Gln Met Gln Leu Leu Arg Gly Leu Trp
                835                 840                 845
Gln Ile Cys Pro Gln Ala Tyr Phe Ser Met Val Ser Glu His Leu Leu
850                 855                 860
Val Leu Ala Leu Lys Thr Ala Tyr Gln Ser Asn Thr Val Ala Ala Cys
865                 870                 875                 880
Ser Pro Phe Val Leu Gln Phe Leu Gln Gly Arg Thr Leu Thr Leu Gly
                885                 890                 895
Ala Leu Asn Leu Gln Tyr Phe Phe Asp His Pro Glu Ser Leu Ser Leu
                900                 905                 910
Leu Arg Ser Ile His Phe Pro Ile Arg Gly Asn Lys Thr Ser Pro Arg
                915                 920                 925
Ala His Phe Ser Val Leu Glu Thr Cys Phe Asp Lys Ser Gln Val Pro
                930                 935                 940
Thr Ile Asp Gln Asp Tyr Ala Ser Ala Phe Glu Pro Met Asn Glu Trp
945                 950                 955                 960
```

```
Glu Arg Asn Leu Ala Glu Lys Glu Asp Asn Val Lys Ser Tyr Met Asp
              965                 970                 975
Met Gln Arg Arg Ala Ser Pro Asp Leu Ser Thr Gly Tyr Trp Lys Leu
            980                 985                 990
Ser Pro Lys Gln Tyr Lys Ile Pro Cys Leu Glu Val Asp Val Asn Asp
        995                 1000                1005
Ile Asp Val Val Gly Gln Asp Met Leu Glu Ile Leu Met Thr Val Phe
    1010                1015                1020
Ser Ala Ser Gln Arg Ile Glu Leu His Leu Asn His Ser Arg Gly Phe
1025                1030                1035                104
Ile Glu Ser Ile Arg Pro Ala Leu Glu Leu Ser Lys Ala Ser Val Thr
                1045                1050                1055
Lys Cys Ser Ile Ser Lys Leu Glu Leu Ser Ala Ala Glu Gln Glu Leu
                1060                1065                1070
Leu Leu Thr Leu Pro Ser Leu Glu Ser Leu Glu Val Ser Gly Thr Ile
                1075                1080                1085
Gln Ser Gln Asp Gln Ile Phe Pro Asn Leu Asp Lys Phe Leu Cys Leu
    1090                1095                1100
Lys Glu Leu Ser Val Asp Leu Glu Gly Asn Ile Asn Val Phe Ser Val
1105                1110                1115                112
Ile Pro Glu Glu Phe Pro Asn Phe His His Met Glu Lys Leu Leu Ile
                1125                1130                1135
Gln Ile Ser Ala Glu Tyr Asp Pro Ser Lys Leu Val Lys Leu Ile Gln
                1140                1145                1150
Asn Ser Pro Asn Leu His Val Phe His Leu Lys Cys Asn Phe Phe Ser
                1155                1160                1165
Asp Phe Gly Ser Leu Met Thr Met Leu Val Ser Cys Lys Lys Leu Thr
    1170                1175                1180
Glu Ile Lys Phe Ser Asp Ser Phe Phe Gln Ala Val Pro Phe Val Ala
1185                1190                1195                120
Ser Leu Pro Asn Phe Ile Ser Leu Lys Ile Leu Asn Leu Glu Gly Gln
                1205                1210                1215
Gln Phe Pro Asp Glu Glu Thr Ser Glu Lys Phe Ala Tyr Ile Leu Gly
            1220                1225                1230
Ser Leu Ser Asn Leu Glu Glu Leu Ile Leu Pro Thr Gly Asp Gly Ile
        1235                1240                1245
Tyr Arg Val Ala Lys Leu Ile Ile Gln Gln Cys Gln Gln Leu His Cys
    1250                1255                1260
Leu Arg Val Leu Ser Phe Phe Lys Thr Leu Asn Asp Asp Ser Val Val
1265                1270                1275                128
Glu Ile Ala Lys Val Ala Ile Ser Gly Gly Phe Gln Lys Leu Glu Asn
                1285                1290                1295
Leu Lys Leu Ser Ile Asn His Lys Ile Thr Glu Glu Gly Tyr Arg Asn
                1300                1305                1310
Phe Phe Gln Ala Leu Asp Asn Met Pro Asn Leu Gln Glu Leu Asp Ile
            1315                1320                1325
Ser Arg His Phe Thr Glu Cys Ile Lys Ala Gln Ala Thr Thr Val Lys
    1330                1335                1340
Ser Leu Ser Gln Cys Val Leu Arg Leu Pro Arg Leu Ile Arg Leu Asn
1345                1350                1355                136
Met Leu Ser Trp Leu Leu Asp Ala Asp Asp Ile Ala Leu Leu Asn Val
                1365                1370                1375
```

-continued

```
Met Lys Glu Arg His Pro Gln Ser Lys Tyr Leu Thr Ile Leu Gln Lys
        1380                1385                1390

Trp Ile Leu Pro Phe Ser Pro Ile Ile Gln Lys
        1395                1400

<210> SEQ ID NO 23
<211> LENGTH: 6228
<212> TYPE: DNA
<213> ORGANISM: Homo sapiens

<400> SEQUENCE: 23
ttccggctgg acgttgccct gtgtacctct tcgactgcct gttcatctac gacgaacccc      60
gggtattgac cccagacaac aatgccactt catattgcat gaagacaaaa ggtcctgtgc     120
tcacctggga cccttctgga cgttgccctg tgtacctctt cgactgcctg ttcatctacg     180
acgaaccccg ggtattgacc ccagacaaca atgccacttc atattgggga cttcgtctgg     240
gattccaagg tgcattcatt gcaaagttcc ttaaatattt tctcactgct tcctactaaa     300
ggacggacag agcatttgtt cttcagccac atactttcct tccactggcc agcattctcc     360
tctattagac tagaactgtg gataaacctc agaaaatggc acccagcag aaagcctctg      420 acgagaggat ctcccagttt gatcacaatt gctgccaga gctgtctgct cttctgggcc      480
tagatgcagt tcagttggca aaggaactag aagaagagga gcagaaggag cgagcaaaaa     540
tgcagaaagg ctacaactct caaatgcgca gtgaagcaaa aaggttaaag acttttgtga     600
cttatgagcc gtacagctca tggataccac aggagatggc ggccgctggg ttttacttca     660
ctggggtaaa atctgggatt cagtgcttct gctgtagcct aatcctcttt ggtgccggcc     720
tcacgagact ccccatagaa gaccacaaga ggtttcatcc agattgtggg ttccttttga     780
acaaggatgt tggtaacatt gccaagtacg acataagggt gaagaatctg aagagcaggc     840
tgagaggagg taaaatgagg taccaagaag aggaggctag acttgcgtcc ttcaggaact     900
ggccatttta tgtccaaggg atatcccctt gtgtgctctc agaggctggc tttgtcttta     960
caggtaaaca ggacacggta cagtgttttt cctgtggtgg atgtttagga aattgggaag    1020
aaggagatga tccttggaag gaacatgcca atggttccc caaatgtgaa tttcttcgga    1080
gtaagaaatc ctcagaggaa attacccagt atattcaaag ctacaaggga tttgttgaca    1140
taacgggaga acattttgtg aattcctggg tccagagaga attacctatg gcatcagctt    1200
attgcaatga cagcatcttt gcttacgaag aactacggct ggactctttt aaggactggc    1260
cccgggaatc agctgtggga gttgcagcac tggccaaagc aggtctttc tacacaggta    1320 taaaggacat cgtccagtgc ttttcctgtg gagggtgttt agagaaatgg caggaaggtg    1380
atgacccatt agacgatcac accagatgtt tccccaattg tccatttctc caaaatatga    1440
agtcctctgc ggaagtgact ccagaccttc agagccgtgg tgaactttgt gaattactgg    1500 aaccacaag tgaaagcaat cttgaagatt caatagcagt tggtcctata gtgccagaaa    1560
tggcacaggg tgaagcccag tggtttcaag aggcaaagaa tctgaatgag cagctgagag    1620
cagcttatac cagcgccagt ttccgccaca tgtctttgct tgatatctct tccgatctgg    1680
ccacggacca cttgctgggc tgtgatctgt ctattgcttc aaaacacatc agcaaacctg    1740
tgcaagaacc tctggtgctg cctgaggtct ttggcaactt gaactctgtc atgtgtgtgg    1800
agggtgaagc tggaagtgga aagacggtcc tcctgaagaa aatagctttt ctgtgggcat    1860
ctggatgctg tccctgtta aacaggttcc agctggtttt ctacctctcc cttagttcca    1920
ccagaccaga cgagggggctg gccagtatca tctgtgacca gctcctagag aaagaaggat    1980
```

-continued

```
ctgttactga aatgtgcatg aggaacatta tccagcagtt aaagaatcag gtcttattcc    2040 tttagatga ctacaaagaa atatgttcaa tccctcaagt cataggaaaa ctgattcaaa    2100
aaaaccactt atcccggacc tgcctattga ttgctgtccg tacaaacagg gccagggaca    2160
tccgccgata cctagagacc attctagaga tccaagcatt tcccttttat aatactgtct    2220
gtatattacg gaagctcttt tcacataata tgactcgtct gcgaaagttt atggtttact    2280
ttggaaagaa ccaaagtttg cagaagatac agaaaactcc tctctttgtg gcggcgatct    2340
gtgctcattg gtttcagtat cctttttgacc catcctttga tgatgtggct gttttcaagt    2400
cctatatgga acgcctttcc ttaaggaaca aagcgacagc tgaaattctc aaagcaactg    2460
tgtcctcctg tggtgagctg gccttgaaag ggttttttc atgttgcttt gagtttaatg    2520
atgatgatct cgcagaagca ggggttgatg aagatgaaga tctaaccatg tgcttgatga    2580
gcaaatttac agcccagaga ctaagaccat tctaccggtt tttaagtcct gccttccaag    2640
aatttcttgc ggggatgagg ctgattgaac tcctggattc agataggcag gaacatcaag    2700
atttgggact gtatcatttg aaacaaatca actcacccat gatgactgta agcgcctaca    2760
acaatttttt gaactatgtc tccagcctcc cttcaacaaa agcagggccc aaaattgtgt    2820
ctcatttgct ccatttagtg gataacaaag agtcattgga gaatatatct gaaaatgatg    2880
actacttaaa gcaccagcca gaaatttcac tgcagatgca gttacttagg ggattgtggc    2940
aaatttgtcc acaagcttac ttttcaatgg tttcagaaca tttactggtt cttgccctga    3000
aaactgctta tcaaagcaac actgttgctg cgtgttctcc atttgttttg caattccttc    3060
aagggagaac actgactttg ggtgcgctta acttacagta ctttttcgac cacccagaaa    3120
gcttgtcatt gttgaggagc atccacttcc caatacgagg aaataagaca tcacccagag    3180 cacattttc agttctggaa acatgttttg acaaatcaca ggtgccaact atagatcagg    3240
actatgcttc tgcctttgaa cctatgaatg aatgggagcg aaatttagct gaaaagagg    3300 ataatgtaaa gagctatatg gatatgcagc gcagggcatc accagacctt agtactggct    3360
attggaaact ttctccaaag cagtacaaga ttccctgtct agaagtcgat gtgaatgata    3420
ttgatgttgt aggccaggat atgcttgaga ttctaatgac agttttctca gcttcacagc    3480
gcatcgaact ccatttaaac cacagcagag gctttatata aagcatccgc ccagctcttg    3540
agctgtctaa ggcctctgtc accaagtgct ccataagcaa gttggaactc agcgcagccg    3600
aacaggaact gcttctcacc ctgccttccc tggaatctct tgaagtctca gggacaatcc    3660
agtcacaaga ccaaatcttt cctaatctgg ataagttcct gtgcctgaaa gaactgtctg    3720
tggatctgga gggcaatata aatgttttt cagtcattcc tgaagaattt ccaaacttcc    3780
accatatgga gaaattattg atccaaattt cagctgagta tgatccttcc aaactagtaa    3840
aattaattca aaattctcca aaccttcatg ttttccatct gaagtgtaac ttcttttcgg    3900
atttagggtc tctcatgact atgcttgttt cctgtaagaa actcacagaa attaagtttt    3960
cggattcatt ttttcaagcc gtcccatttg ttgccagttt gccaaatttt atttctctga    4020
agatattaaa tcttgaaggc cagcaatttc ctgatgagga acatcagaa aaatttgcct    4080 acatttagg ttctcttagt aacctggaag aattgatcct tcctactggg gatggaattt    4140
atcgagtggc caaactgatc atccagcagt gtcagcagct tcattgtctc cgagtcctct    4200 cattttttcaa gactttgaat gatgacagcg tggtggaaat tgccaaagta gcaatcagtg    4260
gaggtttcca gaaacttgag aacctaaagc tttcaatcaa tcacaagatt acagaggaag    4320
```

| | |
|---|---|
| gatacagaaa tttctttcaa gcactggaca acatgccaaa cttgcaggag ttggacatct | 4380 |
| ccaggcattt cacagagtgt atcaaagctc aggccacaac agtcaagtct ttgagtcaat | 4440 |
| gtgtgttacg actaccaagg ctcattagac tgaacatgtt aagttggctc ttggatgcag | 4500 |
| atgatattgc attgcttaat gtcatgaaag aaagacatcc tcaatctaag tacttaacta | 4560 |
| ttctccagaa atggatactg ccgttctctc caatcattca gaaataaaag attcagctaa | 4620 |
| aaactgctga atcaataatt tgtcttgggg catattgagg atgtaaaaaa agttgttgat | 4680 |
| taatgctaaa aaccaaatta tccaaaatta ttttattaaa tattgcatac aaaagaaaat | 4740 |
| gtgtaaggct tgctaaaaaa caaaacaaaa caaaacacag tcctgcatac tcaccaccaa | 4800 |
| gctcaagaaa taaatcatca ccaataccctt tgaggtccct gagtaatcca ccccagctaa | 4860 |
| aggcaaaccc ttcaatcaag tttatacagc aaaccctcca ttgtccatgg tcaacaggga | 4920 |
| aggggttggg gacaggtctg ccaatctatc taaaagccac aatatggaag aagtattcaa | 4980 |
| tttatataat aaatggctaa cttaacggtt gaatcacttt catacatgga tgaaacgggt | 5040 |
| ttaacacagg atccacatga atcttctgtg ggccaagaga tgttccttaa tccttgtaga | 5100 |
| acctgttttc tatattgaac tagctttggt acagtagagt taacttactt tccatttatc | 5160 |
| cactgccaat ataaagagga acaggggtt agggaaaaat gacttcattc cagaggcttc | 5220 |
| tcagagttca acatatgcta aatttagaa ttttcttatg aatccactct acttgggtag | 5280 |
| aaaatatttt atctctagtg attgcatatt atttccatat catagtattt catagtatta | 5340 |
| tatttgatat gagtgtctat atcaatgtca gtgtccagaa tttcgttcct accagttaag | 5400 |
| tagttttctg aacggccaga agaccattcg aaattcatga tactactata agttggtaaa | 5460 |
| caaccatact tttatcctca tttttattct cactaagaaa aaagtcaact cccctccct | 5520 |
| tgcccaagta tgaaatatag ggacagtatg tatggtgtgg tctcatttgt ttagaaaacc | 5580 |
| acttatgact gggtgcggtg gctcacacct gtaatcccag cactttggga ggctgaggcg | 5640 |
| ggcgaatcat ttgaggtgag gaattcgaga ccagcctggc cagcatggtg aaacccccatc | 5700 |
| tctactaaaa atacaaaaat tagccaggtg tggtggcaca tgcctgtagt cccagccact | 5760 |
| agggcggctg agacgcaaga cttgcttgaa cccgggaggc agaggttgca gtgagccaag | 5820 |
| atggcgccac tgcattccag cctgggcaac agagcaagac cctgtctgtc tcaaaacaaa | 5880 |
| aaacaaaacc acttatattg ctagctacat taagaatttc tgaatatgtt actgagcttg | 5940 |
| cttgtggtaa ccatttataa tatcagaaag tatatgtaca ccaaaacatg ttgaacatcc | 6000 |
| atgttgtaca actgaaatat aaataatttt gtcaattata cctaaataaa actggaaaaa | 6060 |
| aatttctgga agtttatatc taaaaatgtt aatagtgcgt acctctagga agtgggcctg | 6120 |
| gaagccattc ttacttttca gtctctccca ttctgtactg ttttttgttt tactttcgtg | 6180 |
| cctgcattat ttttctattt aaaacaaaaa taaatctagt ttagcact | 6228 |

<210> SEQ ID NO 24
<211> LENGTH: 1403
<212> TYPE: PRT
<213> ORGANISM: Homo sapiens

<400> SEQUENCE: 24

Met Ala Thr Gln Gln Lys Ala Ser Asp Glu Arg Ile Ser Gln Phe Asp
 1               5                  10                  15

His Asn Leu Leu Pro Glu Leu Ser Ala Leu Leu Gly Leu Asp Ala Val
             20                  25                  30

Gln Leu Ala Lys Glu Leu Glu Glu Glu Glu Gln Lys Glu Arg Ala Lys

-continued

```
                35                  40                  45
Met Gln Lys Gly Tyr Asn Ser Gln Met Arg Ser Glu Ala Lys Arg Leu
 50                  55                  60

Lys Thr Phe Val Thr Tyr Glu Pro Tyr Ser Ser Trp Ile Pro Gln Glu
 65                  70                  75                  80

Met Ala Ala Gly Phe Tyr Phe Thr Gly Val Lys Ser Gly Ile Gln
                 85                  90                  95

Cys Phe Cys Cys Ser Leu Ile Leu Phe Gly Ala Gly Leu Thr Arg Leu
                100                 105                 110

Pro Ile Glu Asp His Lys Arg Phe His Pro Asp Cys Gly Phe Leu Leu
                115                 120                 125

Asn Lys Asp Val Gly Asn Ile Ala Lys Tyr Asp Ile Arg Val Lys Asn
130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
                180                 185                 190

Asp Thr Val Gln Cys Phe Ser Cys Gly Gly Cys Leu Gly Asn Trp Glu
                195                 200                 205

Glu Gly Asp Asp Pro Trp Lys Glu His Ala Lys Trp Phe Pro Lys Cys
                210                 215                 220

Glu Phe Leu Arg Ser Lys Lys Ser Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
                260                 265                 270

Ser Ile Phe Ala Tyr Glu Glu Leu Arg Leu Asp Ser Phe Lys Asp Trp
                275                 280                 285

Pro Arg Glu Ser Ala Val Gly Val Ala Ala Leu Ala Lys Ala Gly Leu
                290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
                340                 345                 350

Glu Val Thr Pro Asp Leu Gln Ser Arg Gly Glu Leu Cys Glu Leu Leu
                355                 360                 365

Glu Thr Thr Ser Glu Ser Asn Leu Glu Asp Ser Ile Ala Val Gly Pro
                370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
                420                 425                 430

Leu Leu Gly Cys Asp Leu Ser Ile Ala Ser Lys His Ile Ser Lys Pro
                435                 440                 445

Val Gln Glu Pro Leu Val Leu Pro Glu Val Phe Gly Asn Leu Asn Ser
450                 455                 460
```

```
Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
                515                 520                 525

Ser Val Thr Glu Met Cys Met Arg Asn Ile Ile Gln Gln Leu Lys Asn
            530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
                565                 570                 575

Leu Leu Ile Ala Val Arg Thr Asn Arg Ala Arg Asp Ile Arg Arg Tyr
            580                 585                 590

Leu Glu Thr Ile Leu Glu Ile Lys Ala Phe Pro Phe Tyr Asn Thr Val
            595                 600                 605

Cys Ile Leu Arg Lys Leu Phe Ser His Asn Met Thr Arg Leu Arg Lys
610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
                645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
            675                 680                 685

Val Ser Ser Cys Gly Glu Leu Ala Leu Lys Gly Phe Phe Ser Cys Cys
            690                 695                 700

Phe Glu Phe Asn Asp Asp Leu Ala Glu Ala Gly Val Asp Glu Asp
705                 710                 715                 720

Glu Asp Leu Thr Met Cys Leu Met Ser Lys Phe Thr Ala Gln Arg Leu
                725                 730                 735

Arg Pro Phe Tyr Arg Phe Leu Ser Pro Ala Phe Gln Glu Phe Leu Ala
            740                 745                 750

Gly Met Arg Leu Ile Glu Leu Leu Asp Ser Asp Arg Gln Glu His Gln
            755                 760                 765

Asp Leu Gly Leu Tyr His Leu Lys Gln Ile Asn Ser Pro Met Met Thr
770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
                805                 810                 815

Asn Lys Glu Ser Leu Glu Asn Ile Ser Glu Asn Asp Asp Tyr Leu Lys
            820                 825                 830

His Gln Pro Glu Ile Ser Leu Gln Met Gln Leu Leu Arg Gly Leu Trp
            835                 840                 845

Gln Ile Cys Pro Gln Ala Tyr Phe Ser Met Val Ser Glu His Leu Leu
            850                 855                 860

Val Leu Ala Leu Lys Thr Ala Tyr Gln Ser Asn Thr Val Ala Ala Cys
865                 870                 875                 880
```

-continued

```
Ser Pro Phe Val Leu Gln Phe Leu Gln Gly Arg Thr Leu Thr Leu Gly
                885                 890                 895

Ala Leu Asn Leu Gln Tyr Phe Phe Asp His Pro Glu Ser Leu Ser Leu
            900                 905                 910

Leu Arg Ser Ile His Phe Pro Ile Arg Gly Asn Lys Thr Ser Pro Arg
        915                 920                 925

Ala His Phe Ser Val Leu Glu Thr Cys Phe Asp Lys Ser Gln Val Pro
    930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
                965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
        995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                104

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
            1060                1065                1070

Leu Leu Thr Leu Pro Ser Leu Glu Ser Leu Glu Val Ser Gly Thr Ile
        1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                112

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Lys Leu Ile Gln
            1140                1145                1150

Asn Ser Pro Asn Leu His Val Phe His Leu Lys Cys Asn Phe Phe Ser
        1155                1160                1165

Asp Phe Gly Ser Leu Met Thr Met Leu Val Ser Cys Lys Lys Leu Thr
    1170                1175                1180

Glu Ile Lys Phe Ser Asp Ser Phe Phe Gln Ala Val Pro Phe Val Ala
1185                1190                1195                120

Ser Leu Pro Asn Phe Ile Ser Leu Lys Ile Leu Asn Leu Glu Gly Gln
                1205                1210                1215

Gln Phe Pro Asp Glu Glu Thr Ser Glu Lys Phe Ala Tyr Ile Leu Gly
            1220                1225                1230

Ser Leu Ser Asn Leu Glu Glu Leu Ile Leu Pro Thr Gly Asp Gly Ile
        1235                1240                1245

Tyr Arg Val Ala Lys Leu Ile Ile Gln Gln Cys Gln Gln Leu His Cys
    1250                1255                1260

Leu Arg Val Leu Ser Phe Phe Lys Thr Leu Asn Asp Asp Ser Val Val
1265                1270                1275                128

Glu Ile Ala Lys Val Ala Ile Ser Gly Gly Phe Gln Lys Leu Glu Asn
                1285                1290                1295

Leu Lys Leu Ser Ile Asn His Lys Ile Thr Glu Glu Gly Tyr Arg Asn
```

-continued

```
              1300                1305                1310
Phe Phe Gln Ala Leu Asp Asn Met Pro Asn Leu Gln Glu Leu Asp Ile
        1315                1320                1325
Ser Arg His Phe Thr Glu Cys Ile Lys Ala Gln Ala Thr Thr Val Lys
    1330                1335                1340
Ser Leu Ser Gln Cys Val Leu Arg Leu Pro Arg Leu Ile Arg Leu Asn
1345                1350                1355                136
Met Leu Ser Trp Leu Leu Asp Ala Asp Asp Ile Ala Leu Leu Asn Val
                1365                1370                1375
Met Lys Glu Arg His Pro Gln Ser Lys Tyr Leu Thr Ile Leu Gln Lys
            1380                1385                1390
Trp Ile Leu Pro Phe Ser Pro Ile Ile Gln Lys
        1395                1400

<210> SEQ ID NO 25
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 25
gtgaactgca ctgtgacaag ctgc                                    24

<210> SEQ ID NO 26
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 26
atataaacaa cgaattatct cc                                      22

<210> SEQ ID NO 27
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 27
gtattataat caataagtta tacc                                    24
```